(12) United States Patent
Damaj et al.

(10) Patent No.: US 9,631,199 B2
(45) Date of Patent: Apr. 25, 2017

(54) STEM-SPECIFIC PROMOTER FROM SUGARCANE DIRIGENT GENE

(71) Applicant: THE TEXAS A&M UNIVERSITY SYSTEM, College Station, TX (US)

(72) Inventors: Mona B. Damaj, Westlaco, TX (US); T. Erik Mirkov, Harlingen, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 218 days.

(21) Appl. No.: 14/644,091

(22) Filed: Mar. 10, 2015

(65) Prior Publication Data

US 2015/0259697 A1 Sep. 17, 2015

Related U.S. Application Data

(60) Provisional application No. 61/950,788, filed on Mar. 10, 2014, provisional application No. 61/950,599, filed on Mar. 10, 2014.

(51) Int. Cl.
*C12N 15/82* (2006.01)
*C07H 21/04* (2006.01)
*C12N 9/24* (2006.01)

(52) U.S. Cl.
CPC ....... *C12N 15/8226* (2013.01); *C12N 9/2402* (2013.01); *C12Y 302/01031* (2013.01)

(58) Field of Classification Search
None
See application file for complete search history.

(56) References Cited

U.S. PATENT DOCUMENTS

| | | |
|---|---|---|
| 7,253,276 B2 | 8/2007 | Damaj et al. |
| 7,323,622 B2 | 1/2008 | Mirkov et al. |
| 7,754,946 B2 | 7/2010 | Damaj et al. |
| 7,973,217 B2 | 7/2011 | Mirkov et al. |
| 8,710,207 B2 | 4/2014 | Mirkov et al. |
| 2011/0283377 A1 | 11/2011 | Mirkov et al. |
| 2013/0247252 A1 | 9/2013 | Damaj et al. |
| 2014/0068817 A1 | 3/2014 | Dittmar et al. |

FOREIGN PATENT DOCUMENTS

| | | | |
|---|---|---|---|
| WO | WO 01/18211 | * 3/2001 | ............. C12N 15/29 |
| WO | 2012/119152 A1 | 9/2012 | |
| WO | 2013/142420 A1 | 9/2013 | |

OTHER PUBLICATIONS

Baumann K, De Paolis A, Costantino P, Gualberti G (1999) DNA binding site of the Dof protein NtBBF1 is essential for tissue-specific and auxin-regulated expression of the rolB oncogene in plants. Plant Cell 11:323-334.
Beyene G, Buenrostro-Nava MT, Damaj MB, Gao S-J, Molina J, Mirkov TE (2011) Unprecedented enhancement of transient gene expression from minimal cassettes using a double terminator. Plant Cell Reports 30:13-25.
Christensen AH, Sharrock RA, Quail PH (1992) Maize polyubiquitin genes: structure, thermal perturbation of expression and transcript splicing, and promoter activity following transfer to protoplasts by electroporation. Plant Molecular Biology 18:675-689.
da Costa e Silva O, Klein L, Schmelzer E, Trezzini GF, Hahlbrock K (1993) BPF-1, a pathogen-induced DNA-binding protein involved in the plant defense responses. Plant Journal 4:125-135.
Damaj MB, Kumpatla SP, Emani C, Beremand PD, Reddy AS, Rathore KS, Buenrostro-Nava MT, Curtis IS, Thomas TL, Mirkov TE (2010) Sugarcane Dirigent and O-Methyltransferase promoters confer stem-regulated gene expression in diverse monocots. Planta 231:1439-1458.
Feuillet C, Lauvergeat V, Deswarte C, Pilate G, Boudet A, Grima-Pettenati J (1995) Tissue- and cell-specific expression of a cinnamyl alcohol dehydrogenase promoter in transgenic poplar plants. Plant Molecular Biology 27:651-667.
Fornalé S, Sonbol F-M, Maes T, Capellades M, Puigdomènech P, Rigau J, Caparrós-Ruiz D (2006) Down-regulation of the maize and Arabidopsis thaliana caffeic acid O-methyl-transferase genes by two new maize R2R3-MYB transcription factors Plant Molecular Biology 62:809-823.
Gallo-Meagher M, Irvine JE (1996) Herbicide resistant transgenic sugarcane plants containing the bar gene. Crop Science 36:1367-1374.
Groenewald J-H, Botha FC (2008) Down-regulation of pyrophosphate: fructose 6-phosphate 1-phosphotransferase (PFP) activity in sugarcane enhances sucrose accumulation in immature internodes. Transgenic Research 17:85-92.
Hiroyuki K, Terauchi R (2008) Regulation of expression of rice thaumatin-like protein: inducibility by elicitor requires promoter W-box elements. Plant Cell Reports 27:1521-1528.
Hwang S-H, Lee IA, Yie SW, Hwang D-J (2008) Identification of an OsPR10a promoter region responsive to salicylic acid. Planta 227:1141-1150.
Ito H, Hiraqa S, Tsuqawa H, Matsui H, Honma M, Otsuki Y, Murakami T, Ohashi Y (2000) Xylem-specific expression of wound-inducible rice peroxidase genes in transgenic plants. Plant Science 155:85-100.
Jin-long G., Li-ping X., Jing-ping F., Ya-chun S., Hua-ying F., You-xiong Q., Jing-sheng X. (2012) A novel dirigent protein gene with highly stem-specific expression from sugarcane, response to drought, salt and oxidative stresses. Plant Cell Reports 31:1801-1812.
Lacombe E, Van Doorsselaere J, Boerjan W, Boudet AM, Grima-Pettenati J (2000) Characterization of cis-elements required for vascular expression of the Cinnamoyl CoA Reductase gene and for protein-DNA complex formation. Plant Journal 23:663-676.
Liu Z-Z, Wang J-L, Huang X, Xu W-H, Liu Z-M, Fang R-X (2003) The promoter of a rice glycine-rich protein gene, Osgrp-2, confers vascular-specific expression in transgenic plants. Planta 216:824-833.

(Continued)

*Primary Examiner* — Cathy Kingdon Worley
(74) *Attorney, Agent, or Firm* — Baker & McKenzie LLP

(57) ABSTRACT

The present disclosure relates, according to some embodiments, to compositions, organisms, systems, and methods for expressing a gene product in a plant (e.g., a monocot) using a promoter operable in one or more plant tissues and/or cells. In some embodiments, an artificial nucleic acid may comprise an expression control sequence having the sequence selected from the sequence of nucleotides 1-4710 of SEQ ID NO: 1 and the sequence of nucleotides 1137-4710 of SEQ ID NO: 1, wherein the expression control sequence has stem-regulated promoter activity in at least one monocot (e.g., at least two monocots).

19 Claims, 18 Drawing Sheets

(13 of 18 Drawing Sheet(s) Filed in Color)

(56) References Cited

OTHER PUBLICATIONS

Opalka N, Brugidou C, Bonneau C, Nicole M, Yeager M, Fauquet C (1998) Movement of rice yellow mottle virus between xylem cells through pit membranes. Proceedings of National Academy of Sciences USA 95:3323-3328.
Patzlaff A, Newman LJ, Dubos C, Whetten RW, Smith C, McInnis S, Bevan MW, Sederoff RR, Campbell MM (2003) Characterization of PtMYB1, an R2R3-MYB from pine xylem. Plant Molecular Biology 53:597-608.
Rouster J, Leah R, Mundy J, Cameron-Mills V (1997) Identification of a methyl jasmonate-responsive region in the promoter of a lipoxygenase 1 gene expressed in barley grain. Plant Journal 11:513-523.
Sambrook J, Russell DW (2001) Molecular cloning: a laboratory manual, 3rd edn. Cold Spring Harbor Laboratory Press, New York, pp. 6.50-6.57.
Tai T, Tanksley S (1990) A rapid and inexpensive method for isolation of total DNA from dehydrated plant tissue. Plant Molecular Biology Reporter 8: 297-303.
Winzell A, Aspeborg H, Wang Y, Ezcurra I (2010) Conserved CA-rich motifs in gene promoters of Pt x tMYB021-responsive secondary cell wall carbohydrate-active enzymes in Populus. Biochemical and Biophysical Research Communications 394:848-853.
Wu X-F, Wang C-L, Xie E-B, Gao Y, Fan Y-L, Liu P-Q, Zhao K-J (2009) Molecular cloning and characterization of the promoter for the multiple stress-inducible gene BjCHI1 from Brassica juncea. Planta 229:1231-1242.
Yamamoto S, Nakano T, Suzuki K, Shinshi H (2004) Elicitor-induced activation of transcription via W box-related cis-acting elements from a basic chitinase gene by WRKY transcription factors in tobacco. Biochimica et Biophysica Acta 1679:279-287.
Yin Y, Chen L, Beachy R (1997) Promoter elements required for phloem-specific gene expression from the RTBV promoter in rice. Plant Journal 12:1179-1188.
NCBI , GenBank accession No. AY781896.1 (Aug. 14, 2009), 2 pages.
International Search Report and Written Opinion, PCT/US2015/019768, dated Jun. 3, 2015, 12 pages.
U.S. Appl. No. 61/612,744, titled: Compositions, Organisms, Systems, and Methods for Expressing a Gene Product in Plants, filed Mar. 19, 2012, 79 pages.
Jefferson R, Kavanagh T, Bevan M (1987) GUS fusions: β-glucuronidase as a sensitive and versatile gene fusion marker in higher plants. The EMBO Journal vol. 6, No. 13, pp. 3901-3907.
Pearson W, (1990) Rapid Sequence Comparison: Rapid and Sensitive Sequence Comparison with FASTP and FASTA. Methods in Enzymology, vol. 183, 36 pages.
Pearson W, Lipman D, (1988) Improved tools for biological sequence comparison. Proc. Natl. Acad. Sci., vol. 85, pp. 2444-2448.

\* cited by examiner

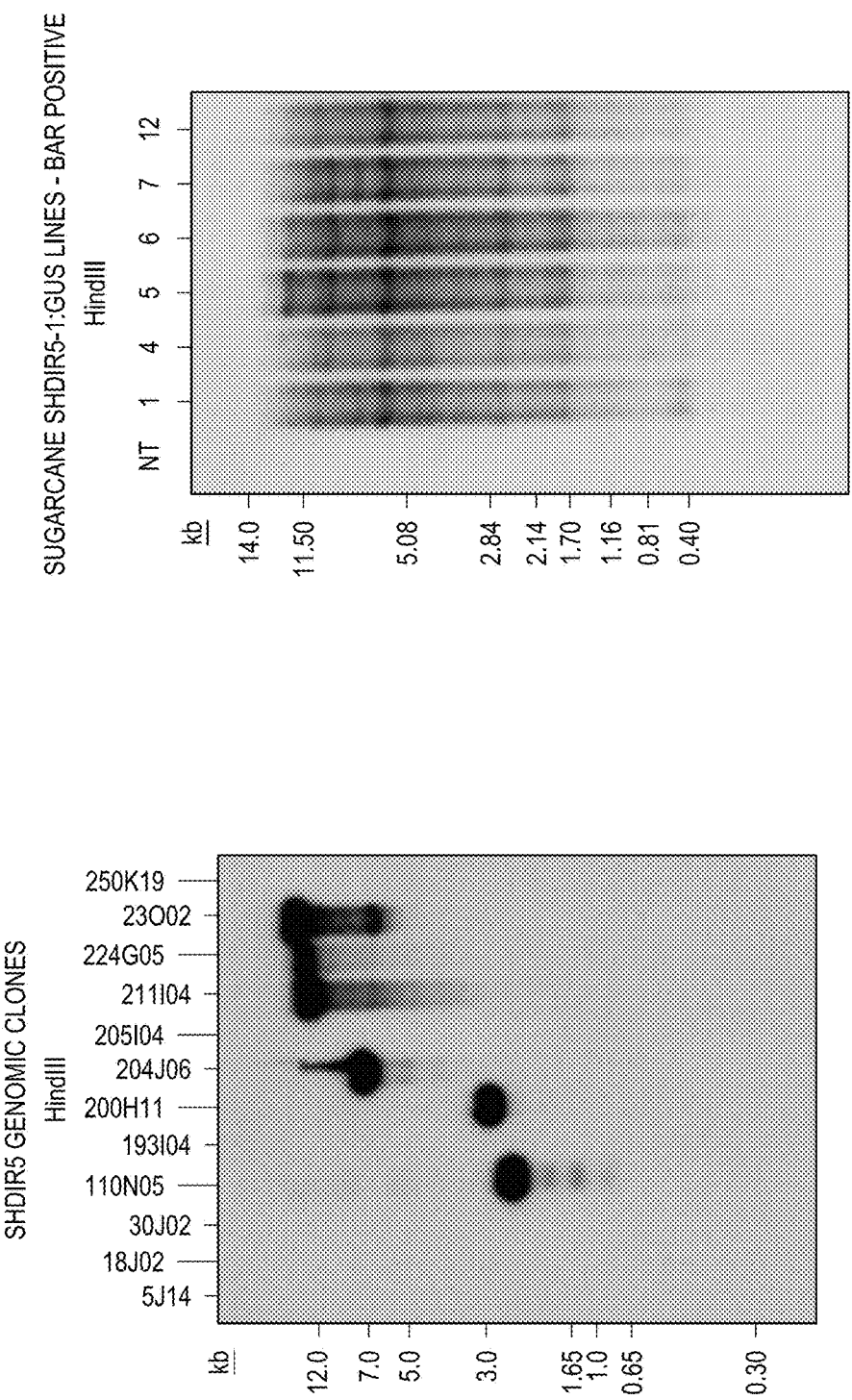

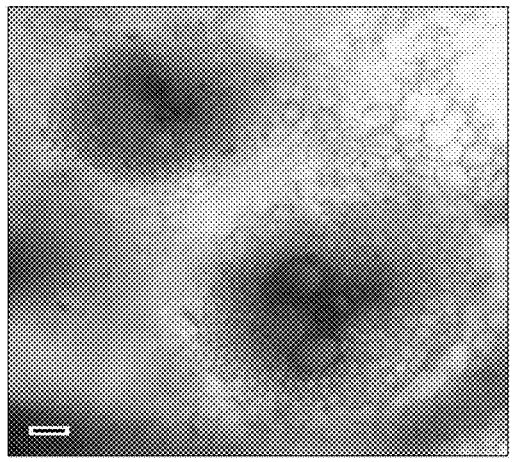
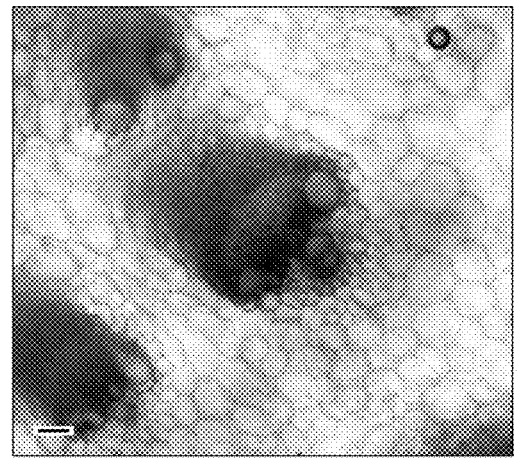
FIG. 13A                FIG. 13B
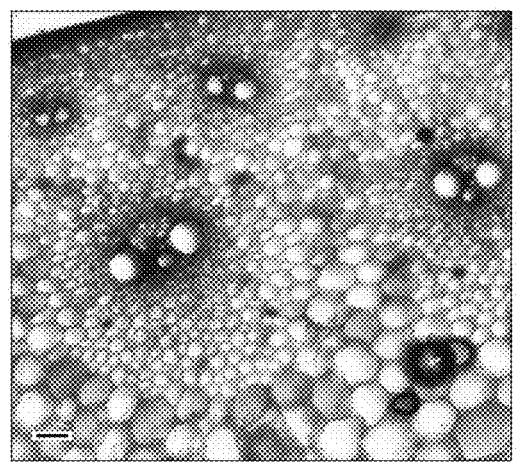
FIG. 13C

STEM-SPECIFIC PROMOTER FROM SUGARCANE DIRIGENT GENE

RELATED APPLICATIONS

This application claims priority to U.S. Provisional Application No. 61/950,599 filed Mar. 10, 2014 and U.S. Provisional Application No. 61/950,788 filed Mar. 10, 2014, the entire contents of which are hereby incorporated in their entirety by this reference.

FIELD OF THE DISCLOSURE

The present disclosure relates, in some embodiments, to compositions, organisms, systems, and methods for expressing a gene product in a plant (e.g., a monocot) using a promoter operable in one or more plant tissues.

BACKGROUND OF THE DISCLOSURE

Biotechnology promises to revolutionize everything from agriculture to modem medicine. For example, methods of genetically engineering plants are being explored to increase productivity through greater drought and insect resistance, as well as, increased yields. In addition, plants are being examined as potential biofactories for the production of proteins (e.g., antibodies) and other compounds for use in human and veterinary medicine. However, a limited number of expression control sequences (e.g., promoters) exist for driving expression of a gene product of interest in plants. Some of these are effective at driving expression in only some plants. Others are effective at driving expression in some tissues and/or cells, but not others.

SUMMARY

Accordingly, a need has arisen for expression control sequences (e.g., promoters) operable in plants including promoters that are operable in monocots and/or promoters that are operable in one or more plant tissues and/or cells.

The present disclosure relates, according to some embodiments, to compositions, organisms, systems, and methods for expressing a gene product in a plant (e.g., a monocot) using a promoter operable in one or more plant tissues and/or cells. In some embodiments, an artificial nucleic acid may comprise an expression control sequence having a sequence selected from the sequence of nucleotides 1-4710 of SEQ ID NO: 1 and the sequence of nucleotides 1137-4710 of SEQ ID NO: 1, wherein the expression control sequence has stem-specific promoter activity in at least one monocot (e.g., at least two monocots).

The present disclosure relates, in some embodiments, to an artificial nucleic acid comprising (a) an expression control sequence having a sequence selected from the sequence of nucleotides 1-4710 of SEQ ID NO: 1 and the sequence of nucleotides 1137-4710 of SEQ ID NO: 1, and (b) an exogenous nucleic acid (e.g., a transgene), wherein the expression control sequence has stem-specific promoter activity in at least one monocot. In some embodiments, an expression control sequence may be modified by a single deletion of a single nucleotide, a single insertion of a single nucleotide, or a single substitution of a single nucleotide. An exogenous nucleic acid may alter carbon metabolism in the plant cell when expressed or transcribed in some embodiments. An exogenous nucleic acid may encode, in some embodiments, an insecticide effective against at least one stem-boring insect.

According to some embodiments, the present disclosure relates to an expression vector comprising, in a 5' to 3' direction: a sugarcane dirigent promoter having a nucleotide sequence selected from the sequence of nucleotides 1-4710 of SEQ ID NO: 1 and the sequence of nucleotides 1137-4710 of SEQ ID NO: 1; an exogenous nucleic acid (e.g., a transgene); and a 3' termination sequence, wherein the sugarcane dirigent promoter has stem-specific promoter activity in at least one monocot. An expression vector may be located in a bacterial cell or a plant cell. In some embodiments, a nucleotide sequence of a sugarcane dirigent promoter may be modified by a single deletion of a single nucleotide, a single insertion of a single nucleotide, or a single substitution of a single nucleotide.

The present disclosure relates, in some embodiments, to a bacterial cell comprising an expression vector having: (a) a sugarcane dirigent promoter having a nucleotide sequence selected from the sequence of nucleotides 1-4710 of SEQ ID NO: 1 and the sequence of nucleotides 1137-4710 of SEQ ID NO: 1; (b) an exogenous nucleic acid; and (c) a 3' termination sequence, wherein the sugarcane dirigent promoter has stem-specific promoter activity in at least one monocot in some embodiments.

The present disclosure further relates to a plant cell comprising an expression vector, in some embodiments, the expression vector comprising (a) a promoter having a nucleotide sequence selected from the sequence of nucleotides 1-4710 of SEQ ID NO: 1 and the sequence of nucleotides 1137-4710 of SEQ ID NO: 1; (b) an exogenous nucleic acid (e.g., a transgene) operably linked to the promoter; and (c) a 3' termination sequence operably linked to the exogenous nucleic acid, wherein the promoter has stem-specific promoter activity in at least one monocot. An exogenous nucleic acid may alter carbon metabolism in the plant cell when expressed or transcribed in some embodiments. An exogenous nucleic acid may encode, in some embodiments, an insecticide effective against at least one stem-boring insect. A plant cell comprising an expression vector may be located in a plant (e.g., a monocot) in some embodiments. Examples of a plant may include sugarcane, *miscanthus*, a *miscanthus*×sugarcane hybrid, switch grass, oat, wheat, barley, maize, rice, banana, *yucca*, onion, asparagus, *sorghum* and hybrids thereof. In some embodiments, a nucleotide sequence of a promoter may be modified by a single deletion of a single nucleotide, a single insertion of a single nucleotide, or a single substitution of a single nucleotide.

According to some embodiments, the present disclosure relates to plants comprising an expression vector having: (a) a promoter having a nucleotide sequence selected from the sequence of nucleotides 1-4710 of SEQ ID NO: 1 and the sequence of nucleotides 1137-4710 of SEQ ID NO: 1; (b) an exogenous nucleic acid operably linked to the promoter; and (c) a 3' termination sequence operably linked to the exogenous nucleic acid, wherein the promoter has stem-specific promoter activity in at least one monocot.

The present disclosure is related to nucleotide and/or amino acid sequences that are either (i) not found anywhere in nature or (ii) not found in nature in the organism into which they have been introduced.

In addition, the present disclosure relates to methods for stem-specifically expressing an exogenous nucleic acid in a monocot, in some embodiments. For example, a method may comprise contacting an expression cassette or expression vector with the cytosol of a cell of the monocot, wherein the expression cassette or expression vector comprises (i) the exogenous nucleic acid, (ii) a sugarcane dirigent promoter comprising the sequence selected from the sequence of nucleotides 1-4710 of SEQ ID NO: 1 and the sequence of nucleotides 1137-4710 of SEQ ID NO: 1, and (iii) a 3' termination sequence operably linked to the exogenous nucleic acid, wherein the sugarcane dirigent promoter is operable to drive expression of the exogenous nucleic acid in the monocot, and wherein the promoter has stem-specific promoter activity in the monocot. In some embodiments, contacting further comprises biolistically bombarding the cell with a particle comprising the expression cassette or expression vector and/or co-cultivating the cell with an *Agrobacterium* cell comprising the expression cassette or expression vector. Plants in which an exogenous gene may be expressed include sugarcane, *miscanthus*, a *miscanthus*× sugarcane hybrid, switch grass, oat, wheat, barley, maize, rice, banana, *yucca*, onion, asparagus, *sorghum* and hybrids thereof.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

Some embodiments of the disclosure may be understood by referring, in part, to the present disclosure and the accompanying drawings, wherein:

FIG. 3 illustrates a Southern blot analysis of HindIII digested DNA of twelve sugarcane SHDIR5 positive genomic clones, using SHDIR5 full-length cDNA as a probe according to a specific example embodiment of the disclosure;

FIG. 6 illustrates a genomic Southern blot analysis of HindIII digested genomic DNA from six sugarcane lines transgenic for the β-glucuronidase (GUS) gene under the control of a sugarcane dirigent 5-1 (SHDIR5-1) promoter according to a specific example embodiment of the disclosure;

FIG. 13A illustrates a micrograph of transgenic sugarcane stems showing histochemical localization of GUS gene expression driven by a SHDIR5-1 promoter in the vasculature and storage parenchyma of stem top section according to a specific embodiment of the disclosure;

FIG. 13B illustrates a micrograph of transgenic sugarcane stems showing histochemical localization of GUS gene expression driven by a SHDIR5-1 promoter in the vasculature and storage parenchyma of middle section according to a specific embodiment of the disclosure;

FIG. 13C illustrates a micrograph of transgenic sugarcane stems showing histochemical localization of GUS gene expression driven by a SHDIR5-1 promoter in the vasculature and storage parenchyma of stem bottom section according to a specific embodiment of the disclosure;

BRIEF DESCRIPTION OF THE SEQUENCE LISTING

Figure 1:
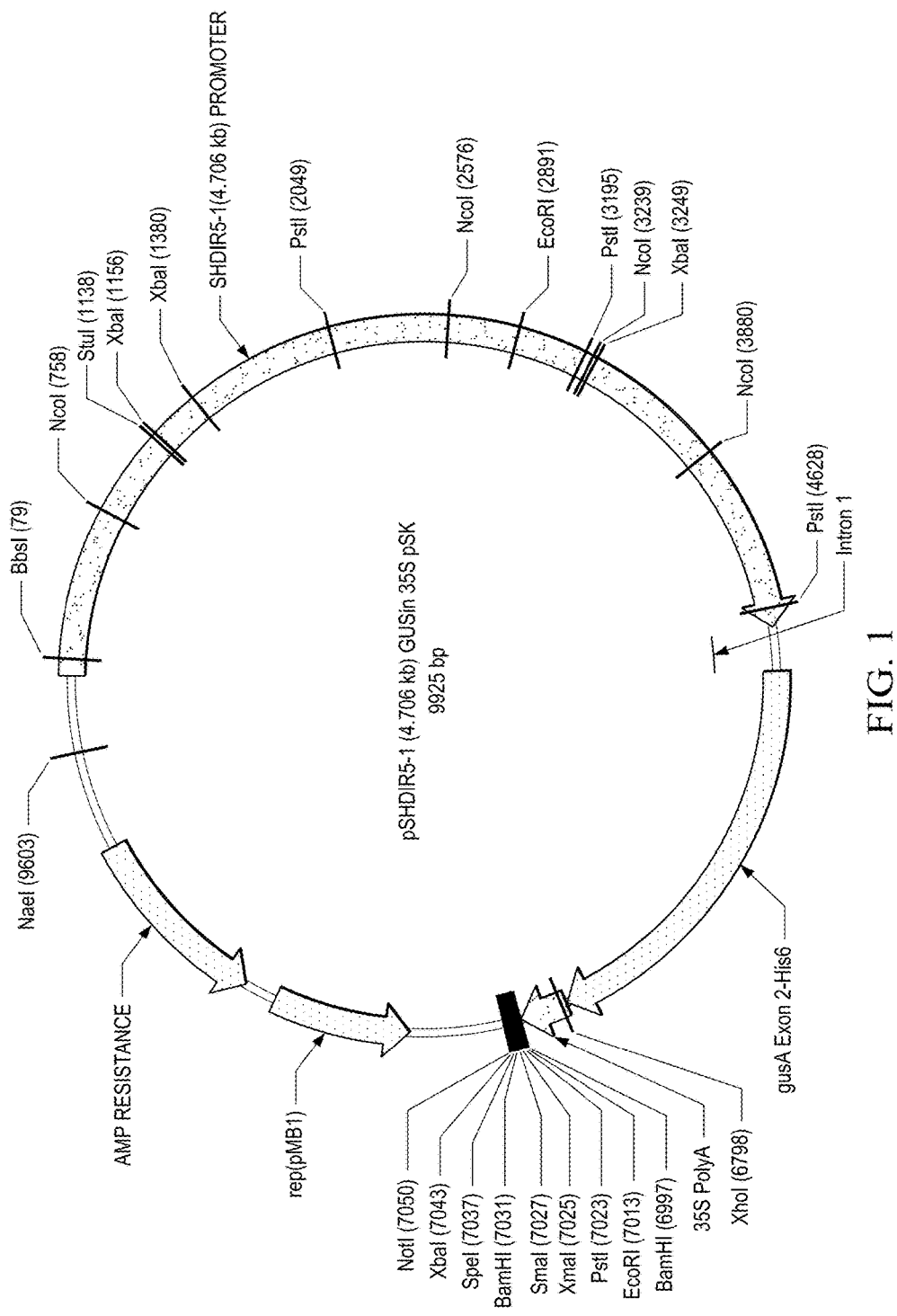
FIG. 1 illustrates a sugarcane dirigent 5-1 promoter (4.706 kb) β-glucuronidase expression pBluescript SK vector (pSHDIR5-1(4.706 kb)GUSin35SpSK) (SEQ ID NO: 8) suitable for expression in sugarcane according to a specific example embodiment of the disclosure.

Some embodiments of the disclosure may be understood by referring, in part, to the present disclosure and the accompanying sequence listing, wherein:

SEQ ID NO: 1 illustrates a sugarcane dirigent 5-1 (SHDIR5-1) promoter according to a specific example embodiment of the disclosure;

SEQ ID NO: 2 illustrates an expression cassette suitable for sugarcane transformation according to a specific example embodiment of the disclosure comprising a sugarcane dirigent 5-1 (SHDIR5-1) promoter, a β-glucuronidase (GUS) coding sequence, and an Agrobacterium nopaline synthase (NOS) terminator;

SEQ ID NO: 3 illustrates an expression cassette suitable for sugarcane transformation according to a specific example embodiment of the disclosure comprising a 3.574 kb sugarcane dirigent 5-2(SHDIR5-2) promoter, a β-glucuronidase (GUS) coding sequence, and an Agrobacterium nopaline synthase (NOS) terminator;

SEQ ID NO: 4 illustrates a sugarcane dirigent 5-1 (SHDIR5-1) protein according to a specific example embodiment of the disclosure;

SEQ ID NO: 5 illustrates a sugarcane FN95-1702 dirigent (DIR) 5' untranslated region (UTR) according to a specific example embodiment of the disclosure.

SEQ ID NO: 6 illustrates a sugarcane Q117 dirigent 5' UTR according to a specific example embodiment of the disclosure;

SEQ ID NO: 7 illustrates a sugarcane c67 dirigent 5' UTR according to a specific example embodiment of the disclosure;

SEQ ID NO: 8 illustrates an expression cassette suitable for sugarcane transformation according to a specific example embodiment of the disclosure comprising a 4.706 kb fragment of a sugarcane dirigent 5-1 (SHDIR5-1) promoter, a β-glucuronidase (GUS) coding sequence with a castorbean catalase intron and a hexa histidine tag, and 35S terminator (35S) of Cauliflower mosaic virus; and SEQ ID NO: 9 illustrates an expression cassette suitable for sugarcane transformation according to a specific example embodiment of the disclosure comprising a 3.574 kb sugarcane dirigent 5-2 (SHDIR5-2) promoter, a β-glucuronidase (GUS) coding sequence with a castorbean catalase intron and a hexa histidine tag, and 35S terminator (35S) of Cauliflower mosaic virus.

DETAILED DESCRIPTION

The present disclosure relates, according to some embodiments, to compositions, organisms, systems, and methods for expressing a gene product in a plant (e.g., a monocot) using a promoter operable in one or more plant tissues and/or cells. For example, the present disclosure relates to expression control sequences (e.g., promoters), expression cassettes, expression vectors, microorganisms, and/or plants comprising a sugarcane dirigent 5-1 (SHDIR5-1) promoter and/or a sugarcane dirigent 5-2 (SHDIR5-2) promoter. An expression control sequence, according to some embodiments, may be constitutively active or conditionally active in (a) an organ selected from root, leaf, stem, flower, seed, fruit, and/or tuber and/or (b) active in a tissue selected from epidermis, periderm, parenchyma, collenchyma, sclerenchyma, xylem, phloem, and/or secretory structures.

In some embodiments, an expression control sequence may be included in methods, compositions, systems, and/or organisms (a) to alter carbon metabolism (e.g., in a sucrose accumulating tissue) and/or (b) to express a protein (e.g., an insecticidal protein) in a plant (e.g., in sugarcane). An expression control sequence may be included, according to some embodiments, in methods, compositions, systems, and/or organisms to improve pest and/or disease tolerance and/or disease resistance (e.g., rice plants).

The disclosure, in some embodiments, relates to an expression control sequence operable in monocots (e.g., sugarcane, sorghum, maize, rice) to drive expression in one or more tissues (e.g., stem tissue). For example, an expression control sequence may comprise an isolated promoter of sugarcane that regulates expression of a gene for sugarcane dirigent 5-1 (SHDIR5-1) protein. SHDIR5-1 protein may be involved in lignification and/or plant defense responses in some embodiments. An SHDIR5-1 expression control sequence may be stem-expressed according to some embodiments. In some embodiments an SHDIR5-2 expression control sequence may be stem-expressed. An SHDIR5-1 expression control sequence may comprise a 4.710 kb nucleic acid region, which may be located upstream of the 5' end of a sugarcane SHDIR5-1 structural coding sequence, and may be capable of driving high levels of gene and/or transgene expression in a stem-regulated manner in one or more plants (e.g., major agronomic crops such as sugarcane and rice). In some embodiments an SHDIR5-2 expression control sequence may comprise a 3.574 kb nucleic acid region, which may be located upstream of the 5' end of a sugarcane SHDIR5-1 structural coding sequence, and may be capable of driving high levels of gene and/or transgene expression in a stem-regulated manner in one or more plants (e.g., major agronomic crops such as sugarcane and rice). In some embodiments the term SHDIR5 expression control sequence may be used to refer either an SHDIR5-1 expression control sequence or an SHDIR5-2 expression control sequence.

According to some embodiments, a distinguishing feature of an expression control sequence over expression control sequences having a similar nucleic acid sequence may be operable in various organisms. For example, a first expression control sequence may be operable in as few as one species (e.g., the species from which it was originally isolated), whereas a second expression control sequences may be operable in two or more species. Operability may be assessed according to a variety of metrics including total transcript produced, total protein produced, cell and/or tissue types in which transcript is produced, cell and/or tissue types in which protein is produced, inducibility, among others. For example, some functional stem-expressed promoters may be available for use in transformation of sugarcane, an economically important crop, in terms of sucrose accumulation and biomass production. Such promoters may not be operable in a broader range of species, tissues, and/or cell types.

A finite number of expression control sequences are known to be operable in monocots (e.g., sugarcane, *sorghum*, maize, rice). Expression control sequences, according to the present disclosure, may supplement, complement, expand, and/or overcome perceived limits of the existing pool of monocot-operable expression control sequences. For example, expression control sequences, according to the present disclosure, may have one or more desirable features over other expression control sequences in regulating gene and/or transgene expression in the stem vasculature and/or storage parenchyma tissues.

Choice of an expression control sequence may influence (e.g., determine) when and/or where a gene of interest (operably linked to the expression control sequence) is expressed in a plant. The tissue-regulated expression conferred by a SHDIR5-1 promoter and/or a SHDIR5-2 promoter may be particularly important in maximizing metabolic energy into gene and/or transgene products at target sites, thereby reducing the impact on non-target tissues. A SHDIR5-1 promoter and/or SHDIR5-2 promoter may be of value in engineering monocots for improved carbon metabolism for sugar accumulation and/or high fiber content for biofuel feedstock and bioenergy production, as well as for enhanced stress tolerance. In some embodiments the term SHDIR5 promoter may be used to refer to a SHDIR5-1 promoter and/or a SHDIR5-2 promoter.

The present disclosure is related to nucleotide and/or amino acid sequences that are either (i) not found anywhere in nature or (ii) not found in nature in the organism into which they have been introduced.

The present disclosure relates, in some embodiments, to artificial nucleic acids. An artificial nucleic acid may have a sequence that is similar, but not identical, to a sequence that is found to occur naturally. An artificial sequence may be similar to a sequence that is found to occur naturally, but may be modified by at least one insertion of at least one nucleotide, at least one deletion of at least one nucleotide, at least one substitution of at least one nucleotide, or any combination thereof.

According to some embodiments, the present disclosure provides nucleic acid sequences and constructs, expression vectors, plant cells and transgenic plants comprising an SHDIR5-1 promoter or an SHDIR5-2 promoter. In some embodiments, transgenic plants (e.g., sugarcane, *sorghum*, maize, rice) may include a coding sequence that is operably linked to a SHDIR5-1 promoter or an SHDIR5-2 promoter. In some embodiments, a transgenic plant may include a nucleic acid having a coding sequence heterologous to the transgenic plant (e.g., an exogenous coding sequence, a transgene, an artificial sequence). In some embodiments, where a transgenic plant is a monocot other than sugarcane, a coding sequence may be heterologous or non-heterologous to the transgenic plant species. In some embodiments, expression of a coding sequence may be directed by a SHDIR5-1 and/or a SHDIR5-2 promoter, may occur in stem tissues, and/or may be substantially limited to stem tissues, in each case, under at least some growth conditions. The disclosure relates, in some embodiments, to methods for producing nucleic acid vectors, expression cassettes and transgenic plants.

An SHDIR5-1 expression control sequence and/or an SHDIR5-2 expression control sequence (e.g., promoter) may provide, in some embodiments, tight regulation of gene expression in stem tissues. According to some embodiments, an SHDIR5-1 expression control sequence and/or an SHDIR5-2 expression control sequence may be inactive or substantially inactive in one or more (e.g., all) non-stem tissues of a plant. An expression control sequence (e.g., promoter) may drive expression of one or more genes/transgenes of interest at desirable levels and/or in desired target tissue(s). Regulated expression of genes and/or transgenes may ensure plant productivity, viability and/or fertility, for example, when constitutive expression of a gene/transgene is likely to compromise metabolism or important aspects of meristem or embryo function. Tissue-regulated expression may be desirable for increasing (e.g., maximizing) metabolic energy into gene/transgene products at target sites, thereby reducing the impact on non-target tissues. According to some embodiments, an SHDIR5 expression control sequence (e.g., promoter) may be less susceptible to silencing in one or more monocots than one or more existing stem-specific promoters. An SHDIR5-1 expression control sequence or an SHDIR5-2 expression control sequence (e.g., promoter) may operate in one or more monocots including monocot crops (e.g., sugarcane, *sorghum*, maize, and rice).

According to some embodiments, the present disclosure relates to expression control sequences (e.g., regulatory sequences) operable to direct stem-regulated and/or defense-inducible expression. An expression control sequence may include promoters from a stem-expressed, defense-inducible family of genes (e.g., dirigent 5 (SHDIR5) genes). Expression control sequences, in some embodiments, may have specific advantages over other tissue-specific expression control sequences (e.g., promoters) in their enhanced specificity in regulating gene expression (a) in stem tissues and/or (b) in response to induction by external stimuli such as plant defense-inducing agents. Expression control sequences according to some embodiments of the disclosure may be very useful in methods for altering carbon metabolism in sucrose accumulating tissues and/or for driving expression of desired proteins (e.g., insecticidal proteins) in sugarcane. An expression control sequence (e.g., promoter) may also be included in methods of improved pest and/or disease tolerant plants (e.g., rice plants) in some embodiments.

The present disclosure relates to artificial nucleic acids, according to some embodiments, including promoters operable (e.g., primarily) in stem and/or in response to stimulation by defense-inducing agents. An expression control sequence (e.g., promoter) may hybridize (e.g., under stringent conditions) to an expression control sequence isolated from sugarcane (e.g., an SHDIR5-1 promoter).

Expression Control Sequences

The disclosure relates, in some embodiments, to artificial nucleic acids including expression control sequences operable to direct stem-regulated and/or defense-inducible expression. The present disclosure relates, in some embodiments, to artificial nucleic acids comprising expression control sequences (e.g., promoters) capable of specifically directing expression in stem tissue and/or in response to stimulation by defense-inducing agents. For example, an expression control sequence (e.g., promoter), when operably linked to either a coding sequence of a gene or a sequence complementary to a native plant gene, may direct expression of the coding sequence or complementary sequence in stem tissue and/or in response to a defense-inducing agent.

In some embodiments, an SHDIR5 expression control sequence may be provided by screening a library of nucleic acids (e.g., a monocot genomic library) using an SHDIR5-1 nucleic acid, an SHDIR5-2 nucleic acid, a fragment thereof, and/or a complement thereto as a probe. For example, an SHDIR5-1 promoter may be provided as follows. SHDIR5-1 recombinant genomic clones may be first isolated by screening a sugarcane genomic library constructed in a bacterial artificial chromosome with a cDNA (or a portion thereof) representing SHDIR5-1 mRNA. To obtain a cDNA representing SHDIR5-1 mRNA, a sugarcane stem-regulated cDNA library may be constructed and screened by differential hybridization with stem, leaf and root cDNA probes to identify stem-regulated cDNAs including the SHDIR5-1 cDNA. Sequences identical, similar, and/or homologous to SHDIR5-1 may be isolated using established cloning techniques and/or amplification techniques.

In some embodiments, an SHDIR5-1 expression control sequence and/or an SHDIR5-2 expression control sequence (e.g., promoter) may be derived from restriction endonuclease digestion of isolated SHDIR5-1 genomic clones. For example, the nucleotide or amino acid sequence of the coding region of a gene of the sugarcane dirigent (SHDIR) gene family may be aligned to the nucleic acid or deduced amino acid sequence of an isolated stem-regulated genomic clone and the 5' flanking sequence (i.e., sequence upstream from the translational start codon of the coding region) of the isolated SHDIR5-1 genomic clone may be located. An SHDIR5-1 expression control sequence (e.g., promoter) as set forth in SEQ ID NO: 1 may be generated, according to some embodiments, from genomic clones having either or both excess 5' flanking sequence or coding sequence by exonuclease III-mediated deletion. This may be accomplished by digesting appropriately prepared DNA with exonuclease III (exoIII) and removing aliquots at increasing intervals of time during the digestion. The resulting successively smaller fragments of DNA may be sequenced to determine the exact endpoint of the deletions. Commercially available systems which use exonuclease III (exoIII) to create such a deletion series may include Promega Biotech, "Erase-A-Base"® system. Alternatively, PCR primers may be defined to allow direct amplification of an SHDIR5-1 expression control sequence (e.g., promoter). It will be understood by one having skill in the art that one or more deletion fragments of an SHDIR5-1 expression control sequence (e.g., SHDIR5-2 (1137-4710 SEQ ID NO:1)) may be prepared using the same or similar methods. An expression control sequence may comprise at least one contiguous portion of the nucleotide sequences set forth in SEQ ID NO: 1 and/or may be operable to direct stem-regulated and/or defense-inducible expression according to some embodiments. A deletion fragment may comprise one or more nucleotides (e.g., contiguous nucleotides).

An expression control sequence may include, in addition to a sugarcane SHDIR5-1 promoter having the nucleotide sequence of SEQ ID NO: 1 or a fragment thereof, sequences which correspond to the same gene, i.e., a homolog, in other plant species. Such related sequences which direct stem-regulated and/or defense-inducible expression, may be described in terms of their percent homology and/or identity on a nucleotide level to the nucleotide sequence of SEQ ID NO: 1 in some embodiments. Such related sequences from other plant species may be defined in terms of their ability to hybridize to a nucleic acid having a nucleotide sequence of SEQ ID NO: 1 (or a fragment thereof larger than about 1 kb) under stringent hybridization conditions.

In some embodiments, an expression control sequence may comprise one or more promoters, one or more operators, one or more enhancers, one or more ribosome binding sites, and/or combinations thereof. An expression control sequence may comprise, for example, a nucleic acid (a) operable to direct stem-regulated and/or defense-inducible expression in one or more monocots including monocot crops (e.g., sugarcane, *sorghum*, maize, and rice) and (b) having a nucleotide sequence more than about 70% identical to SEQ ID NO: 1, more than about 75% identical to SEQ ID NO: 1, more than about 80% identical to SEQ ID NO: 1, more than about 81% identical to SEQ ID NO: 1, more than about 82% identical to SEQ ID NO: 1, more than about 83% identical to SEQ ID NO: 1, more than about 84% identical to SEQ ID NO: 1, more than about 85% identical to SEQ ID NO: 1, more than about 86% identical to SEQ ID NO: 1, more than about 87% identical to SEQ ID NO: 1, more than about 88% identical to SEQ ID NO: 1, more than about 89% identical to SEQ ID NO: 1, more than about 90% identical to SEQ ID NO: 1, more than about 92% identical to SEQ ID NO: 1, more than about 94% identical to SEQ ID NO: 1, more than about 96% identical to SEQ ID NO: 1, more than about 98% identical to SEQ ID NO: 1, more than about 98.5% identical to SEQ ID NO: 1, more than about 99% identical to SEQ ID NO: 1, and/or more than about 99.5% identical (e.g., 100% identical) to SEQ ID NO: 1. For example, an artificial nucleic acid may comprise an expression control sequence (e.g., promoter) isolated from sugarcane having the sequence of nucleotides 1 to 4710 of SEQ ID NO:1. According to some embodiments, sequences that are not 100% identical over the full length of SEQ ID NO: 1 may have points and/or regions of variation that are dispersed (e.g., uniformly, haphazardly, randomly) over the length of the subject nucleic acid. For example, an expression control sequence may comprise one or more regions of sequence that are 100% identical to SEQ ID NO: 1 (e.g., in or near a TATA-box, a CCAAT-box, a TSS-motif, and/or one or more of the motifs in Table 5) and one or more regions that are less than 100% identical length and/or sequence. An expression control sequence in some embodiments, may comprise a nucleic acid having a nucleotide sequence that is about 100% identical to a 5' untranslated region (UTR) of FN95-1702 dirigent (DIR) (SEQ ID NO: 5) and nucleotides 4664-4710 of SHDIR5-1 (SEQ ID NO: 1) or about 100% identical to a 5' UTR of Q117 dirigent (SEQ ID NO; 6) and nucleotides 4664-4710 of SHDIR5-1 (SEQ ID NO: 1), or about 100% identical to a 5' UTR of c67 dirigent (SEQ ID NO: 7) and nucleotides 4664-4710 of SHDIR5-1 (SEQ ID NO: 1).

According to some embodiments, an expression control sequence may comprise, for example, a nucleic acid having a nucleic acid sequence of SEQ ID NO: 1. In some embodiments, an expression control sequence may comprise, for example, a nucleic acid having a nucleic acid sequence of nucleotides 1137-4710 of SEQ ID NO: 1. According to some embodiments, an expression control sequence may comprise, for example, a nucleic acid having the nucleotide sequence of SEQ ID NO: 1 modified by a single deletion of a single nucleotide, a single insertion of a single nucleotide, or a single substitution of a single nucleotide. In some embodiments, an expression control sequence may comprise, for example, a nucleic acid having the nucleotide sequence of nucleotides 1137-4710 of SEQ ID NO: 1 modified by a single deletion of a single nucleotide, a single insertion of a single nucleotide, or a single substitution of a single nucleotide. It will be understood by one skilled in the art that where the designations "SHDIR5-1 promoter" or "SHDIR5-2 promoter" are used in the present description, use of other nucleic acids having similar hybridization characteristics, expression characteristics, and/or sequence identity, as set forth herein may be substituted. According to some embodiments, expression control sequences (e.g., less than 100% identical to SEQ ID NO: 1) retain some ability to direct stem-specific transcription and/or defense-inducible transcription in at least one monocot (e.g., sugarcane, *sorghum*, maize, rice).

A number of algorithms, often implemented on a computer, are available to compare and align nucleic acid sequences which one skilled in the art may use for purposes of determining sequence identity (sequence similarity) including, for example, the Basic Local Alignment Search Tool (BLAST), ClustalW, ClustalX, FASTA, LALIGN, GGSEARCH, and/or GLSEARCH. For example, sequences similar to a subject expression control sequence (e.g., promoter) may be identified, according to some embodiments, by database searches using the expression control sequence (e.g., promoter) or elements thereof as the query sequence with a sequence search/alignment algorithm (e.g., the Gapped BLAST algorithm (Altschul et al., 1997 *Nucl. Acids Res.* 25:3389-3402) with the BLOSUM62 Matrix, a gap cost of 11 and persistence cost of 1 per residue and an E value of 10.) Two sequences may be compared with either ALIGN (Global alignment) or LALIGN (Local homology alignment) in the FASTA suite of applications (Pearson and Lipman, 1988 *Proc. Nat. Acad. Sci.* 85:2444-24448; Pearson, 1990 *Methods in Enzymology* 183:63-98) with the BLOSUM50 matrix and gap penalties of −16, −4.

A nucleic acid comprising an expression control sequence, in some embodiments, may hybridize with the SHDIR5-1 nucleic acid sequence as set forth in FIG. 1 (SEQ ID NO: 1), may differ in one or more positions in comparison with SEQ ID NO: 1, and/or may be operable to direct stem-regulated and/or defense-inducible expression in at least one monocot. Hybridization may include conventional nucleic acid hybridization conditions, which may be stringent. Stringent hybridization conditions may include, for example, (a) hybridization in 4×saline sodium citrate (SSC) at 65° C., followed by washing in 0.1×SSC at 65° C. for one hour and/or (b) hybridization in 50% formamide, 4×SSC at 42° C.

In some embodiments, stem-specificity and/or defense-inducibility of an expression control sequence may be confirmed by constructing transcriptional and/or translational fusions of a test sequence with a coding sequence of a heterologous gene and/or coding sequence (e.g. an exogenous coding sequence, a transgene), transferring the resulting fusion (e.g., in an expression cassette) into an appropriate host, and detecting expression of the heterologous gene and/or coding sequence. The detected expression may be compared to a corresponding fusion with SEQ ID NO: 1 and/or a modified version thereof. The assay used to detect expression depends upon the nature of the heterologous gene and/or coding sequence. For example, reporter genes (e.g., chloramphenicol acetyl transferase, β-glucuronidase (GUS), green fluorescent protein (GFP)) may be used to assess transcriptional and translational competence of chimeric nucleic acids. Standard assays are available to sensitively detect reporter enzymes in a transgenic organism.

The GUS gene is useful as a reporter of expression control sequence (e.g., promoter) activity in transgenic plants because of the high stability of the enzyme in plant cells, the lack of intrinsic GUS activity in higher plants, and availability of a quantitative fluorimetric assay and a histochemical localization technique. Jefferson et al. (*EMBO Journal* 6:3901-3907, 1987) have established standard procedures for biochemical and histochemical detection of GUS activity in plant tissues. Biochemical assays may be performed by mixing plant tissue lysates with 4-methylumbelliferyl-β-D-glucuronide, a fluorometric substrate for GUS, incubating one hour at 37° C., and then measuring the fluorescence of the resulting 4-methyl-umbelliferone. Histochemical localization for GUS activity is determined by incubating plant tissue samples in 5-bromo-4-chloro-3-indolyl-glucuronide (X-Gluc) for about 18 hours at 37° C. and observing the staining pattern of X-Gluc. Construction of such expression cassettes may allow definition of specific regulatory sequences and may demonstrate that a test sequence can direct expression of heterologous genes, and/or coding sequences in a stem-regulated and/or defense-inducible manner.

Expression Cassettes and Vectors

The disclosure relates, in some embodiments, to expression vectors and/or expression cassettes for expressing a nucleic acid sequence (e.g., a coding sequence) in a cell and comprising an expression control sequence and the nucleic acid sequence operably linked to the expression control sequence. A cassette, in some embodiments, may include a nucleotide sequence capable of expressing a particular coding sequence inserted so as to be operably linked to one or more expression control sequences present in the nucleotide sequence. Thus, for example, an expression cassette may include a heterologous coding sequence which is desired to be expressed in one or more plant cells, plant tissues, and/or one or more plant organs up to and including a whole plant, according to some embodiments. In some embodiments, an expression cassette may comprise an expression control sequence operable to direct stem-regulated and/or defense-inducible expression of a nucleic acid sequence (e.g., a coding sequence).

An expression control sequence (e.g., promoter), according to some embodiments, may be useful in the construction of an expression cassette comprising, in a 5' to 3' direction, the expression control sequence (e.g., SHDIR5-1, SHDIR5-2), a nucleic acid having a desired sequence for expression (e.g., a coding sequence, an antisense sequence, a heterologous gene), and/or sequence complementary to a native plant gene (e.g., under control of the expression control sequence), and/or a 3' termination sequence. In some embodiments, an expression cassette may be operable to facilitate and/or drive expression of a nucleic acid having a desired sequence (e.g., a bioinsecticidal peptide and/or a defense elicitor peptide) for expression in a stem-regulated and/or defense-inducible manner. According to some embodiments, an expression cassette may comprise, in a 5' to 3' direction, two or more expression control sequences (e.g., tandem copies of SHDIR5-1, tandem copies of SHDIR5-2, SHDIR5-1 in tandem with SHDIR5-2, SHDIR5-1 in tandem with another expression control sequence, another expression control sequence in tandem with SHDIR5-1), a nucleic acid having a desired sequence for expression, and (optionally) one or more termination sequences.

An expression cassette may be constructed by ligating an expression control sequence (e.g., SHDIR5-1, SHDIR5-2, and/or a portion thereof) to a coding sequence of a heterologous gene. Juxtaposition of these sequences may be accomplished in a variety of ways. In one embodiment, the sequences may be ordered in a 5' to 3' direction expression control sequence, desired sequence for expression, and optionally, a termination sequence (e.g., including a polyadenylation site).

An expression cassette may be incorporated into a variety of autonomously replicating vectors in order to construct an expression vector according to some embodiments. Standard techniques known to those of ordinary skill in the art for construction of an expression cassette may be used. A variety of strategies are available for ligating fragments of DNA, the choice of which depends on the nature of the termini of the DNA fragments.

Restriction and/or deletion fragments that contain an expression control sequence (e.g., promoter) TATA box may be ligated, according to some embodiments, in a forward orientation to a promoterless heterologous gene and/or a coding sequence, for example, a coding sequence of GUS. In some embodiments, an expression control sequence (e.g., promoter) may be prepared, for example, by chemical and/or enzymatic synthesis.

A 3' end of a heterologous coding sequence may be optionally ligated to a termination sequence including a polyadenylation site (e.g., a nopaline synthase polyadenylation site, and/or an octopine T-DNA gene 7 polyadenylation site). Alternatively, a polyadenylation site may be included in a heterologous gene and/or a coding sequence.

According to some embodiments, the disclosure relates to an expression cassette, which may comprise, for example, a nucleic acid having an expression control sequence and a coding sequence (e.g. an exogenous coding sequence, a transgene) operably linked to the expression control sequence. An expression cassette may be comprised in an expression vector. A coding sequence, in some embodiments, may comprise any coding sequence expressible in at least one plant cell. For example, a coding sequence may comprise a human sequence (e.g., an antibody sequence), a non-human animal sequence, a plant sequence, a yeast sequence, a bacterial sequence, a viral sequence (e.g., plant virus, animal virus, and/or vaccine sequence), an artificial sequence, an antisense sequence thereof, a fragment thereof, a variant thereof, and/or combinations thereof. According to some embodiments, a coding sequence may comprise, a sugar transport gene and/or a sugar accumulation gene. Examples of sugar transport genes may include, without limitation, a disaccharide transporter (e.g., a sucrose transporter) and/or a monosaccharide transporter. A coding sequence may comprise, in some embodiments, a sequence encoding one or more gene products with insecticidal, antimicrobial, and/or antiviral activity. Examples of gene products that may have insecticidal activity, antimicrobial activity, and/or antiviral activity may include, without limitation, avidin, vegetative insecticidal proteins (e.g., Vip3A), insecticidal crystal proteins from *Bacillus thuringiensis* (e.g., Cry1, Cry1Ab, Cry2, Cry9), pea albumin (e.g., PA1b), hirsutellin A, lectins (e.g., snow drop lily lectin, garlic lectin, onion lectin), amylase inhibitors (e.g., alpha amylase inhibitor), arcelins (e.g., arcelins from beans), proteinase inhibitors, lysozymes (e.g., bovine lysozyme, human lysozyme, mollusk lysozyme), defensin, chitinase, β-1,3-glucanase, variants thereof, and/or combinations thereof. A coding sequence may comprise a sequence encoding an enzyme for forming and/or modifying a polymer according to some embodiments. Examples of enzymes for forming and/or modifying a polymer may include, without limitation, a polyhydroxyalkanoate synthases, 4-hydroxybutyryl-CoA transferases, variants thereof, and/or combinations thereof. In some embodiments, a coding sequence may comprise a sequence encoding one or more enzymes that hydrolyzes cellulose. Examples of enzymes that hydrolyze cellulose include, without limitation, cellulase, endoglucanases (e.g., endo β-1,4 glucanases), glucosidases (e.g., β glucosidase), hydrolases (e.g., β-1,4-glucan cellobiohydrolase), exocellulases, variants thereof, and/or combinations thereof. In some embodiments, a coding sequence may comprise a sequence encoding one or more enzymes that form and/or modify a sugar (e.g., sucrose, trehalose, sorbitol, fructan, fructose, tagatose, sucralose). Examples of enzymes that form and/or modify a sugar may include, without limitation, trehalose-6-phosphate synthase (TPS) and trehalose-6-phosphate phosphatase (TPP). According to some embodiments, a coding sequence may comprise a sequence encoding an enzyme for forming or modifying glycine betaine, a polyamine, proline, threhalose, a variant thereof, and/or combinations thereof. A coding sequence may comprise, in some embodiments, a start codon, an intron, and/or a translation termination sequence. According to some embodiments, a coding sequence may comprise one or more natural or artificial coding sequences (e.g., encoding a single protein or a chimera). According to some embodiments, an expression cassette may optionally comprise a termination sequence.

An expression control sequence may be used, in some embodiments, to construct an expression cassette comprising, in the 5' to 3' direction, (a) the expression control sequence (e.g., a SHDIR5-1 promoter, a SHDIR5-2 promoter), (b) a heterologous gene or a coding sequence (e.g. an exogenous coding sequence, a transgene), or sequence complementary to a native plant gene under control of the expression control sequence, and/or (c) a 3' termination sequence (e.g., a termination sequence comprising a polyadenylation site). Examples of expression cassettes may include, in some embodiments, SEQ ID NO: 2 and/or SEQ ID NO: 3 and/or SEQ ID NO: 8 and/or SEQ ID NO: 9. An expression cassette may be incorporated into a variety of autonomously replicating vectors in order to construct an expression vector. An expression cassette may be constructed, for example, by ligating an expression control sequence to a sequence to be expressed (e.g., a coding sequence).

Some techniques for construction of expression cassettes are well known to those of ordinary skill in the art. For example, a variety of strategies are available for ligating fragments of DNA, the choice of which depends on the nature of the termini of the DNA fragments. Restriction and/or deletion fragments that contain a subject promoter TATA box may be ligated in a forward orientation to a promoterless heterologous gene or coding sequence such as the coding sequence of GUS. An artisan of ordinary skill having the benefit of the present disclosure, an expression control sequence and/or portions thereof may be provided by other means, for example chemical or enzymatic synthesis.

A nucleic acid may comprise, in a 5' to 3' direction, an expression control sequence, a linker (optional), and a coding sequence according to some embodiments. A linker may be, in some embodiments, from about 1 nucleotide to about 200 nucleotides in length and/or may comprise one or more restriction sites. Expression level of a nucleic acid sequence (e.g., a coding sequence) operably linked to an expression control sequence may be influenced by the length and/or sequence of a linker and/or the 5' sequence of the coding sequence. For example, expression level may be influenced by the sequence from about the −4 position to about the +4 position, in which the −1 position defines the 3' end of the linker, if present, sequence and the +1 position defines the 5' end of the coding sequence. In some embodiments, a nucleic acid may comprise, in a 5' to 3' direction, an expression control sequence, a linker, and a coding sequence, wherein the sequence of positions −4 to +4 comprises a sequence selected from the sequence shown in Table 1. A nucleic acid may comprise, in a 5' to 3' direction, an expression control sequence and a coding sequence, wherein the junction sequence comprises a sequence selected from the sequences shown in Table 1 according to some embodiments. In some embodiments, a −3 to −1 sequence of AAA may be associated with higher (e.g., the highest) expression levels than other −3 to −1 sequences. A +1 to +4 sequence of ATGG may be associated with higher (e.g., the highest) expression levels than other +1 to +4 sequences (e.g., ATGC, ATGA, ATGT).

TABLE 1

Optional Junction Sequences

| | −4 | −3 | −2 | −1 | +1 | +2 | +3 | +4 |
|---|---|---|---|---|---|---|---|---|
| 1 | N | N | N | N | A | T | G | G/T |
| 2 | N | A/C | A/C | A/C | A | T | G | G |
| 3 | A/C | A/C | A/C | A/C | A | T | G | G |
| 4 | N | A | A | A | A | T | G | G |
| 5 | N | A | A | C | A | T | G | G |
| 6 | N | A | C | A | A | T | G | G |
| 7 | N | A | C | C | A | T | G | G |
| 8 | N | C | A | A | A | T | G | G |
| 9 | N | C | A | C | A | T | G | G |
| 10 | N | C | C | A | A | T | G | G |
| 11 | N | C | C | C | A | T | G | G |
| 12 | N | A | A | T | A | T | G | G |
| 13 | N | A | T | A | A | T | G | G |
| 14 | N | A | T | T | A | T | G | G |
| 15 | N | T | A | A | A | T | G | G |
| 16 | N | T | A | T | A | T | G | G |
| 17 | N | T | T | A | A | T | G | G |
| 18 | N | T | T | T | A | T | G | G |
| 19 | N | C | T | T | A | T | G | G |
| 20 | N | T | C | T | A | T | G | G |
| 21 | N | T | T | C | A | T | G | G |
| 22 | C | A | C | C | A | T | G | G |
| 23 | N | N | C | C | A | T | G | G |
| 24 | C | G | C | C | A | T | G | G |
| 25 | N | A/C | A/C | A/C | A | T | G | G |
| 26 | A/C | A/C | A/C | A/C | A | T | G | G |
| 27 | N | A | A | A | A | T | G | G |
| 28 | N | A | A | C | A | T | G | G |
| 29 | N | A | C | A | A | T | G | G |
| 30 | N | A | C | C | A | T | G | G |
| 31 | N | C | A | A | A | T | G | G |
| 32 | N | C | A | C | A | T | G | G |
| 33 | N | C | C | A | A | T | G | G |
| 34 | N | C | C | C | A | T | G | G |
| 35 | N | A | A | T | A | T | G | G |
| 36 | N | A | T | A | A | T | G | G |
| 37 | N | A | T | T | A | T | G | G |
| 38 | N | T | A | A | A | T | G | G |
| 39 | N | T | A | T | A | T | G | G |
| 40 | N | T | T | A | A | T | G | G |
| 41 | N | T | T | T | A | T | G | G |
| 42 | N | C | T | T | A | T | G | G |
| 43 | N | T | C | T | A | T | G | G |
| 44 | N | T | T | C | A | T | G | G |
| 45 | C | A | C | C | A | T | G | G |
| 46 | N | N | C | C | A | T | G | G |
| 47 | C | G | C | C | A | T | G | G |

In some embodiments, the 3' end of a heterologous coding sequence may be operably linked to a termination sequence including, for example, a polyadenylation site, exemplified by, but not limited to, a nopaline synthase polyadenylation site and/or a octopine T-DNA gene 7 polyadenylation site. A polyadenylation site may be provided by the heterologous gene or coding sequence according to some embodiments. A nucleic acid, according to some embodiments, may comprise a 5' untranslated region (5' UTR), a 3' untranslated region (3' UTR), and/or combinations thereof. For example, a nucleic acid may comprise (e.g., in a 5' to 3' direction) an expression control sequence, a 5' UTR, a coding sequence (e.g., a transgene), a 3' UTR, and/or a termination sequence.

Figure 2:
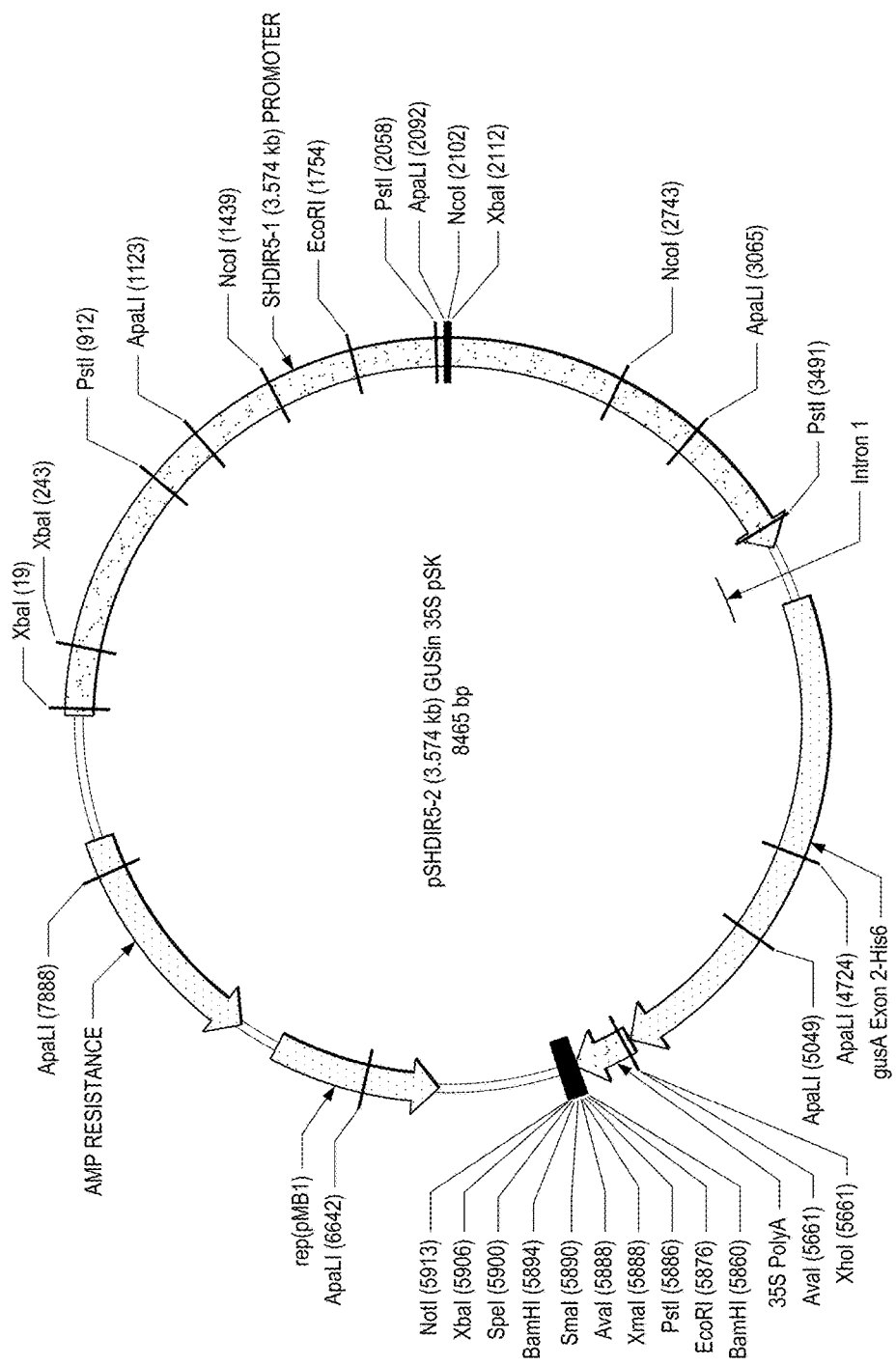
FIG. 2 illustrates a sugarcane dirigent 5-2 promoter (3.574 kb) β-glucuronidase expression pBluescript SK vector (pSHDIR5-2(3.574 kb)GUSin35SpSK) (SEQ ID NO: 9) suitable for expression in sugarcane according to a specific example embodiment of the disclosure.

The present disclosure relates, in some embodiments, to expression vectors including a nucleic acid having an expression control sequence operable to direct stem-regulated and/or defense-inducible expression. An expression vector may comprise, for example, a nucleic acid having an expression control sequence and a coding sequence operably linked to the expression control sequence. An expression vector may be contacted with (e.g., transferred into) a cell (e.g., a plant cell) in such a manner as to allow expression (e.g., transcription) of an expression vector-encoded gene product (e.g., protein) in the cell and/or one or more tissues derived from the cell. An expression control sequence may be contacted with a plant cell (e.g., an embryonic cell, a stem cell, a callus cell) under conditions that permit expression of the coding sequence in the cell and/or cells derived from the plant cell according to some embodiments. A vector may be transmitted into a plant cell in such a manner as to allow inheritance of the nucleic acid into daughter cells (e.g., somatic cells, gametes). For example, a nucleic acid may be inherited by the second progeny of plants generated from a plant derived from the transformed plant cell. In some embodiments, such inheritance may be Mendelian. Examples of expression vectors may include, without limitation the vectors shown in FIG. 1 and FIG. 2. According to some embodiments, an expression vector may include one or more selectable markers. For example, an expression vector may include a marker for selection when the vector is in a bacterial host, a yeast host, and/or a plant host.

According to some embodiments, an expression control sequence (e.g., to be contacted with a target cell) may be included in an expression cassette and/or an expression vector. In some embodiments, an expression control sequence may be included in a plant transformation vector (e.g., a binary vector). A binary vector may comprise native and/or modified portions of *Agrobacterium tumefaciens* T-DNA in some embodiments.

Microorganisms

The present disclosure relates, in some embodiments, to a microorganism comprising an expression control sequence. For example, a microorganism may comprise a bacterium, a yeast, and/or a virus. In some embodiments, an expression control sequence may comprise an expression control sequence (e.g., promoter), which directs stem-regulated and/or defense-inducible expression (e.g., a SHDIR5-1 promoter, a SHDIR5-2 promoter). A microorganism may comprise an expression control sequence and a coding sequence operably linked to the expression control sequence. Examples of microorganisms may include, without limitation, *Agrobacterium tumefaciens*, *Escherichia coli*, a lepidopteran cell line, a *Rice tungro* bacilliform virus, a *Commelina* yellow mosaic virus, a Banana streak virus, a *Taro bacilliform* virus, and/or baculovirus. An expression control sequence may be present on a genomic nucleic acid and/or an extra-genomic nucleic acid.

Plants

The present disclosure relates, in some embodiments, to a plant cell (e.g., an embryonic cell, a stem cell, a callus cell), a tissue, and/or a plant comprising an expression control sequence. A plant and/or plant cell may be a monocot cell (e.g., maize, rice, sugarcane and/or *sorghum*) in some embodiments. Examples of a monocot may include, without limitation, sugarcane, *miscanthus*, a *miscanthus*×sugarcane hybrid, switch grass, oat, wheat, barley, maize, rice, banana, *yucca*, onion, asparagus, and/or *sorghum*. A plant cell may be included in a plant tissue, a plant organ, and/or a whole plant in some embodiments. A plant cell in a tissue, organ, and/or whole plant may be adjacent, according to some embodiments, to one or more isogenic cells and/or one or more heterogenic cells. In some embodiments, a plant may include primary transformants and/or progeny thereof. A plant comprising an expression control sequence may further comprise a transgene operably linked to the expression control sequence, in some embodiments. A transgene may be expressed, according to some embodiments, in a plant comprising an expression control sequence in all (e.g., substantially all) organs, tissues, and/or cell types including, without limitation, stalks, leaves, roots, seeds, flowers, fruit, meristem, parenchyma, storage parenchyma, collenchyma, sclerenchyma, epidermis, mesophyll, bundle sheath, guard cells, protoxylem, metaxylem, phloem, phloem companion, and/or combinations thereof. A transgene operably linked to an expression control sequence, according to some embodiments, may display stem-regulated and/or defense-inducible expression. In some embodiments, a transgene and/or its gene product may be located in and/or translocated to one or more organelles (e.g., vacuoles, chloroplasts, mitochondria, plastids). An expression control sequence may be present on a genomic nucleic acid and/or an extra-genomic nucleic acid. An expression control sequence in a plant cell may be positioned within an expression cassette and/or an expression vector in some embodiments.

Expression Systems

The present disclosure relates, according to some embodiments, to a system for expression of (e.g., to high levels of) a nucleic acid sequence (e.g., comprising one or more coding sequences). For example, an expression system may be comprised in plants to be used as a biofactory for high-value proteins. Without being limited to any particular mechanism of action, an expression system may benefit from additive and/or synergistic expression control sequence activities, transcriptional synergism, and/or reduced silencing of an introduced coding sequence (e.g., transgene), a phenomenon frequently observed in plants when the same promoters are used to express the same or different transgenes, and constituting a major risk for the economic exploitation of plants as biofactories. Plants comprising an expression system may retain desirable (e.g., high) expression levels through one or more consecutive generations of transgenic plants.

In some embodiments, an expression system may comprise two or more expression control sequences (e.g., promoters) each operably linked to a respective number of clones of a single coding sequence. According to some embodiments, two, three, four, five, or more expression control sequences (e.g., promoters) may be operably linked to two, three, four, five, or more clones of a single coding sequence. Each expression control sequence independently may be constitutive and/or regulated (e.g., tissue-specific expression, developmentally-inducible expression, stress-inducible expression, defense-inducible expression, and/or drought-inducible expression) according to some embodiments. In some embodiments, each clone of a coding sequence may be identical to one or more of the other clones. Copies of a coding sequence, according to some embodiments, may differ from one another somewhat, for example, where one copy may be codon optimized for one family, genus, and/or species while another may be optimized for a different family, genus, and/or species, or not codon optimized at all. Each expression control sequence-coding sequence clone independently may be present (e.g., in a microorganism and/or plant) on an expression vector, on a genomic nucleic acid, and/or on an extra-genomic nucleic acid in some embodiments. Each expression control sequence-coding sequence clone independently, in some embodiments, may further comprise one or more terminators.

The present disclosure relates, in some embodiments, to methods for producing one promoter-one transgene expression vectors and the transgenic plants. Methods may be used, for example, to transform different varieties of sugarcane or rice by co-bombarding or co-cultivating a target explant tissue (e.g., embryogenic callus or leaf roll disc) with a transgene (e.g., a β-glucuronidase reporter gene) under the control of an expression control sequence (e.g., SHDIR5-1 promoter, SHDIR5-2 promoter).

Methods

According to some embodiments, the present disclosure relates to methods for transforming and/or transfecting a plant with a nucleic acid comprising an expression control sequence. For example, a method may comprise contacting a cell (e.g., a yeast cell and/or a plant cell) with a nucleic acid comprising an expression control sequence. Contacting a nucleic acid with a cell may comprise, in some embodiments, co-cultivating a target cell with a bacterium (e.g., *Agrobacterium*) comprising the nucleic acid (e.g., in a binary vector), electroporating a cell in the presence of the nucleic acid, infecting a cell with a virus (baculovirus) comprising the nucleic acid, bombarding a cell (e.g., a cell in a leaf, stem, and/or callus) with particles comprising the nucleic acid, agitating a cell in a solution comprising the nucleic acid and one or more whiskers (e.g., silicone carbide whiskers), and/or chemically inducing a cell to take up extracellular DNA. In some embodiments, contacting a nucleic acid with a cell may comprise contacting the nucleic acid with a plant leaf disc and/or a plant protoplast.

For example, embryonic calli and/or and other susceptible tissues may be inoculated with a binary vector comprising an expression control sequence and optionally *A. tumefaciens* T-DNA, cultured for a number of days, and then transferred to antibiotic-containing medium. Transformed shoots may be then selected after rooting in medium containing the appropriate antibiotic, and transferred to soil. Transgenic plants may be pollinated and seeds from these plants may be collected and grown on antibiotic medium.

A transgenic plant may comprise, in some embodiments, a monocot (e.g., sugarcane, rice, maize, *sorghum*). A transgenic line may be maintained from cuttings of a transgenic plant according to some embodiments. For example, a transgenic line having a transgene that is somatically and (optionally) stably inherited may be maintained from cuttings of the original transformant.

Expression of a sequence of interest (e.g., a heterologous gene, a transgene, a reporter gene) in a cell, a tissue, a seed (e.g., a developing seed), a tissue, a young seedling and/or a mature plant may be detected and/or monitored in some embodiments. For example, expression of a sequence of interest may be monitored and/or detected by one or more immunological assays, one or more histochemical assays, one or more mRNA expression assays, one or more activity (e.g., catalytic activity) assays, and/or combinations thereof. According to some embodiments, the choice of an assay may be influenced by and/or depend upon the nature of the sequence of interest. For example, RNA gel blot analysis may be used to assess transcription where appropriate nucleotide probes are available. Where antibodies to the polypeptide encoded by a sequence of interest are available, western analysis and immunohistochemical localization may be used to assess the production and/or localization of an encoded polypeptide. Where a sequence of interest encodes a gene product with catalytic activity and/or detectable biochemical properties, appropriate biochemical assays may be used.

The disclosure relates, in some embodiments, to methods for expressing a nucleic acid sequence (e.g., comprising one or more coding sequences) in a cell. For example, a method may comprise contacting a cell (e.g., a yeast cell and/or a plant cell) with a nucleic acid comprising an expression control sequence and a coding sequence operably linked to the expression control sequence under conditions that permit expression of the coding sequence. Expression, according to some embodiments, may be constitutive, conditional, native (e.g., in the normal time and/or tissue), and/or ectopic. In some embodiments, a method may further comprise expressing a nucleic acid sequence in a plant (e.g., a monocot). A method may include harvesting (e.g., partially purifying) from a plant a gene product of a nucleic acid sequence (e.g., an exogenous sequence) expressed in the plant, according to some embodiments. The disclosure relates, in some embodiments, to methods for directing stem-regulated expression and/or defense-inducible expression in a tissue and/or plant. A method may include, for example, providing a tissue and/or plant with an artificial nucleic acid having an expression control sequence (e.g., an SHDIR5-1 promoter, an SHDIR5-2 promoter) to effect such stem-regulated and/or defense-inducible expression.

In some embodiments, the present disclosure relates to methods for isolating an expression control sequence operable in at least one monocot. For example, a method may comprise screening a library (e.g., a plant genomic library, a bacterial artificial chromosome library, a plant virus genomic library) with a probe comprising a nucleic acid having a nucleic acid sequence of SEQ ID NO: 1, a complement thereof, and/or a portion thereof (e.g., 1137-4710 of SEQ ID NO: 1, under stringent hybridization conditions). A method may comprise amplifying an expression control sequence from a library (e.g., using a polymerase chain reaction) using one or more primers derived from a nucleic acid sequence of SEQ ID NO: 1, a complement thereof, and/or a portion thereof. Operability of a candidate expression control sequence in at least one monocot may be confirmed, in some embodiments, by forming a transcriptional and/or translational fusion of a candidate expression control sequence with a coding sequence expressible in the at least one monocot to form an expression cassette, transferring the expression cassette into the at least one monocot, and/or detecting expression of the coding sequence. An assay for detecting expression of the coding sequence may depend on the nature of the coding sequence. For example, a coding sequence may comprise a reporter gene (e.g., an autofluorescent protein, chloramphenicol acetyl transferase, β-glucuronidase (GUS)). Standard assays are available to sensitively detect a reporter enzyme in a transgenic organism.

The present disclosure relates, according to some embodiments, to methods for isolating an expression control sequence operable in at least one monocot. For example, a method may comprise selecting one or more primers from about 15 to about 40 nucleotides in length and corresponding to (but not necessarily identical to) sequences at or near the 5' and/or 3' ends of SEQ ID NO: 1, contacting the one or more primers with an amplification library (e.g., a partial or complete viral genomic library, a partial or complete plant genomic library) and a nucleic acid polymerase under conditions that permit amplification of an expression control sequence. A plant genomic library, according to some embodiments, may comprise nucleic acids isolated from a microorganism-infected plant, a microorganism-free plant, a mechanically-injured plant, and/or an injury-free plant. In some embodiments, a method may comprise screening a library with a probe comprising SEQ ID NO: 1 or a fragment thereof. One or more candidate expression control sequences (e.g., amplification products) may be cloned into an expression vector in a position to drive expression of a coding sequence (e.g., GUS, an autofluorescent protein). Operability of the amplification products may be assessed, for example, by contacting a plant cell with such expression vectors under conditions that permit expression of the coding sequence (e.g., microprojectile bombardment, *Agrobacterium*-mediated transformation) and examining the plant cell for the appearance of a gene product of the coding sequence (e.g., the encoded protein).

The present disclosure, in some embodiments, relates to methods of increasing expression levels of a coding sequence in at least one monocot. For example, an expression cassette and/or expression vector may be introduced into a plant in order to effect expression of a coding sequence. According to some embodiments, a method of producing a plant with increased levels of a product of a sucrose accumulating gene and/or a defense gene may comprise transforming a plant cell with an expression vector and/or expression cassette comprising an expression control sequence operably linked to a sucrose accumulating gene or a defense gene and regenerating a plant with increased levels of the product of the sucrose accumulating gene or defense gene. In some embodiments of the present disclosure, a transgenic sugarcane line may be produced in which sugar metabolism is altered to increase stem dry weight (e.g., more than about 50% sucrose, more than about 60% sucrose, more than about 70% sucrose). A transgenic sugarcane line may be produced, according to some embodiments, with enhanced bioinsecticidal activity (e.g., for protection against stem borer insects, which may be the most destructive pests). In some embodiments, expression of a bioinsecticidal protein may be induced by a defense-inducing agent (e.g., salicylic acid, jasmonic acid, methyl jasmonate).

The present disclosure, in some embodiments, relates to methods of decreasing expression levels of a coding sequence (e.g., a native plant sequence, a viral sequence) in at least one monocot. For example, a method may comprise contacting at least one monocot cell with an expression vector comprising an expression control sequence and an antisense sequence that is complementary to at least a portion of the coding sequence and operably linked to the expression control sequence. In some embodiments, a method may comprise contacting at least one monocot cell with an RNA interference (RNAi) expression vector comprising an expression control sequence and a nucleic acid sequence which is an inverted repeat of the native plant gene, the expression level of which is to be reduced and/or silenced, and operably linked to the expression control sequence. A method may comprise, in some embodiments, contacting at least one monocot cell with a cosuppression expression vector comprising an expression control sequence and a nucleic acid sequence coding for the native plant gene operably linked to the expression control sequence.

The present disclosure further relates to methods for isolating and/or purifying ("purifying") a gene product (e.g., a nucleic acid and/or a protein) from a plant. For example, a method may comprise providing a plant comprising a nucleic acid having an expression control sequence and a coding sequence operably linked to the expression control sequence, wherein the coding sequence encodes a gene product of interest. A method may comprise, according to some embodiments, producing a transgenic protein in a plant, extracting juice containing the transgenic protein from the plant, cleaning the juice to remove particulate matter, and/or transmitting the juice through at least one membrane to produce two fractions, one of the fractions containing the transgenic protein. In some embodiments, a transgenic protein may comprise a lectin, an enzyme, a vaccine, a bacterial lytic peptide, a bacterial lytic protein, an antimicrobial peptide, an antimicrobial peptide protein, an antiviral peptide, an antiviral protein, an insecticidal peptide, an insecticidal protein, a therapeutic peptide, and a therapeutic protein.

As will be understood by those skilled in the art who have the benefit of the instant disclosure, other equivalent or alternative compositions, devices, methods, and systems for expressing a nucleic acid sequence in at least one monocot and/or at least one dicot can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the position and number of expression control sequences may be varied. Each disclosed method and method step may be performed in association with any other disclosed method or method step and in any order. Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to 50 may include 55, but not 60 or 75. In addition, it may be desirable, in some embodiments, to mix and match range endpoints. Also, in some embodiments, each figure disclosed (e.g., in one or more of the Examples and/or Drawings) may form the basis of a range (e.g., disclosed value +/− about 10%, disclosed value +/− about 100%) and/or a range endpoint. Persons skilled in the art may make various changes in methods of preparing and using a composition, device, and/or system of the disclosure. For example, a composition, device, and/or system may be prepared and or used as appropriate for animal and/or human use (e.g., with regard to sanitary, infectivity, safety, toxicity, biometric, and other considerations).

These equivalents and alternatives along with obvious changes and modifications are intended to be included within the scope of the present disclosure. Accordingly, the foregoing disclosure is intended to be illustrative, but not limiting, of the scope of the disclosure as illustrated by the following claims.

The title, abstract, background, and headings are provided in compliance with regulations and/or for the convenience of the reader. They include no admissions as to the scope and content of prior art and no limitations applicable to all disclosed embodiments.

EXAMPLES

Some specific example embodiments of the disclosure may be illustrated by one or more of the examples provided herein.

Example 1

Determination of the Amino Acid Sequence of the SHDIR5-1 Protein

The protein encoded by the sugarcane (*Saccharum* spp. hybrid) dirigent 5-1 gene, SHDIR5-1, has been isolated from the sugarcane stem due to its abundance, and its amino acid sequence has been determined.

Figure 4A:
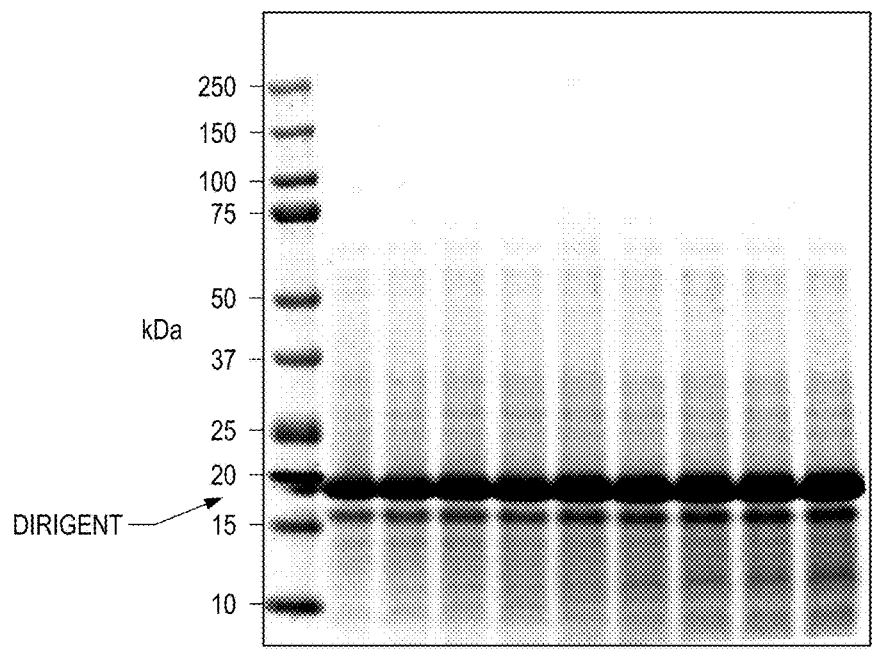
FIG. 4A illustrates the separation of total soluble proteins of the sugarcane stem by one-dimensional gel electrophoresis according to a specific example embodiment of the disclosure.
Figure 4B:
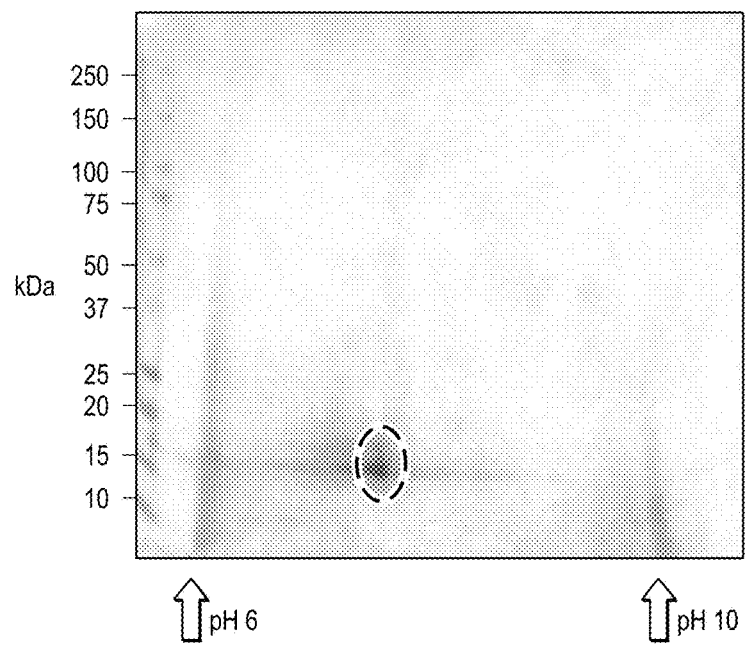
FIG. 4B illustrates the separation of total soluble proteins of the sugarcane stem by two-dimensional gel electrophoresis according to a specific example embodiment of the disclosure.

For extraction of total soluble proteins (TSPs), liquid nitrogen-frozen pre-shredded stem tissues of sugarcane (variety CP72-1210) (100 g) were homogenized with a Warring laboratory blender on ice in cold extraction buffer (50 mM 2-(N-morpholino) ethanesulfonic acid MES), 150 mM sodium chloride, 10 mM ethylenediamine tetracetic acid (EDTA), pH 6.0) (300 mL) (Woodard et al., 2009) at half maximal speed for 10 min. The protein supernatant was collected by spinning down the stem homogenate at 12,000×g for 30 min at 4° C., following filtration through three layers of cheesecloth (VWR International, LLC, Radnor, Pa.). The protein supernatant was clarified from the native proteins by pH adjustment to 4.5 (with 5 N acetic acid) and centrifugation at 12,000×g for 30 min at 4° C. The TSP pellet was recovered from the cleared supernatant after precipitation with 5 volumes of acetone at −20° C. overnight and centrifugation at 12,000×g for 30 min at 4° C. Analysis of the TSP pellet (dissolved in 100 μL of 1× sample buffer (63 mM Tris.HCl pH6.8, 1.67% (w/v) sodium dodecyl sulfate (SDS), 5% (v/v) glycerol, 5% (v/v) β-mercaptoethanol and 0.0025% (w/v) bromophenol blue) by one-dimensional gel electrophoresis, using the NuPAGE 4-12% Bis-Tris gel and 1×MES SDS running buffer system (Invitrogen, Life Technologies, Grand Island, N.Y.), revealed the presence of an abundant protein of the size of 20 kDa (FIG. 3A, 10 μL protein per lane, protein indicated by arrow). Separation of the TSP by two-dimensional (2D) gel electrophoresis, using the ReadyPrep 2-D Starter kit with the ReadyStrip IPG strips (pH6-10, 7 cm zoom) and the PROTEAN IEF and PROTEAN II XL cells (Bio-Rad Laboratories, Hercules, Calif.), identified a large protein single spot (FIG. 4B, circled spot). For amino acid sequence determination, the protein gel spot was cut and analyzed by LC/MS/MS spectrometry at the Protein Chemistry Laboratory of Texas A&M University at the world wide web tamupcl.com/Services/ProteinIdentificationProteomics/LCMSMS). The amino acid sequence of a major 20-kDa protein was determined (SEQ ID NO: 4), and it was found to be encoded by a dirigent gene, following a search of the NCBI databases using the BLASTx algorithm (Altschul et al., 1990). The amino acid sequence of the 20-kDa dirigent protein was identical to the one encoded by a dirigent 5 (SHDIR5) cDNA, except for three amino acids. The SHDIR5 cDNA was previously isolated from a sugarcane stem-expressed cDNA library in our laboratory (Damaj et al., 2010). The 20 kDa protein was named as SHDIR5-1 protein.

Example 2

Comparative Sequence of the SHDIR5-1 Protein Relative to Other SHDIR Proteins

The determined amino acid (aa) sequence of the SHDIR5-1 protein (SEQ ID No.: 4) was compared with that of the previously identified SHDIR proteins (Table 2).

TABLE 2

Comparison of SHDIR5-1 and SHDIR protein sequences

| | SHDIR5-1 (172 aa) 1 to 172 aa |
|---|---|
| Q117 Dirigent (187 aa)-AAR00251* | |
| 1 to 172 aa | 99% |
| Dirigent-like (187 aa)-AAV50047* | |
| 1 to 172 aa | 98% |
| Putative dirigent (187 aa)-CAF25234* | |
| 1 to 172 aa | 96% |
| SHDIR16 (187 aa)-ACY41219* | |
| 1 to 172 aa | 97% |
| Putative dirigent (187 aa)-AFD64564* | |
| 1 to 172 aa | 95% |

*NCBI GeneBank accession number
Sequence identity (%): The sequence identity (%) was obtained by BLASTp search with the SHDIR5-1 protein in the NCBI GeneBank Example 3

Isolation of the SHDIR5-1 Genomic Clone and Promoter

The promoter of the SHDIR5-1 gene has been isolated by screening a sugarcane genomic library. The nucleic acid sequence of the SHDIR5-1 promoter has also been determined.

The SHDIR5-1 genomic clone was isolated from a sugarcane genomic library, constructed in a bacterial artificial chromosome (BAC) (Clemson University Genomics Institute (CUGI, Clemson, S.C.). The six filters of the sugarcane BAC genomic library SHCRBa, prepared by CUGI, were screened with the SHDIR5 full-length cDNA (isolated from a sugarcane stem-expressed cDNA library: Damaj et al., 2010) probe using CUGI hybridization services at the world wide web genome.clemson.edu/services/genomics/hybridization). Screening of the sugarcane BAC genomic library with the SHDIR5 cDNA probe revealed the presence of several hybridization signals, indicating that the SHDIR5 gene is present in multiple copies in the sugarcane genome. Twelve SHDIR5 genomic clones exhibiting strong hybridization to the SHDIR5 cDNA were selected for Southern blot analysis.

Bacterial stocks of the twelve positive SHDIR5 BAC genomic clones were obtained from CUGI, and DNA for these clones was isolated using the NucleoBond PC 500 plasmid DNA purification kit (Clontech Laboratories, Inc., A Takara Bio Company, Mountain View, Calif.). DNA (10 μg) was digested with the restriction endonuclease HindIII at 37° C. overnight and resolved on a 0.7% (w/v) agarose gel. Digested DNA was transferred by capillary blotting to an Amersham Hybond™ XL membrane (GE Healthcare Biosciences, Pittsburgh, Pa.) in an alkaline solution (0.4 M sodium hydroxide) (Sambrook and Russell 2001). The membrane was prehybridized for three hours at 65° C. in hybridization buffer (0.5 M sodium hydrogen phosphate pH 7.2, 7% (w/v) SDS, 1 mM EDTA and 1% (w/v) bovine serum albumin), and hybridized overnight at the same temperature with the SHDIR5 full-length cDNA probe pre-labeled radioactively using the Random Primer DNA Labeling System (Invitrogen, Life Technologies). Following hybridization, the membrane was washed once with each of three buffers with increasing stringency, 2×SSC/0.5% (w/v) SDS, 1×SSC/0.25% (w/v) SDS and 0.5×SSC/0.125% (w/v) SDS, for 20 min each at 65° C. The radioactivity signal was detected with an x-ray film after exposure for 20 min at room temperature. Southern blot analysis of the twelve SHDIR5 genomic clones revealed the presence of multiple unique restriction fragments containing the SHDIR5 gene (FIG. 3), indicating that these SHDIR5 clones were most likely members of a multigene family.

One SHDIR5 BAC genomic clone, 204J06, designated as SHDIR5-1, was selected for further study (See FIG. 3). A 7.0 kb HindIII fragment of the SHDIR5-1 clone 204J06 was subcloned into the polylinker HindIII site of the pBluescript SKII vector (Stratagene, Agilent Technologies, Santa Clara, Calif.) and sequenced by Alpha Biolaboratory (Burlingame, Calif.). The identity of the genomic sequence of the SHDIR5-1 clone was verified by searching databases through NCBI using the BLASTn algorithm (Altschul et al., 1990). Genomic and cDNA sequence data for the SHDIR5-1 gene was aligned using SeqMan of Lasergene, Version 8 software (DNASTAR, Inc., Madison, Wis.). The SHDIR5-1 genomic clone contained a 4.710 kb promoter region (upstream regulatory sequence) (SEQ ID NO: 1).

Example 4

Comparative Sequence of the SHDIR5-1 Promoter Relative to Other SHDIR Promoters

The nucleotide (nt) sequence of the SHDIR5-1 promoter with its 5' untranslated region (UTR) (4.710 kb) (SEQ ID NO: 1) and without its 5'UTR (4.662 kb) (SEQ ID NO: 1)

was compared with that of the previously identified SHDIR promoters (Table 3 and Table 4). The nucleotide sequence locations in Tables 3 and 4 correspond to the location of the nucleotide sequence with respect to the location of the start codon in SEQ ID NO: 1. Therefore, the referenced sequences appear as negative numerical values in Table 3 and 4, with −4710 corresponding to the 5' end (nucleotide number 1 of SEQ ID NO: 1) and −1 corresponding to the 3' end (nucleotide number 4710 of SEQ ID NO: 1).

TABLE 3

Comparison of SHDIR5-1 and SHDIR promoter sequences

|  | SHDIR5-1 (4.710 kb) |
|---|---|
| 67pro dirigent (1.044 kb)-AY81896* | |
| −206 to −778 nt | 94% (−4021 to −4590) |
| −931 to −1044 nt | 95% (−4598 to −4710) |
| SHDIR16 (2.631 kb)-GU062718* | |
| −1791 to −2367 nt | 94% (−4021 to −4593) |
| −2518 to −2631 nt | 97% (−4598 to −4710) |
| dpb dirigent (1.151 kb)-AJ626722* | |
| −355 to −872 nt | 95% (−4021 to −4536) |
| −1038 to −1151 nt | 97% (−4598 to −4710) |
| FN95-1702 DIR (0.039 kb)-JQ622282* | |
| −1 to −39 nt (5'UTR) | 100% (−4674 to −4710) |
| Q117 Dirigent (0.035 kb)-AY421731* | |
| −1 to −35 nt (5'UTR) | 100% (−4678 to −4710) |
| c67 dirigent (0.032 kb)-AY781903* | |
| −2 to −32 nt (5'UTR) | 100% (−4682 to −4710) |

*NCBI GeneBank accession number
Sequence identity (%): The sequence identity (%) was obtained by BLASTn search with the SHDIR5-1 protein in the NCBI GeneBank

TABLE 4

Comparison of SHDIR5-1 (no 5'UTR) and SHDIR promoter sequences

|  | SHDIR5-1 (no 5'UTR) (4.662 kb) |
|---|---|
| 67pro dirigent (1.044 kb)-AY81896* | |
| −206 to −778 nt | 94% (−4021 to −4590) |
| −931 to −992 nt | 95% (−4598 to −4660) |
| SHDIR16 (2.631 kb)-GU062718* | |
| −1791 to −2367 nt | 94% (−4021 to −4593) |
| −2518 to −2579 nt | 95% (−4598 to −4660) |
| dpb dirigent (1.151 kb)-AJ626722* | |
| −355 to −872 nt | 95% (−4021 to −4536) |
| −1038 to− 1099 nt | 95% (−4598 to −4660 |

*NCBI GeneBank accession number
Sequence identity (%): The sequence identity (%) was obtained by BLASTn search with the SHDIR5-1 protein in the NCBI GeneBank Example 5

Identification of Putative Regulatory Motifs Enriched in the SHDIR5-1 Promoter

The sequence of the SHDIR5-1 promoter of 4.710 kb (SEQ ID NO: 1) was analyzed with PLACE signal scan (available at the world wide web dna.affrc.go.jp/sigscan/signal1.pl) and PlantCARE motif sampler (hypertext transfer protocol bioinformatics.psb.ugent.be/webtools/plantcare/html) to identify putative regulatory motifs. The in silico analysis of the SHDIR5-1 promoter predicted the presence of several potential cis-acting DNA elements involved in the regulation of gene expression in vascular tissues (Table 5). Motifs previously associated with vascular tissue-specific expression, such as the Box P (AACCAAAC) (da Costa e Silva et al., 1993; Feuillet et al., 1995; Ito et al., 2000) BSI (AGCGGG) (Lacombe et al., 2000), NTBBF1 (ACTTTA) (Baumann et al., 1999; Liu et al., 2003) and AC (ACI: ACCTACC, ACII: ACCAACC and ACHE ACCTCC) (Patzlaff et al., 2003; Fornalé et al., 2006; Winzell et al., 2010) were identified in the SHDIR5-1 promoter (Table 5). The locations of the predicted DNA elements in Table 5 correspond to the location of the nucleotide sequence with respect to the location of the start codon in SEQ ID NO: 1. Therefore, the referenced nucleotide locations appear as negative numerical values in Table 5, with −4710 corresponding to nucleotide number 1 of SEQ ID NO: 1.

The fact that the SHDIR5-1 promoter is rich with regulatory motifs specific to vascular lignifying cells suggests a functional role for the SHDIR5 gene in lignification. The SHDIR5-1 promoter was also found to contain cis-elements conferring responsiveness to the defense-induced hormones, salicylic acid (SA) and the jasmonates, and to abiotic and biotic stresses. These include the ASF1 motif (TGACG) (Rouster et al., 1997; Hwang et al., 2008), the T/G box (AACGTG) (Yamamoto et al., 2004; Wu et al., 2009) and the W-box (TTGAC) (Hiroyuki and Terauchi 2008; Hwang et al., 2008) (Table 5). The presence of SA- and jasmonate-responsive elements in the SHDIR5-1 promoter supports the possible involvement of the SHDIR5 gene in the SA- and jasmonate-induced self-defense responses.

TABLE 5

Putative regulatory motifs enriched in the SHDIR 5-1 promoter

| Name and sequence of motif | Function | Occurrence and position of motif |
|---|---|---|
| Tissue-specific motifs | | |
| AC element: ACCWWCC | Phloem/xylem; | |
| ACI element: ACCTACC | Phenyl-propanoid/lignin biosynthesis; elicitor-responsive | 8 (−885, −907, −1023, −1161, −1801, −1836, −2585) |
| ACII element: ACCAAC | | 1 (−2480) |
| ACIII element: ACCTTCC | | 1 (−1294) |
| Box P: MACCWAMC | Vascular; shoot, leaf; | |
| AACCTAAC | | 1 (−181) |
| CACAACC | Phenyl-propanoid/lignin biosynthesis | 1 (−2479) |
| CACCTACC | | 3 (−992, −1800 −1835) |
| AACCTACC | | 4 (−884, −907, −1022, −1160) |
| BS1 element: AGCGGG | Vascular, stem | 3 (−4317, −4549, −4704) |
| NTBBF1: ACTTTA | Vascular | 1 (−1711) |
| Jasmonate- and salicylic acid-responsive motifs | | |
| ASF1 motif: TGACG | Responsive to jasmonates, SA, biotic and abiotic stresses | 9 (−90, −118, −196 −673, −1797, −2133, −2671, −4048, −4476) |
| T/G box: AACGTG | Responsive to jasmonates | 2 (−2413, −3795) |
| W-box: TTGAC | Defense-related, responsive to jasmonates, SA and abiotic stresses | 7 (−119, −195, −1878, −2132, −3681, −4477, −4588) |

Motifs were identified by PLACE signal scan (http://www.dna.affrc.go.jp/PLACE/signalscan.html) and PlantCARE motif sampler (http://bioinformatics.psb.ugent.be/webtools/plantcare/html)
* The motif position is given by the number corresponding to the 5' nucleotide in the motif from the presumed translational start codon (see SHDIR5-1 promoter sequence SEQ ID NO: 1)

SHDIR5-2 (3.574 kb) promoter comprises base pairs 1137 to 4710 of full-length SHDIR5-1 (4.706 kb) promoter (SEQ ID NO: 1). SHDIR5-2 (3.574 kb) promoter (1137-4710 SEQ ID NO:1) has a reduced size compared to SHDIR5-1 (4.706 kb), but retains all of the boxes and stem-specific cis regulatory elements associated with general and stem-specific transcriptional regulation. For instance, SHDIR5-2 (3.574 kb) promoter retains the CAAT box and all TATA boxes found in SHDIR5-1 (4.706 kb) promoter, which are important for binding general transcription factors, namely CAATBOX1 (CAAT), TATABOX2 (TATAAAT), TATABOX3 (TATTAAT), TATABOX4 (TATATAA) AND TATABOX5 (TTATTT). Regulatory motifs previously associated with vascular tissue-specific expression, such as the Box P (AACCAAAC) (da Costa e Silva et al., 1993; Feuillet et al., 1995; Ito et al., 2000) BS1 (AGCGGG) (Lacombe et al., 2000), NTBBF1 (ACTTTA) (Baumann et al., 1999; Liu et al., 2003) and AC (ACI: ACCTACC, ACII: ACCAACC and ACIII: ACCTTCC) (Patzlaff et al., 2003; Fornalé et al., 2006; Winzell et al., 2010), which are found in SHDIR5-1 (4.706 kb) promoter are also retained in the SHDIR5-2 (3.574 kb) promoter (Table 5).

Example 6

SHDIR5 Promoter Constructs and Transformation of Sugarcane

Figure 5:
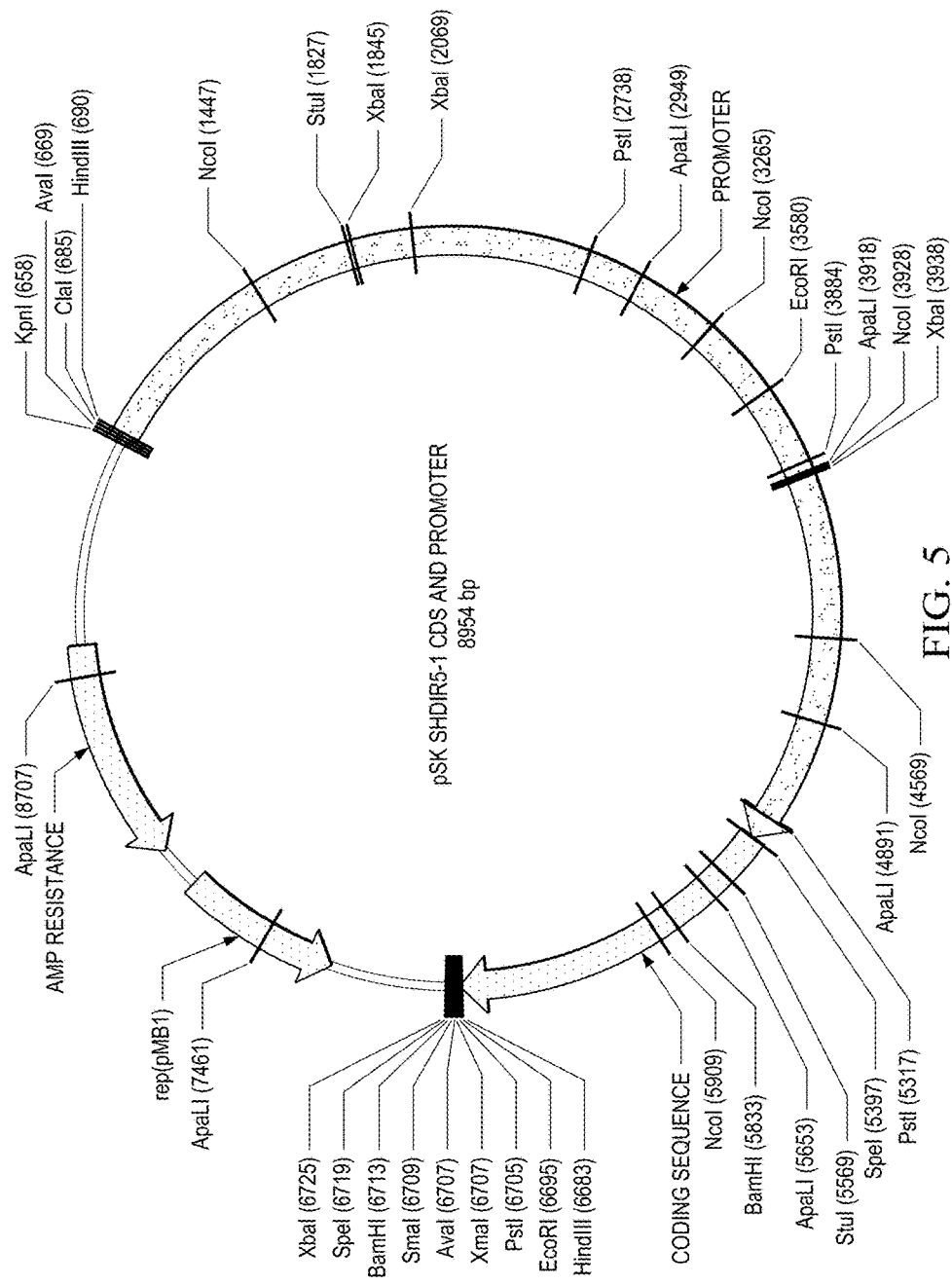
FIG. 5 illustrates a sugarcane dirigent 5-1 (SHDIR5-1) genomic clone in pBluescript SK vector (pSK SHDIR5-1 cds and promoter) according to a specific example embodiment of the disclosure.

Two expression vectors were produced by cloning the SHDIR5-1 (4.706 kb) and SHDIR5-2 (3.574 kb) promoters into a GUSin35S/pSK vector (GUS-intron was released from pCAMBIA1301 by NcoI/BstEII digestion, filled in and cloned into EcoRI/HindIII-digested filled-in pBluescript SK to which 35S terminator was added at SacI) to generate pSHDIR5-1(4.706 kb)GUSin35SpSK (FIG. 1; SEQ ID NO: 8) and pSHDIR5-2(3.574 kb)GUSin35SpSK (FIG. 2; SEQ ID NO: 9) for stable transformation of sugarcane (Table 6). Specifically, the 4.706 kb SHDIR5-1 promoter fragment (SEQ ID NO: 1) was released from pSK SHDIR5-1 cds and promoter (7.0 kb SHDIR5-1 genomic clone in pBluescript SK, FIG. 5) by HindIII/SpeI digestion, filled in (T4 DNA polymerase: New England BioLabs, Inc., Ipswich, Mass.) and cloned as a transcriptional fusion with the GUS-intron gene into the KpnI/ClaI-digested and filled-in vector GUSin35S/pSK, resulting in pSHDIR5-1(4.706 kb)GUSn35SpSK (FIG. 1; SEQ ID NO: 8). The pSHDIR5-1(4.706 kb)GUSin35SpSK vector was digested with StuI/NaeI, filled in and self-ligated to produce pSHDIR5-2(3.574 kb) GUSin35SpSK (FIG. 2; SEQ ID NO: 9).

For sugarcane transformation, embryogenic callus cultures were established from young leaf bases and immature flowers of the commercial sugarcane (Saccharum spp. hybrid, cv. CP72-1210) (Beyene et al., 2011). Transformation of callus by DNA particle gun bombardment and regeneration of shoots were done as described previously (Gallo-Meagher and Irvine, 1996; Beyene et al., 2011). Seven- to forty-week-old embryogenic calli were bombarded with the pSHDIR5-1(4.706 kb)GUSin35SpSK (FIG. 1) or the pSHDIR5-2(3.574 kb)GUSin35SpSK (FIG. 2) DNA (5 µg DNA/480 µg particles) and maintained on MS3 medium for seven days in the dark at 28° C. for recovery. Bombarded calli were later broken into small pieces and incubated in the dark at 28° C. on callus induction medium, MS3 with 2,4-dichlorophenoxyacetic acid (3 mg per L) and bialaphos (3 mg per L) selection, for a total period of two weeks. For shoot regeneration, calli were grown on MS supplemented with 6-benzylaminopurine (1.5 mg per L) and bialaphos (3 mg per L) for six to eight weeks under a light (16 h)/dark (8 h) photoperiod. Green shoots of approximately 2 cm in height were transferred in MS rooting medium containing indole-3-butyric acid (3 mg per L) and bialaphos (4 mg per L). Rooted plantlets were transferred to potting soil (Metromix, Scotts, Hope, Ark.) in small pots, maintained in an environmental growth chamber at 30° C. under 15 hours of fluorescent and incandescent light for two weeks, and transferred to the greenhouse in 15 cm-diameter pots at 30° C. under natural sunlight.

TABLE 6 pSHDIR5-1: GUS and pSHDIR5-2: GUS Constructs used for Sugarcane Transformations.

| Genetic construct | Variety | Target tissue | Age of tissue | No. of DNA shots | Green shoots/Seedlings |
|---|---|---|---|---|---|
| 1. pSHDIR5-1 (4.706 kb) GUS intron 35ST/pUbi BAR(optimized) 35ST NOST | CL88-4730 | Callus | 61 days | 60 shots (5 µg DNA/shot) BAR selection Tungsten particles | Green shoots in tissue culture One transgenic seedling in soil |
| | CP89-2143 | Callus | 80 days | 60 shots (5 µg DNA/shot) BAR selection Tungsten particles | Green shoots in tissue culture |
| | CP89-2143 | Callus | 68 days | 60 shots 5 µg DNA/shot) BAR selection Tungsten particles | 20 seedlings in tissue culture Two transgenic seedlings in soil |
| | CP89-2143 | Callus | 95 days | 46 shots 5 µg DNA/shot) BAR | 12 seedlings in tissue culture One transgenic seedling in |

TABLE 6-continued pSHDIR5-1: GUS and pSHDIR5-2: GUS Constructs used for Sugarcane Transformations.

| Genetic construct | Variety | Target tissue | Age of tissue | No. of DNA shots | Green shoots/Seedlings |
|---|---|---|---|---|---|
| | L97-128 | Callus | 40 days | selection Gold particles 74 shots 5 μg DNA/shot) BAR selection Gold and Tungsten particles | soil |
| pSHDIR5-1 (4.706 kb) GUS intron 35ST/pUbi NPTII NOST | CP89-2143 | Callus | 69 days | 98 shots 5 μg DNA/shot) NPTII selection Tungsten particles | 52 seedlings in tissue culture 7 seedlings in soil |
| | CL88-4730 | Callus | 53 days | 50 shots 5 μg DNA/shot) NPTII selection Tungsten particles | |
| 2. pSHDIR5-2 (3.574 kb) GUS intron 35ST/pUbi BAR(optimized) 35ST NOST | CP89-2143 | Callus | 56 days | 89 shots 5 μg DNA/shot) BAR selection Gold and Tungsten particles | |
| | CP89-2143 | Callus | 60 days | 63 shots 5 μg DNA/shot) BAR selection Gold particles | |
| | L97-128 | Callus | 73 days | 80 shots 5 μg DNA/shot) BAR selection Gold and Tungsten particles | |
| pSHDIR5-2 (3.574 kb) GUS intron 35ST/pUbi NPTII NOST | CL88-4730 | Callus | 53 days | 51 shots 5 μg DNA/shot) NPTII selection Tungsten particles | | pSHDIR5-1 (4.706 kb): a 4.706 kb fragment of a sugarcane dirigent 5-1 promoter;
pSHDIR5-2 (3.574 kb): a 3.574 kb fragment of a sugarcane dirigent 5-1 promoter;
pUbi: promoter for maize ubiquitin 1 gene;
GUS intron: β-glucuronidase A coding sequence with a synthetic first GUS exon, a castorbean catalase intron, a second GUS exon and a hexa histidine tag;
35ST: 35S terminator derived from the 35S RNA of Cauliflower mosaic virus;
NOST: terminator derived from the nopaline synthase gene of *Agrobacterium tumefaciens* Ti plasmid;
35ST NOST: double terminator consisting of 35ST and NOST;
BAR: bar gene, which is one of the most commonly used selectable markers for plant transformation. It codes for phosphinothricin acetyl transferase enzyme that detoxifies bialaphos or phophinothricin, the active ingredient of herbicides such as Basta and Finale.
BAR(optimized): The bar gene was codon-optimized for expression in sugarcane.
NPTII: nptII gene, another widely used selectable marker for plant transformation. It codes for neomycin phosphotransferase (or aminoglycodise 3'-phosphotransferase) enzyme, which inactivates by phopsphorylation a range of aminoglycoside antibiotics such as geneticin.

Example 7

Identification of Transformed Sugarcane Lines

A total of 37 independent SHDIR5-1(4.706 kb):GUS sugarcane lines were generated after plant transformation with the SHDIR5-1 promoter (4.706 kb) (SEQ ID NO: 1) (Table 7). A total of 13 independent SHDIR5-2(3.574 kb): GUS sugarcane lines were produced following plant transformation with the truncated SHDIR5-2 promoter (3.574 kb) (1137-4710 of SEQ ID NO. 1) (Table 7).

TABLE 7

List of the generated sugarcane lines that are transgenic for SHDIR5-1: GUS and SHDIR5-2: GUS.

| Genetic construct | Variety | Target tissue | Age of tissue | No. of DNA shots | Transgenic line (No. of plants) |
|---|---|---|---|---|---|
| SHDIR5-1 (4.706 kb): GUS intron: 5ST/UBI1: BAR(optimized): 35ST NOST | CL88-4730 | Callus | 61 days | 60 shots (5 µg DNA/shot) BAR selection Tungsten particles | Line 1 (3 plants) |
| | CP89-2143 | Callus | 68 days | 60 shots (5 µg DNA/shot) BAR selection Tungsten particles | Line 6 (3 plants) Line 12 (3 plants) Line 37 (1 plant) |
| | CP89-2143 | Callus | 95 days | 46 shots 5 µg DNA/shot) BAR selection Gold particles | Line 4 (1 plant Line 5 (1 plant) Line 6 (1 plant) Line 7 (1 plant) Line 10 (3 plants) Line 13 (1 plant) |
| | L97-128 | Callus | 40 days | 37 shots 5 µg DNA/shot) BAR selection Gold particles | Line 1 (38 plants) Line 2 (6 plants) Line 3 (25 plants) Line 4 (4 plants) Line 6 (13 plants) Line 7 (24 plants) Line 8 (11 plants) |
| | L97-128 | Callus | 40 days | 37 shots 5 µg DNA/shot) BAR selection Tungsten particles | Line 1 (10 plants) Line 2 (12 plants) Line 3 (11 plants) Line 4 (10 plants) Line 5 (6 plants) |
| SHDIR5-1 (4.706 kb): GUS intron: 35ST/UBI1: NPTII: NOST | CP89-2143 | Callus | 69 days | 98 shots 4 µg DNA/shot) NPTII selection Tungsten particles | Line 1 (2 plants) Line 3 (1 plant) Line 10 (3 plants) Line 12 (3 plants) Line 18 (3 plants) Line 23 (1 plant) Line 26 (3 plants) Line 28 (1 plant) Line 35 (3 plants) Line 39 (1 plant) Line 42 (1 plant) Line 45 (3 plants) Line 50 (3 plants) Line 52 (3 plants) Line 55 (1 plant) |
| SHDIR5-2 (3.574 kb): GUS intron: 35ST/UBI1: BAR(optimized): 35ST NOST | CP89-2143 | Callus | 56 days | 89 shots 5 µg DNA/shot) BAR selection Gold and Tungsten particles | Line 2 (1 plant) Line 3 (1 plant) |
| | L97-128 | Callus | 73 days | 40 shots 5 µg DNA/shot) BAR selection Gold particles | Line 1 (11 plants) Line 2 (18 plants) Line 3 (11 plants) Line 4 (15 plants) Line 5 (10 plants) |
| | L97-128 | Callus | 73 days | 40 shots 5 µg DNA/shot) BAR selection | Line 1 (5 plants) Line 2 (6 plants) Line 3 (10 plants) Line 4 (6 plants) |

TABLE 7-continued

List of the generated sugarcane lines that are
transgenic for SHDIR5-1: GUS and SHDIR5-2: GUS.

| Genetic construct | Variety | Target tissue | Age of tissue | No. of DNA shots | Transgenic line (No. of plants) |
|---|---|---|---|---|---|
| | | | | Tungsten particles | Line 5 (7 plants) Line 6 (10 plants) |

SHDIR5-1 (4.706 kb): a 4.706 kb fragment of a sugarcane dirigent 5-1 promoter;
SHDIR5-2 (3.574 kb): a 3.574 kb fragment of a sugarcane dirigent 5-1 promoter;
UBI1: promoter for maize ubiquitin 1 gene;
GUS intron: β-glucuronidase A coding sequence with a synthetic first GUS exon, a castorbean catalase intron, a second GUS exon and a hexa histidine tag;
35ST: 35S terminator derived from the 35S RNA of Cauliflower mosaic virus;
NOST: terminator derived from the nopaline synthase gene of *Agrobacterium tumefaciens* Ti plasmid;
35ST NOST: double terminator consisting of 35ST and NOST;
BAR: bar gene, which is one of the most commonly used selectable markers for plant transformation. It codes for phosphinothricin acetyl transferase enzyme that detoxifies bialaphos or phophinothricin, the active ingredient of herbicides such as Basta and Finale;
BAR(optimized): The bar gene was codon-optimized for expression in sugarcane.
NPTII: nptII gene, another widely used selectable marker for plant transformation. It codes for neomycin phosphotransferase (or aminoglycoside 3'-phosphotransferase) enzyme, which inactivates by phopsphorylation a range of aminoglycoside antibiotics such as geneticin.

As illustrated in FIG. 6, GUS gene presence and copy number in the transformed SHDIR5-1:GUS and SHDIR5-2:GUS sugarcane plants was verified by Southern blot analysis. Genomic DNA was isolated from liquid nitrogen-ground leaf tissues (3 g fresh weight) collected from young leaves of four-month-old sugarcane plants according to Tai and Tanksley (*Plant Molecular Biology Reporter* 8:297-303, 1990). Genomic DNA (10 μg per lane) was digested overnight with HindIII, electrophoresed on 0.8% (w/v) agarose gels and transferred to Amersham Hybond-XL nylon membranes (GE Healthcare Bio-Sciences Corp., NJ) in an alkaline solution (0.4 M sodium hydroxide) (Sambrook and Russell, *Molecular Cloning: A Laboratory Manual*, 2001). Pre-hybridization, hybridization, washing and detection of DNA gel blots were performed as described for the Lamda genomic library hybridization (see EXAMPLE 1). HindIII digested genomic DNA from thirteen transformed SHDIR5-1(4.706 kb):GUS sugarcane plants was hybridized with a GUS probe. These plants were BAR positive (they are transgenic for the bar gene, which confers resistance to bialaphos or phosphinothricin (e.g., FIG. 6). Genomic DNA from nontransformed sugarcane plants (NT) was also included as a negative control (e.g., FIG. 6). The Southern analysis identified thirteen independent SHDIR5-1(4.706 kb):GUS transgenic sugarcane lines, with most of the lines displaying a multiple hybridization banding pattern (e.g., FIG. 6). The range of copy number of GUS in these lines was 8-12. This indicates that the GUS gene driven by the SHDIR5-1 promoter has been inserted as multiple copies into the sugarcane genome.

Example 8

Characterization of Transformed Sugarcane Lines

Histochemical localization of GUS expression in transgenic SHDIR5-1(4.706 kb):GUS lines of sugarcane CP89-2143 and CL88-4474 (*Saccharum* spp. hybrids) was determined by incubating tissues (stem, leaf and root) in GUS reaction buffer (2 mM 5-bromo-4-choloro-3-indolyl β-D-glucuronide cyclohexylamine salt dissolved in 1% dimethylformamide, 1 mM potassium ferricyanide, 1 mM potassium ferrocyanide, 1 mM EDTA, 50 mM NaPO$_4$, pH 7.0) at 37° C. for 12 hours, and reaction was stopped with 50 mM phosphate buffer (Jefferson et al., *EMBO Journal* 6:3901-3907, 1987). Stained plant tissues were photographed with a zoom stereomicroscope (Olympus SZX7, Olympus, Center Valley, Pa.). Quantitative assays of GUS activity (Jefferson et al., *EMBO Journal* 6:3901-3907, 1987) were performed on sugarcane tissues (stem, leaf and root) as follows. Tissues were homogenized in GUS extraction buffer (50 mM NaPO$_4$, pH 7.0, 10 mM EDTA, 0.1×sarkosyl, 0.1% Triton X-100 and 10 mM β-mercaptoethanol) and centrifuged for 15 min to collect protein extract. Extract (25 μL for leaf, and 75 μL for stem and root) was incubated with an equal volume of extraction buffer containing 2 mM 4-methylumbelliferyl β-D-glucuronide (fluorescent substrate) at 37° C. for 60 min, and the reaction was stopped with 0.2 M Na$_2$CO$_3$ (950 mL). Fluorescence was measured using a BioRad fluorometer at 365 nm excitation and 460 nm emission wavelengths. Each assay was performed in triplicate. Protein content of extracts was determined using a BioRad Bradford protein assay kit. Data were expressed as pmoles of 4-methylumbelliferone (MU) per min per μg of extracted protein. In order to reduce the error introduced by potential plant to plant variation, GUS gene expression was measured in three different plants regenerated from each of thirteen SHDIR5-1:GUS independent sugarcane lines. Stem, leaf and roots explants from four-month-old transgenic sugarcane plants were used for histochemical and quantitative biochemical analyses of the GUS reporter gene.

Quantitative analysis indicated that GUS activity levels of the SHDIR5-1(4.706 kb):GUS sugarcane lines were significantly high in the stem, with equal abundance in the stem top, middle and bottom areas (Table 8). Non-transformed sugarcane plants showed no significant GUS expression levels (Table 8).

TABLE 8

The SHDIR5-1 promoter drives high levels of GUS expression in the sugarcane stem

| SHDIR5-1 (4.706 kb): GUS | GUS activity (pmoles of 4-methylumbelliferone/min/μg protein) | | |
|---|---|---|---|
| transgenic line | Top | Middle | Bottom |
| 1 (CL88-4730) | 3236.6 ± 10.3 | 2952.0 ± 63.5 | 2950.1 ± 201.2 |
| 4 (CP89-2143) | 2725.8 ± 52.8 | 2664.4 ± 71.4 | 2627.5 ± 107.4 |
| 5 (CP89-2143) | 2810.6 ± 88.2 | 2448.0 ± 53.8 | 2601.1 ± 18.6 |
| 6 (CP89-2143) | 2574.8 ± 21.5 | 2816.7 ± 41.4 | 2762.5 ± 7.8 |
| 10 (CP89-2143) | 2609.3 ± 67.2 | 2522.1 ± 42.7 | 2600.8 ± 176.9 |
| 12 (CP89-2143) | 2567.2 ± 83.7 | 2561.4 ± 75.0 | 2517.5 ± 7.9 |

TABLE 8-continued

The SHDIR5-1 promoter drives high levels of GUS expression in the sugarcane stem

| SHDIR5-1 (4.706 kb): GUS | GUS activity (pmoles of 4-methylumbelliferone/min/µg protein) | | |
|---|---|---|---|
| transgenic line | Top | Middle | Bottom |
| 18 (CP89-2143) | 3131.3 ± 87.3 | 3185.5 ± 119.7 | 3252.1 ± 97.4 |
| 26 (CP89-2143) | 3189.5 ± 57.9 | 3150.9 ± 162.2 | 3187.3 ± 174.1 |
| 35 (CP89-2143) | 3307.4 ± 96.4 | 3450.3 ± 16.5 | 3259.0 ± 13.2 |
| 45 (CP89-2143) | 3239.3 ± 80.7 | 3128.4 ± 39.9 | 3441.4 ± 24.9 |
| 50 (CP89-2143) | 3347.9 ± 81.2 | 3360.7 ± 123.8 | 3210.8 ± 13.8 |
| 52 (CP89-2143) | 3052.2 ± 154.3 | 3548.0 ± 71.0 | 3143.2 ± 16.0 |
| Nontransformed (CP89-2143) | 4.5 ± 0.2 | 7.4 ± 0.2 | 3.0 ± 0.07 |

Average GUS activity was measured in stem top, middle and bottom sections of four month-old sugarcane transgenic for SHDIR5-1(4.706): GUS. The number of independent SHDIR5-1(4.706): GUS transgenic lines tested was 12. GUS activity represents three biological samples and six technical repetitions and is reported with the standard error.

Histochemical analysis showed that GUS expression driven by the SHDIR5-1 promoter was very high in the stem, specifically in the nodal areas, with equal distribution among the top, middle and bottom sections (FIGS. 7-10); however it was very low in roots (blue staining of the lignified root tips only) (FIG. 11) and not detected in leaves (no blue staining) (FIG. 11).

Figure 7:
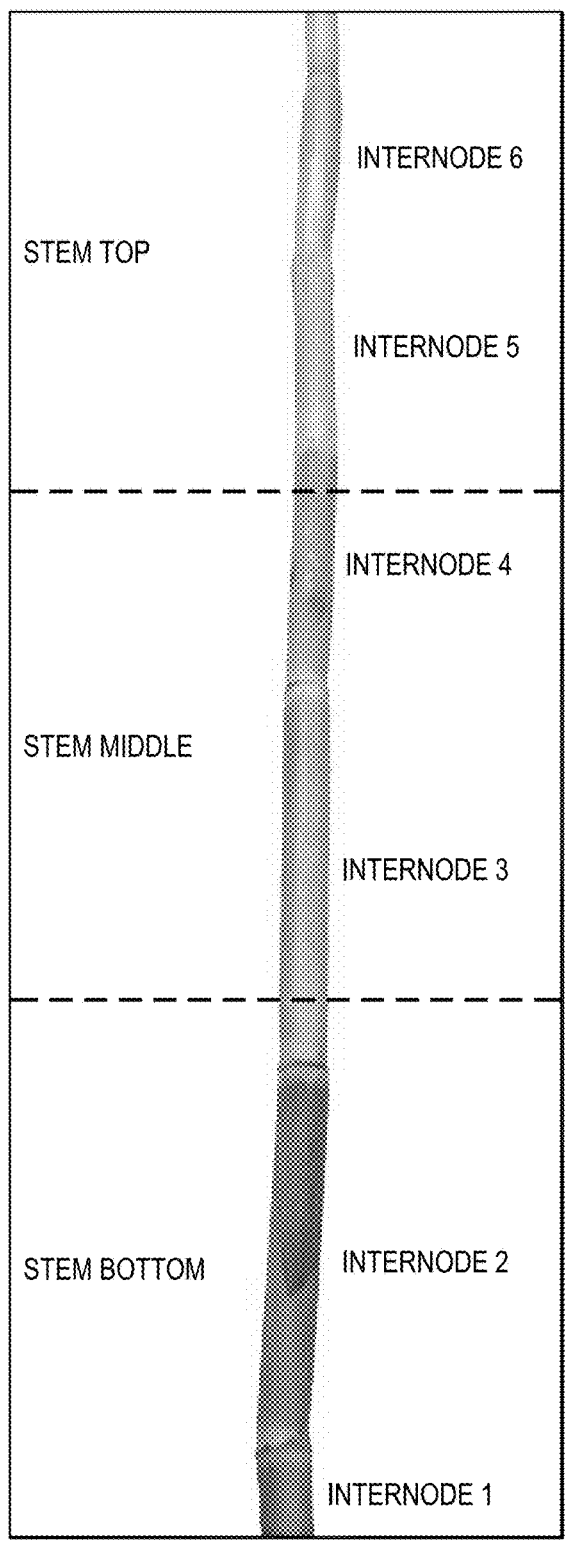
FIG. 7 illustrates a photograph of an untransformed sugarcane CP89-2143 (*Saccharum* spp. hybrids) stem with top, middle, and bottom sections, and their corresponding internodes.

FIG. 7 illustrates a photograph of an untransformed sugarcane CP89-2143 (*Saccharum* spp. hybrids) stem with top, middle and bottom sections and their corresponding internodes.

Figure 8A:
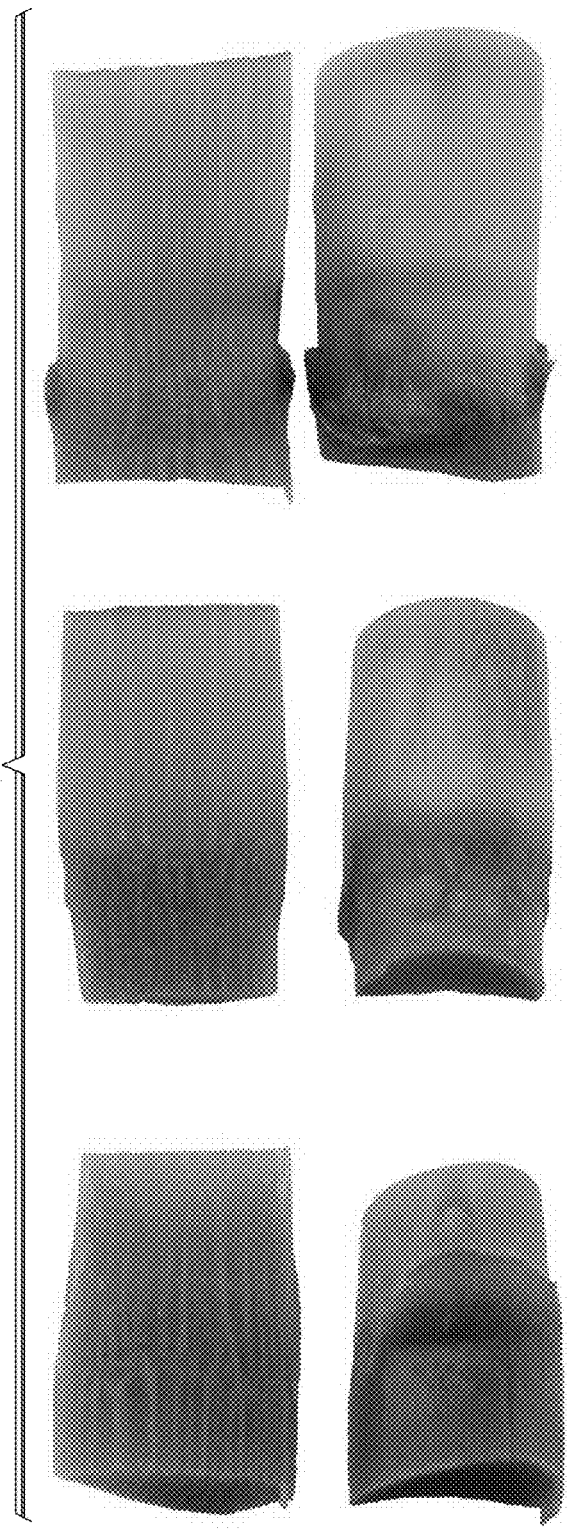
FIG. 8A illustrates a micrograph of longitudinal cross-sections of transgenic sugarcane stems showing histochemical localization of GUS gene expression driven by a SHDIR5-1 promoter in the stem bottom section according to a specific embodiment of the disclosure.
Figure 8B:
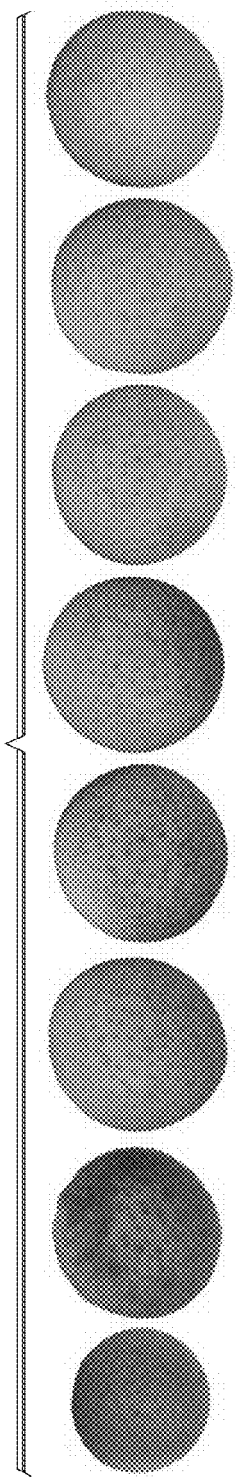
FIG. 8B illustrates a micrograph of transverse cross-sections of transgenic sugarcane stems showing histochemical localization of GUS gene expression driven by a SHDIR5-1 promoter in the stem bottom section according to a specific embodiment of the disclosure.
Figure 9B:
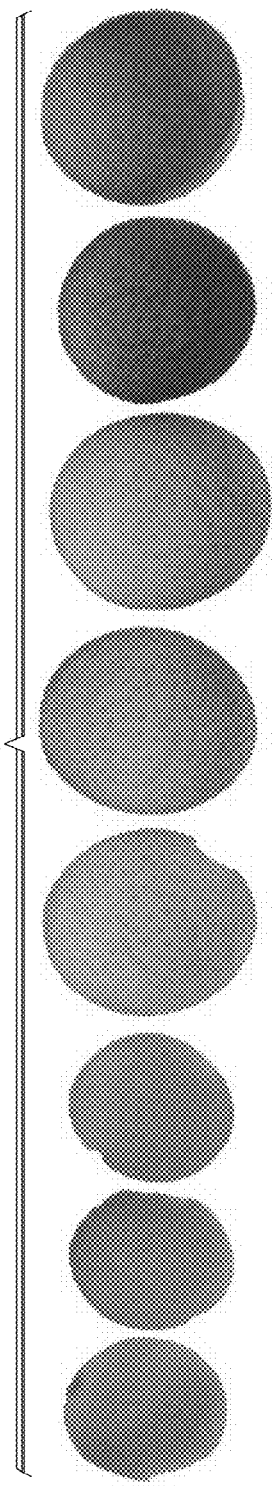
FIG. 9B illustrates a micrograph of transverse cross-sections of transgenic sugarcane stems showing histochemical localization of GUS gene expression driven by a SHDIR5-1 promoter in the stem middle section according to a specific embodiment of the disclosure.
Figure 9A:
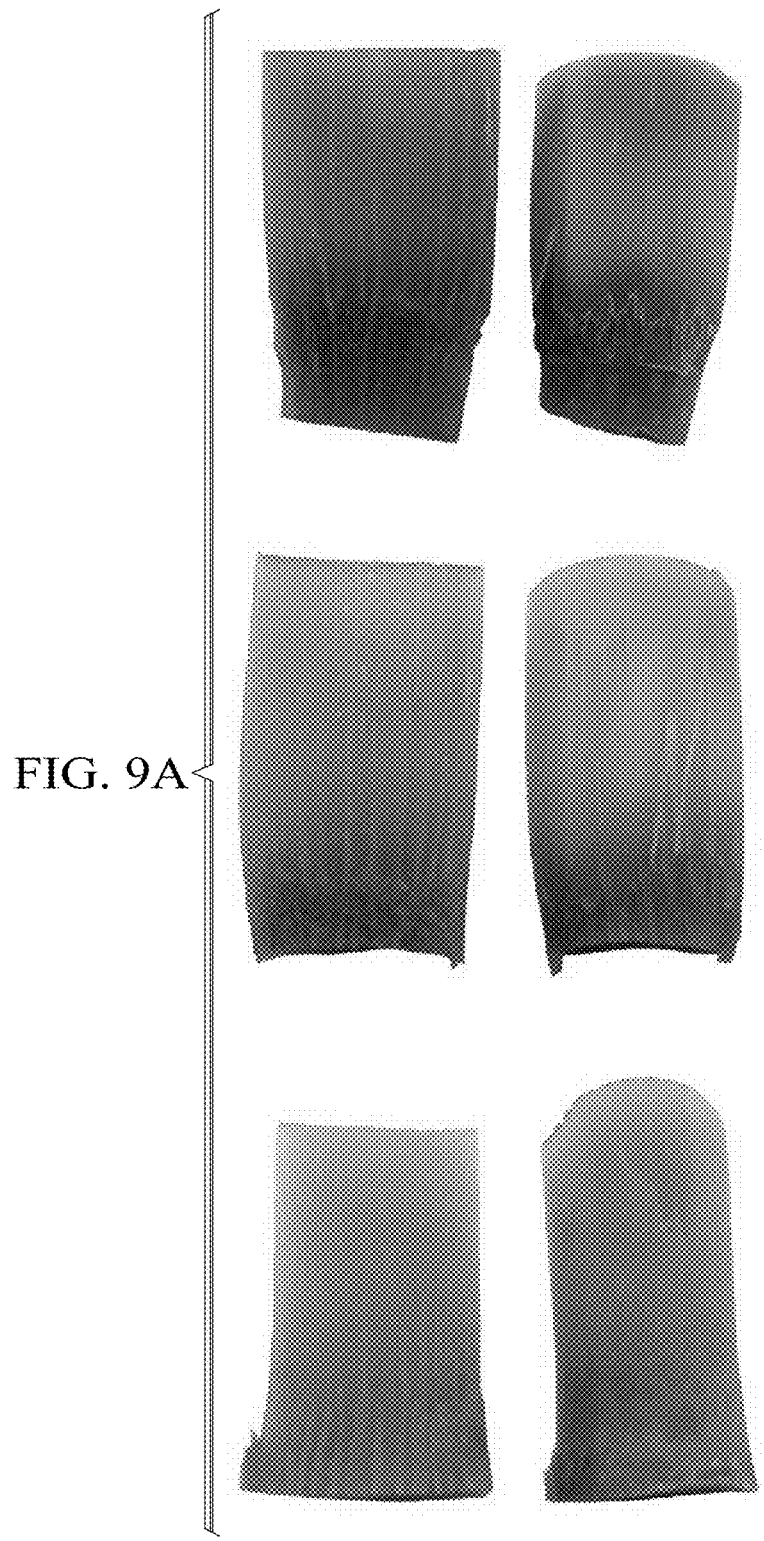
FIG. 9A illustrates a micrograph of longitudinal cross-sections of transgenic sugarcane stems showing histochemical localization of GUS gene expression driven by a SHDIR5-1 promoter in the stem middle section according to a specific embodiment of the disclosure.
Figure 10A:
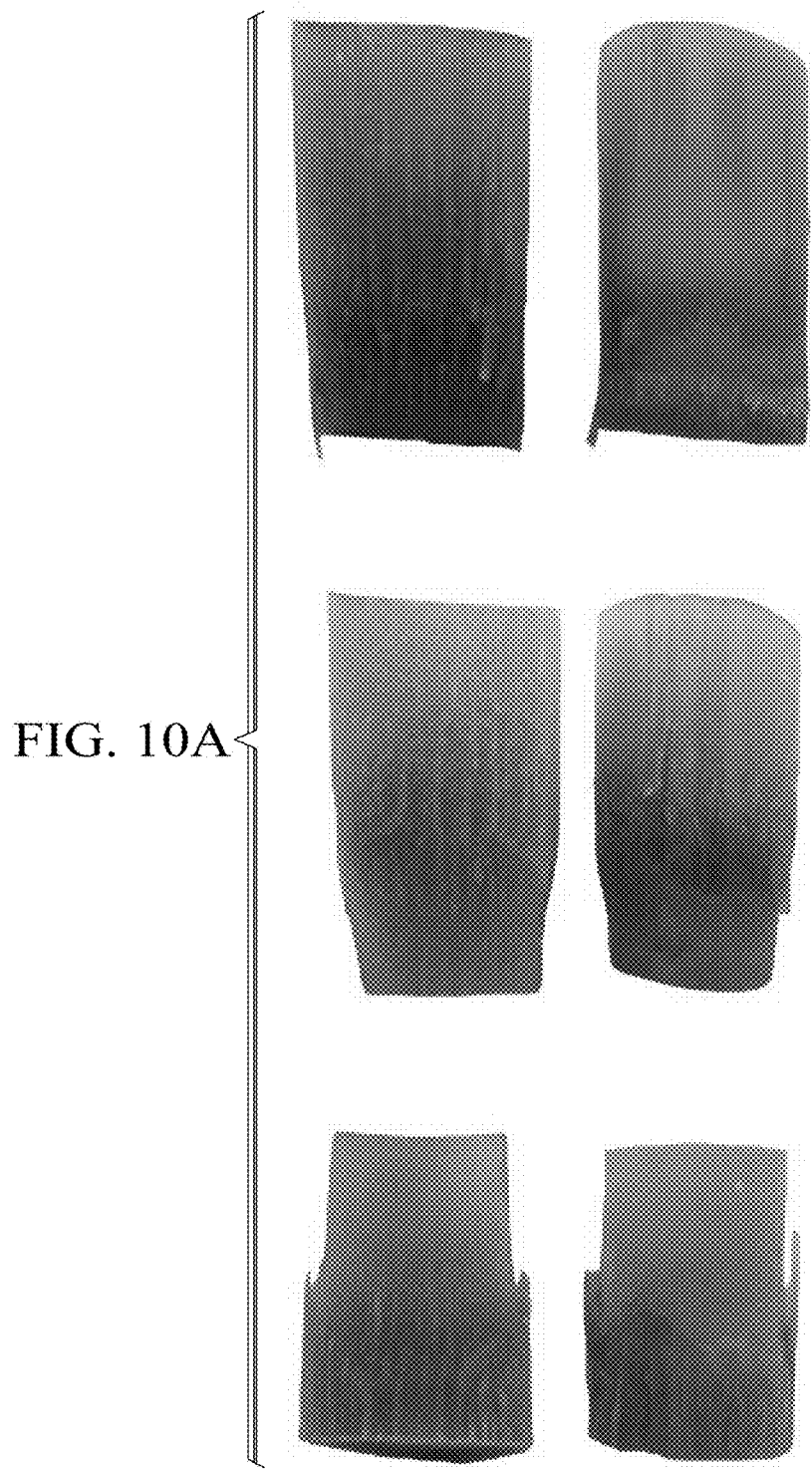
FIG. 10A illustrates a micrograph of longitudinal cross-sections of transgenic sugarcane stems showing histochemical localization of GUS gene expression driven by a SHDIR5-1 promoter in the stem top section according to a specific embodiment of the disclosure.
Figure 10B:
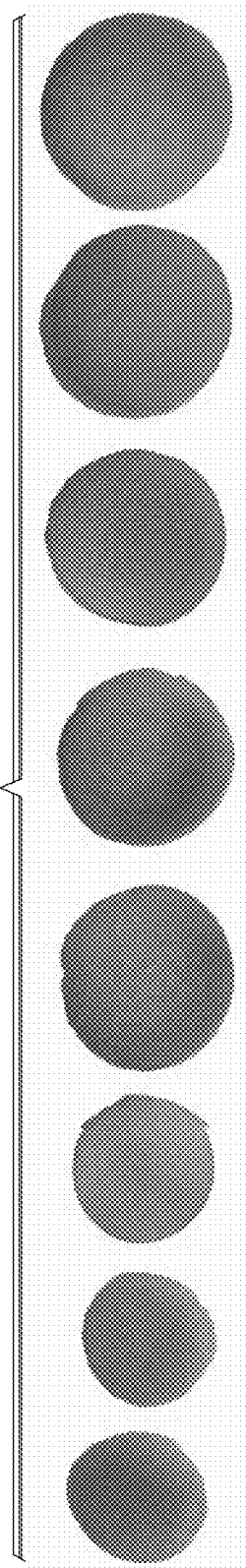
FIG. 10B illustrates a micrograph of transverse cross-sections of transgenic sugarcane stems showing histochemical localization of GUS gene expression driven by a SHDIR5-1 promoter in the stem top section according to a specific embodiment of the disclosure.

First, FIGS. 8A and 8B illustrate micrographs of longitudinal and transverse cross-sections, respectively, of transgenic sugarcane stems showing histochemical localization of GUS gene expression (blue staining) driven by a SHDIR5-1 promoter in the stem bottom section, particularly on the inside and outside of internodes 1 and 2, and the corresponding nodes. Next, FIGS. 9A and 9B illustrate micrographs of longitudinal and transverse cross-sections, respectively, of transgenic sugarcane stems showing localization of SHDIR5-1 promoter driven GUS gene expression (blue staining) in the stem middle section, particularly on the inside and outside of internodes 3 and 4, and the corresponding nodes. Finally, FIGS. 10A and 10B illustrates micrographs of longitudinal and transverse cross-sections, respectively, of transgenic sugarcane stems showing histochemical localization of GUS gene expression (blue staining) driven by a SHDIR5-1 promoter in the stem top section, particularly on the inside and outside of internodes 5 and 6, and the corresponding nodes. Thus, FIGS. 8-10 illustrate that GUS expression driven by the SHDIR5-1 promoter was very high in the stem, specifically in the nodal areas, with equal distribution among the top, middle and bottom sections.

Figure 11A:
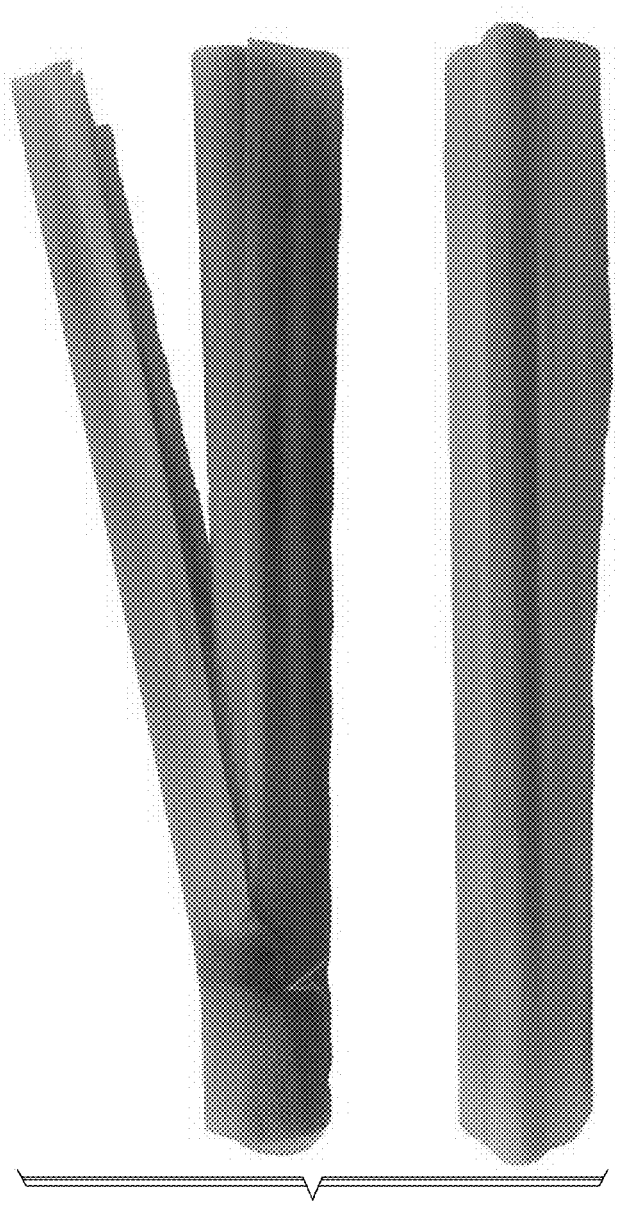
FIG. 11A illustrates a micrograph of transgenic sugarcane leaves showing histochemical localization of GUS gene expression driven by a SHDIR5-1 promoter according to a specific embodiment of the disclosure.
Figure 11B:
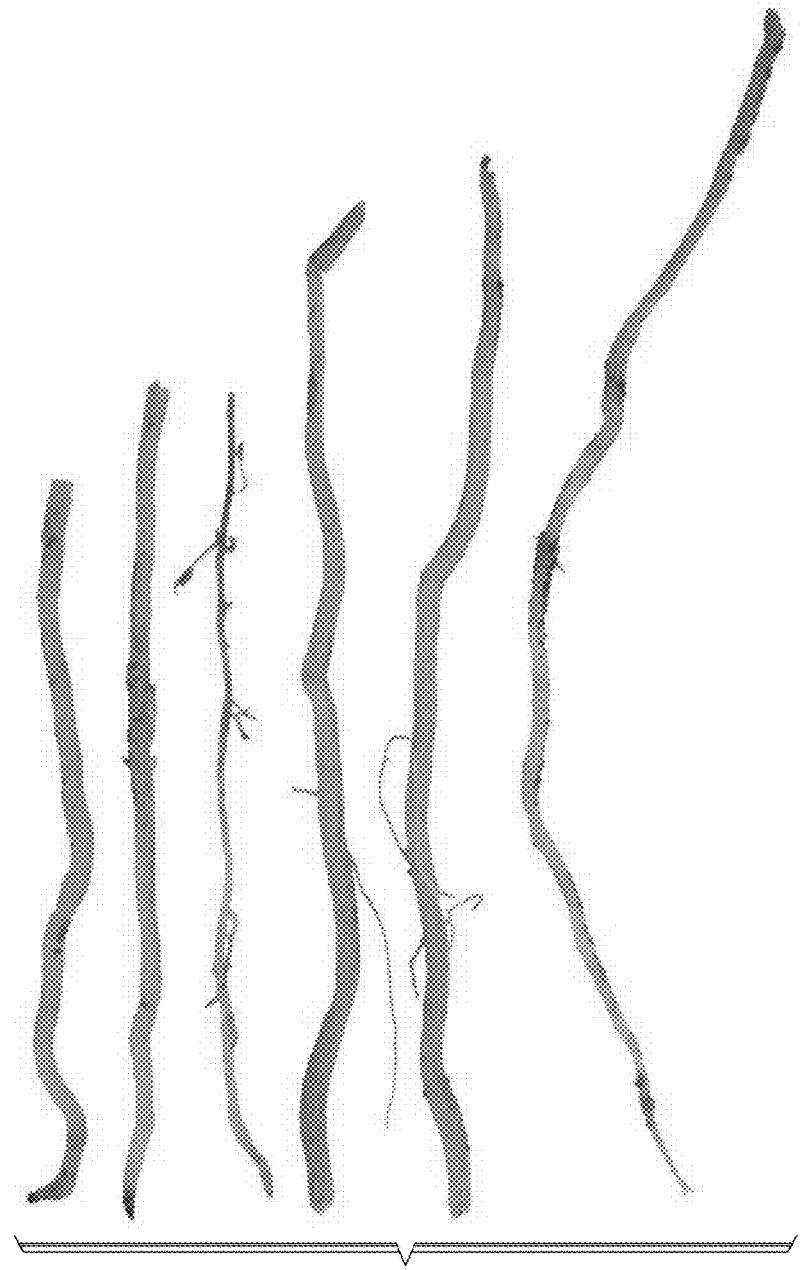
FIG. 11B illustrates a micrograph of transgenic sugarcane roots showing histochemical localization of GUS gene expression driven by a SHDIR5-1 promoter according to a specific embodiment of the disclosure.

By contrast, FIGS. 11A and 11B illustrate micrographs of transgenic sugarcane showing the absence of histochemical localization of GUS gene expression driven by a SHDIR5-1 promoter in the leaves and roots, respectively.

Figure 12B:
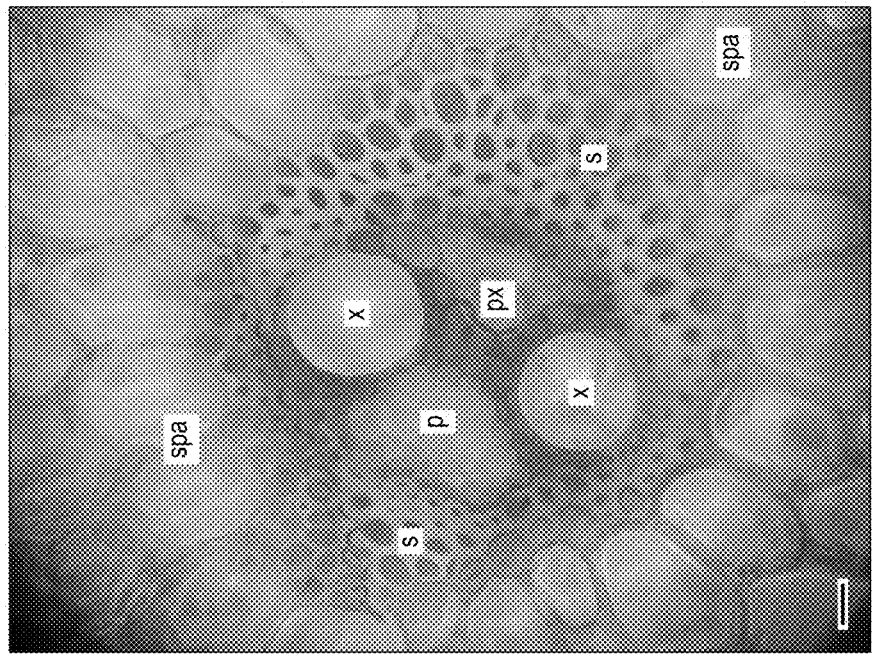
FIG. 12B illustrates a micrograph of transgenic sugarcane stems showing histochemical localization of GUS gene expression driven by a SHDIR5-1 promoter in the stem vasculature and storage parenchyma according to a specific embodiment of the disclosure.
Figure 12A:
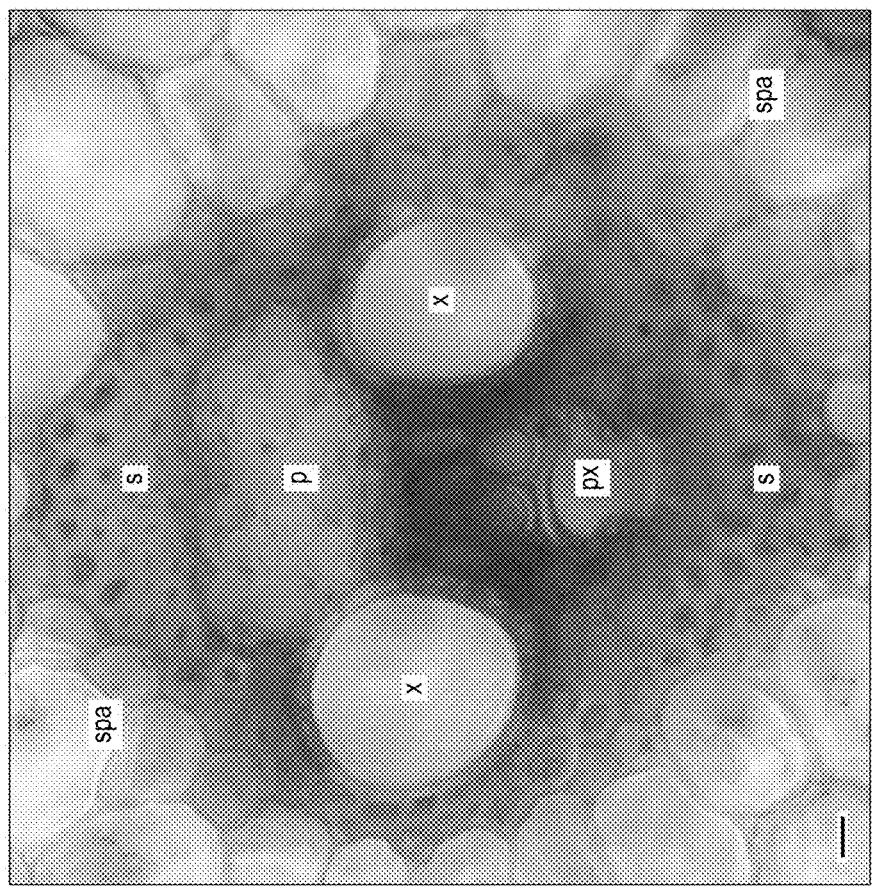
FIG. 12A illustrates a micrograph of non-transformed sugarcane stems, the stem vasculature, and storage parenchyma according to a specific embodiment of the disclosure.
Figure 14A:
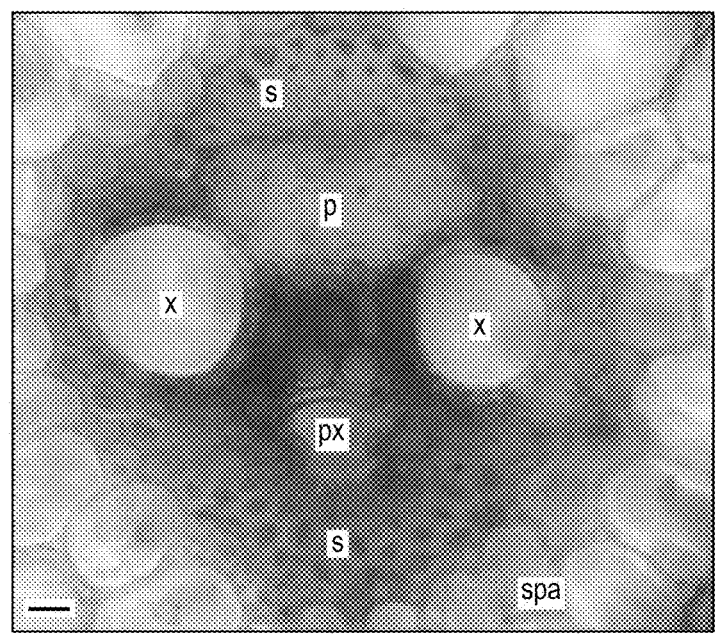
FIG. 14A illustrates a micrograph showing histochemical localization of GUS gene expression driven by a SHDIR5-1 promoter in the stem vasculature and storage parenchyma according to a specific embodiment of the disclosure.
Figure 14B:
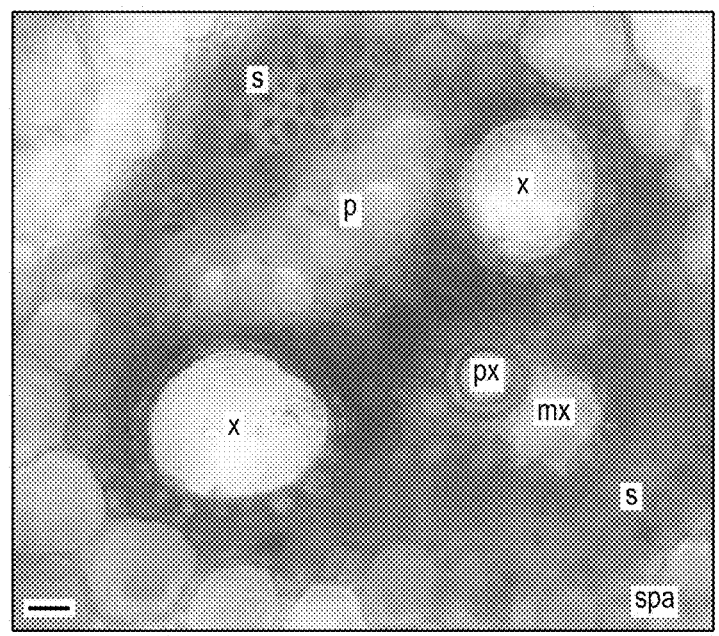
FIG. 14B illustrates a micrograph showing histochemical localization of GUS gene expression driven by a sugarcane dirigent 16 (SHDIR16) promoter in the stem vasculature according to a specific embodiment of the disclosure.
Figure 14C:
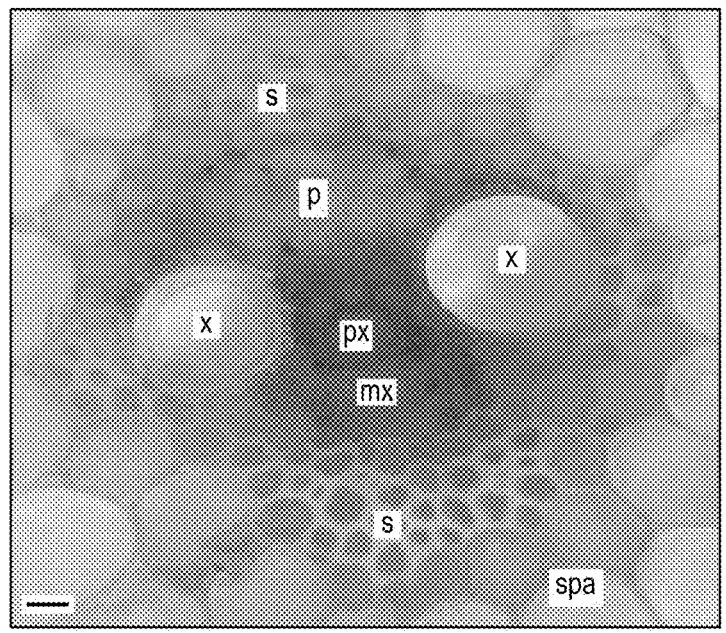
FIG. 14C illustrates a micrograph showing histochemical localization of GUS gene expression driven by a sugarcane o-methyltransferase (SHOMT) promoter in the stem vasculature according to a specific embodiment of the disclosure.
Figure 14D:
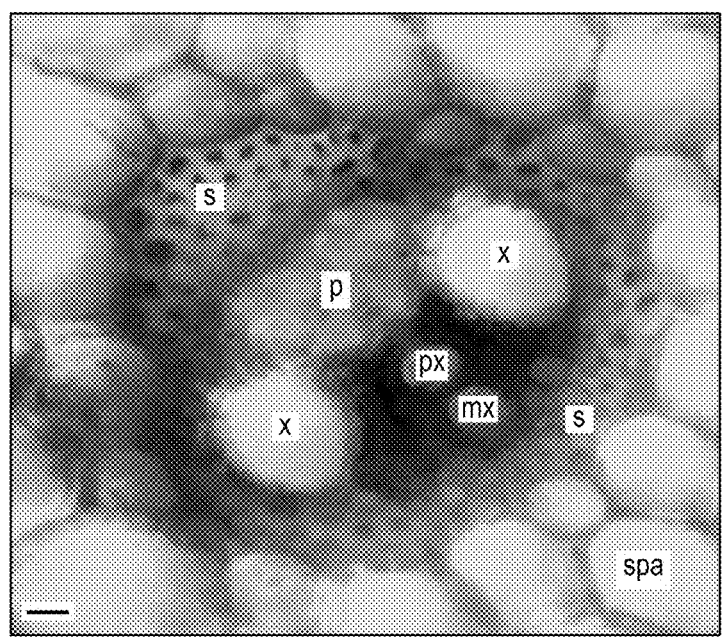
FIG. 14D illustrates a micrograph showing histochemical localization of GUS gene expression driven by a sugarcane o-methyltransferase 2 (SHOMT2) promoter in the stem vasculature according to a specific embodiment of the disclosure.
Figure 14E:
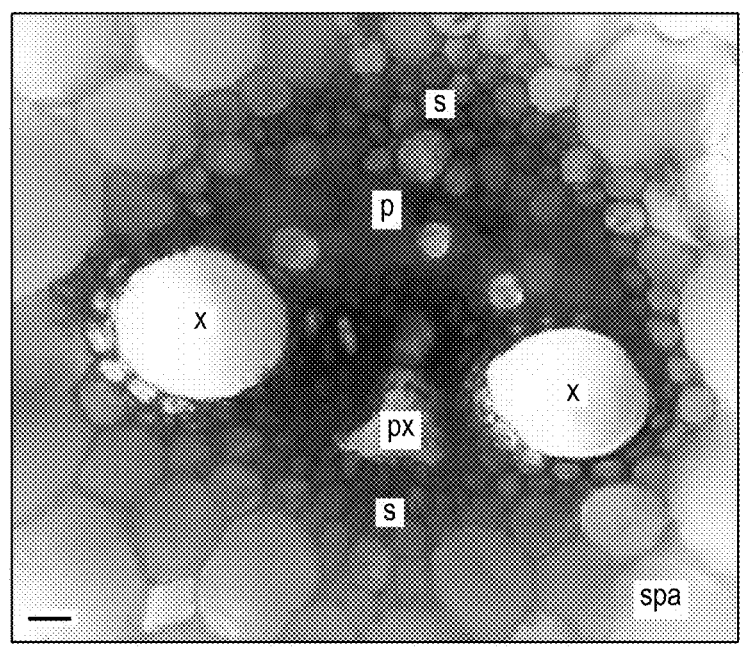
FIG. 14E illustrates a micrograph showing histochemical localization of the β-glucuronidase (GUS) gene expression driven by a Sugarcane bacilliform virus 21 (SCBV21) promoter in the stem vasculature according to a specific embodiment of the disclosure.

As illustrated by FIG. 12A, GUS expression driven by the SHDIR5-1 promoter was highly localized in the sugarcane stem vasculature, preferentially in the phloem companion cells, the bundle sheath cells of the schlerenchymatous tissue, and in cells surrounding the phloem, xylem and protoxylem, as well as, in the storage parenchyma. While non-transformed sugarcane tissues showed no GUS expression (FIG. 12B). FIG. 12B illustrates a micrograph (scale bar is 50 µm) of non-transformed sugarcane stem, with the xylem (x), protoxylem (px), phloem (p), sclerenchyma (s), and storage parenchyma (spa) labeled accordingly. FIG. 12A illustrates a micrograph (scale bar is 50 µm) of transgenic sugarcane stems showing histochemical localization of GUS gene expression (blue staining) driven by a SHDIR5-1 promoter and localized in the stem vasculature, particularly in the phloem companion cells (p), the bundle sheath cells of the schlerenchymatous tissue (s), and in cells surrounding the phloem, xylem and protoxylem, as well as, in the storage parenchyma (spa).

The localization of GUS expression driven by the SHDIR5-1 promoter to the sugarcane stem vasculature, was found in the top (FIG. 13A), middle (FIG. 13B), and bottom (FIG. 13C) sections of the stem. FIGS. 13A, 13B, and 13C illustrate micrographs (scale bar is 50 µm) of transgenic sugarcane stems showing histochemical localization of GUS gene expression (blue staining) driven by a SHDIR5-1 promoter in the vasculature and storage parenchyma of the stem top section, middle section, and bottom sections, respectively.

Histochemical localization of GUS expression directed by the SHDIR5-1 promoter in situ in sugarcane provides evidence for its activity in the stem, preferentially in the vascular bundle and nodal tissues that participate in the developmentally regulated lignification process. GUS expression directed by the SHDIR5-1 promoter in the protoxylem suggests that the SHDIR5-1 gene is involved in the development of xylem, especially the protoxylem elements that are the first to mature before the surrounding organs have elongated, possibly through activation of secondary cell wall production and lignification. Since the SHDIR5-1 promoter confers gene expression in vascular lignifying cells and is rich in vascular-specific regulatory motifs (Table 5), this suggests a functional role for the SHDIR5-1 gene in lignification. The SHDIR5-1 promoter shares similar gene expression patterns with promoters of genes involved in lignin formation and polymerization (da Costa e Silva et al., *Plant Journal* 4:125-135, 1993; Feuillet et al., *Plant Molecular Biology* 27:6651-6667, 1995), further demonstrating its suitability for targeted transgene expression to modify lignin synthesis for improving plant biomass characteristics.

Furthermore, gene expression conferred by the SHDIR5-1 in the stem storage parenchyma is of great value for metabolic engineering of sugarcane for enhanced carbon metabolism for sugar accumulation or increased fiber content for biofuel feedstock. The SHDIR5-1 promoter would be important in regulating the level of key metabolic enzymes, such as fructose 6-phosphate 1-phosphotransferase (Groenewald and Botha, *Transgenic Research* 17:85-92, 2008), for carbon partitioning between sucrose accumulation and cell wall fiber content in internodes relative to other tissues.

The stem-regulated gene expression directed by the SHDIR5-1 promoter, especially in the vascular bundles, makes it a useful tool to develop virus-resistant lines by fusing antiviral constructs to the SHDIR5-1 promoter, because many monocot viruses multiply and translocate in the vascular tissue (Yin et al., *Plant Journal* 12:1179-1188, 1997; Opalka et al., *Proceedings of the National Academy of Sciences USA* 95:3323-3328, 1998).

Example 9

Comparative Expression of SHDIR5-1 Promoter Relative to Other Promoters

The GUS expression levels driven by the stem-regulated SHDIR5-1 promoter were compared with those of four functional stem-regulated promoters, SHDIR16 (*Saccharum* hybrid dirigent 16) (*Planta* 231:1439-1458, 2010; U.S. Pat. No. 7,253,276; U.S. Pat. No. 7,754,946), SHOMT (*Saccharum* hybrid o-methyltransferase) (*Planta* 231:1439-1458, 2010; U.S. Pat. No. 7,323,622; U.S. Pat. No. 7,973,217), SHOMT2 (*Saccharum* hybrid o-methyltransferase 2) (U.S. Provisional App. No. 61/612,744; U.S. patent application Ser. No. 13/800,930; PCT/US13/32818) and SCBV21 (Sugarcane bacilliform virus) (U.S. Pat. No. 8,710,207), and of the constitutive maize ubiquitin 1 (UBI1) (*Plant Molecular Biology* 18:675-689, 1992) in transgenic sugarcane (Table 9).

TABLE 9

Comparative expression levels of GUS driven by SHDIR5-1, SHDIR16, SHOMT, SHOMT2, SCBV21 and UBI1 promoters in the sugarcane stem

| Construct | GUS activity (pmoles of 4-methylumbelliferone [MU]/min/µg protein) | | |
|---|---|---|---|
| | Stem | Leaf | Root |
| SHDIR5-1: GUS | 3259.8 ± 69.2 (2448.0-3548.0) | 19.2 ± 6.2 (12.5-23.4) | 25.6 ± 9.6 (13.0-30.4) |
| SHDIR16: GUS | 1163.2 ± 910.1 (58.0-2073.1) | 26.4 ± 18.9 (12.5-53.0) | 42.7 ± 29.9 (13.0-76.3) |
| SHOMT: GUS | 287.0 ± 97.3 (24.9-428.2) | 21.1 ± 11.2 (8.8-43.7) | 29.1 ± 18.6 (11.9-50.6) |
| SHOMT2: GUS | 84.5 ± 2.4 (40.8-128.2) | 16.1 ± 0.9 (15.1-17.1) | 53.4 ± 1.0 (27.2-56.6) |
| SCBV21: GUS | 2649.0 ± 41.3 (2466.3-3252.1) | 54.2 ± 5.2 (29.7-71.9) | 165.3 ± 4.8 (126.0-233.9) |
| UBI1: GUS | 34.2 ± 16.6 (6.0-50.0) | 68.4 ± 17.1 (17.1-93.2) | 58.1 ± 9.0 (37.1-80.1) |

Average GUS activity was measured in stems, leaves and roots of four-month-old sugarcane lines transgenic for SHDIR5-1: GUS, SHDIR16: GUS, SHOMT: GUS, SHOMT2: GUS and SCBV21: GUS. UBI1: GUS lines were included as a positive control. The number of independent SHDIR5-1: GUS, SHDIR16: GUS, SHOMT: GUS, SHOMT2: GUS, SCBV21: GUS and UBI1: GUS transgenic lines tested were thirteen, twelve, eight, six, four and four. GUS activity represents three biological samples and three technical repetitions and is reported with the standard error. The range of each set of experiments is indicated in parentheses Quantitative analysis indicated that GUS activity levels of SHDIR5-1(4.706 kb):GUS, SHDIR16:GUS, SHOMT:GUS and SHOMT2:GUS sugarcane lines were significantly higher in stems than in leaves and roots (Table 9), as compared to UBI1:GUS sugarcane lines. GUS activity levels of SHDIR5-1(4.706 kb):GUS sugarcane lines were higher in stems by 151.6- to 195.8-fold compared to leaves and by 116.7- to 188.3-fold compared to roots (Table 9). Stems from SHOMT:GUS sugarcane lines exhibited 2.8- to 9.8-fold more GUS activity than leaves and 2.1- to 8.5-fold more than roots (Table 9). SHOMT2:GUS sugarcane stems showed GUS expression levels of 2.7- to 7.5-fold higher than leaves and 1.5- to 2.3-fold higher than roots (Table 9). Increases in GUS activity of SHDIR16:GUS sugarcane stems were 4.6- to 39.1-fold compared to leaves and 4.5- to 27.1-fold compared to roots (Table 9). For SCBV21:GUS lines, stems expressed GUS in stems by 45.2-83.0-fold higher than leaves and 13.0-19.6-fold higher than roots (Table 9). UBI1:GUS sugarcane lines displayed higher GUS activity levels in leaves and roots than in stems (Table 9). Comparative quantitative analysis of GUS expression shows that the SHDIR5-1 promoter, as the SHDIR16, SHOMT, SHOMT2 and SCBV21:GUS promoters, confers stem-regulated gene expression in sugarcane, as compared to the UBI1 promoter, which directs gene expression in a constitutive manner. Increases in stem GUS activity levels were higher for SHDIR5-1(4.706 kb):GUS than for SHDIR16:GUS, SHOMT:GUS, SHOMT2:GUS and SCBV21:GUS sugarcane plants.

FIGS. 14A, 14B, 14C, 14D, and 14E illustrate micrographs (scale bar is 50 µm) showing histochemical localization of GUS gene expression (blue staining) driven by a promoter in the stem vasculature and storage parenchyma, the promoters being SHDIR5-1, SHDIR16, SHOMT, SHOMT2, and SCBV21, respectively. The xylem (x), protoxylem (px), metaxylem (mx), phloem (p), sclerenchyma (s), and storage parenchyma (spa) are labeled accordingly. As the histochemical analysis of GUS expression by SHDIR5-1 (FIG. 14A), SHDIR16 (FIG. 14B), SHOMT (FIG. 14C), and SHOMT2 (FIG. 14D) in the sugarcane stem reveals, these four promoters conferred GUS expression (blue staining) in the vascular tissues and the storage parenchyma. Meanwhile, GUS expression (blue staining) directed by the SCBV21 promoter (FIG. 14E) was confined to the storage parenchyma.

Specifically, GUS expression was associated with the bundle sheath cells of the sclerenchymatous tissue and cells surrounding the protoxylem and xylem for SHDIR5-1:GUS, SHDIR16:GUS, SHOMT:GUS and SHOMT2:GUS plants (FIGS. 14A, 14B, 14C, 14D). Phloem companion cells were also stained for GUS, and staining was more intense in SHOMT2:GUS (FIG. 14D) and SHOMT:GUS (FIG. 14C) than in SHDIR5-1:GUS (FIG. 14A) and SHDIR16:GUS (FIG. 14B) sugarcane lines. Additionally, the SHOMT2 and SHOMT promoters directed a more pronounced GUS expression in the sugarcane stem storage parenchyma than the SHDIR5-1 and SHDIR16 promoters (FIG. 14). Comparative histochemical analysis of GUS expression shows that the SHDIR5-1 promoter is active in the vascular bundles of the sugarcane stem as the SHDIR16 and SHOMT promoters. However, unlike SHDIR5-1, SHDIR16 and SHOMT, the SHOMT2 and SCBV21 promoters have significant activity in the storage parenchyma of the sugarcane stem.

The SHDIR5-1 promoter has specific advantages over the currently available promoters in its abundance in the different stem regions and its enhanced specificity in regulating gene/transgene expression in the stem vasculature and storage parenchyma tissues. The development of the SHDIR5-1 promoter enhances the small repertoire of stem-regulated promoters that are functional (not silenced) in monocot species.

What is claimed is:

1. A nucleic acid comprising an expression control sequence operably linked to a heterologous polynucleotide, wherein the control sequence comprises a sequence selected from the sequence of nucleotides 1-4710 of SEQ ID NO: 1 and the sequence of nucleotides 1137-4710 of SEQ ID NO: 1, wherein the expression control sequence has stem-specific promoter activity in at least one monocot.

2. A nucleic acid comprising an expression control sequence operably linked to a heterologous polynucleotide, wherein the expression control sequence comprises a sequence modified from nucleotides 1-4710 of SEQ ID NO: 1 by a single deletion of a single nucleotide, a single insertion of a single nucleotide, or a single substitution of a single nucleotide or wherein the expression control sequence comprises a sequence modified from nucleotides 1137-4710 of SEQ ID NO: 1 by a single deletion of a single nucleotide, a single insertion of a single nucleotide, or a single substitution of a single nucleotide.

3. The nucleic acid according to claim 1, wherein the heterologous polynucleotide alters carbon metabolism in a plant cell when expressed or transcribed.

4. The nucleic acid according to claim 1, wherein the heterologous polynucleotide encodes an insecticide effective against at least one stem-boring insect.

5. An expression vector comprising, in a 5' to 3' direction:
  a sugarcane dirigent promoter having a nucleotide sequence selected from the sequence of nucleotides 1-4710 of SEQ ID NO: 1 and the sequence of nucleotides 1137-4710 of SEQ ID NO: 1;
  an operably linked heterologous polynucleotide; and
  a 3' termination sequence, wherein the sugarcane dirigent promoter has stem-specific promoter activity in at least one monocot.

6. A bacterial cell comprising the expression vector according to claim 5.

7. A plant cell comprising the expression vector according to claim 5.

8. An expression vector comprising, in a 5' to 3' direction:
  a sugarcane dirigent promoter having a nucleotide sequence modified from nucleotides 1-4710 of SEQ ID NO: 1 by a single deletion of a single nucleotide, a single insertion of a single nucleotide, or a single substitution of a single nucleotide or having a nucleotide sequence modified from nucleotides 1137-4710 of SEQ ID NO: 1 by a single deletion of a single nucleotide, a single insertion of a single nucleotide, or a single substitution of a single nucleotide;
  an operably linked heterologous polynucleotide; and
  a 3' termination sequence, wherein the sugarcane dirigent promoter has stem-specific promoter activity in at least one monocot.

9. The plant cell according to claim 7, wherein the heterologous nolynucleotide comprises a transgene.

10. The plant cell according to claim 7, wherein the heterologous polynucleotide alters carbon metabolism in the plant cell when expressed or transcribed.

11. The plant cell according to claim 7, wherein the heterologous polynucleotide encodes an insecticide effective against at least one stem-boring insect.

12. A plant comprising the plant cell according to claim 7.

13. The plant according to claim 12, wherein the plant is a monocot.

14. The plant according to claim 13, wherein the plant is selected from the group consisting of sugarcane, *miscanthus*, a *miscanthus*×sugarcane hybrid, switch grass, oat, wheat, barley, maize, rice, banana, *yucca*, onion, asparagus, *sorghum*, and hybrids thereof.

15. A plant cell comprising the expression vector of claim 8.

16. A method for transforming a monocot plant cell, the method comprising:
 introducing into a monocot cell an expression vector comprising, in a 5' to 3' direction: (a) a sugarcane dirigent promoter having (1) a nucleotide sequence selected from (i) the sequence of nucleotides 1-4710 of SEQ ID NO: 1 and (ii) the sequence of nucleotides 1137-4710 of SEQ ID NO: 1 or (2) a nucleotide sequence modified from nucleotides 1-4710 of SEQ ID NO: 1 by a single deletion of a single nucleotide, a single insertion of a single nucleotide, or a single substitution of a single nucleotide or (3) a nucleotide sequence modified from nucleotides 1137-4710 of SEQ ID NO: 1 by a single deletion of a single nucleotide, a single insertion of a single nucleotide, or a single substitution of a single nucleotide;
 (b) an operably linked heterologous polynucleotide; and
 (c) a 3' termination sequence, wherein the sugarcane dirigent promoter has stem-specific promoter activity in at least one monocot; whereby the monocot cell is transformed with said vector.

17. A method for stem-specifically expressing an exogenous nucleic acid in a monocot, the method comprising:
 (a) introducing into a monocot cell an expression vector comprising, in a 5' to 3' direction: (1) a sugarcane dirigent promoter having (i) a nucleotide sequence selected from (A) the sequence of nucleotides 1-4710 of SEQ ID NO: 1 and (B) the sequence of nucleotides 1137-4710 of SEQ ID NO: 1 or (ii) a nucleotide sequence modified from nucleotides 1-4710 of SEQ ID NO: 1 by a single deletion of a single nucleotide, a single insertion of a single nucleotide, or a single substitution of a single nucleotide or (iii) a nucleotide sequence modified from nucleotides 1137-4710 of SEQ ID NO: 1 by a single deletion of a single nucleotide, a single insertion of a single nucleotide, or a single substitution of a single nucleotide;
 (2) an operably linked heterologous polynucleotide; and
 (3) a 3' termination sequence, wherein the sugarcane dirigent promoter has stem-specific promoter activity in at least one monocot; wherein the heterologous polynucleotide comprises the exogenous nucleic acid, wherein the sugarcane dirigent promoter is operable to drive expression of the exogenous nucleic acid in the monocot; and
 (b) regenerating a plant from said cell whereby the nucleic acid is expressed in the stem.

18. The method according to claim 17, wherein the introducing comprises biolistically bombarding the cell with a particle comprising the vector.

19. The method according to claim 17, wherein the monocot is selected from the group consisting of sugarcane, *miscanthus*, a *miscanthus*×sugarcane hybrid, switch grass, oat, wheat, barley, maize, rice, banana, *yucca*, onion, asparagus, *sorghum*, and hybrids thereof.

* * * * *

SEQUENCE LISTING

```
<160> NUMBER OF SEQ ID NOS: 9

<210> SEQ ID NO 1
<211> LENGTH: 4713
<212> TYPE: DNA
<213> ORGANISM: Saccharum spp. hybrid
<220> FEATURE:
<221> NAME/KEY: promoter
```

<222> LOCATION: (1)..(4710)
<223> OTHER INFORMATION: Dirigent 5-1 (SHDIR5-1) promoter

<400> SEQUENCE: 1

| | | | | |
|---|---|---|---|---|
| tgtgggcgac | agcttgatac | gtgtctacaa | accgaaatcc gatcgtagtc | atactccatg | 60 |
| cttcaactat | gtcagggaag | tcttcacttt | ttccgatata ggcggtgact | tcacatcttt | 120 |
| cagtttcatg | ctcctcgtac | tccctgcctt | catattctgg gcgatccttg | attccaagtc | 180 |
| tttgcatggt | agcatacaac | agcttgggaa | agccttcaat gcctagacag | taactgctgg | 240 |
| tccaaactcc | ttctgccatc | tgagagagaa | tagataagag taaacatttt | tgaaaagggg | 300 |
| aaggcattaa | gacttttgt | aaaatactct | tatatgtaaa acactaccca | gaaagcctaa | 360 |
| agtcgcgttc | tacaaccaag | gaggggagca | gggcgaaaac catagggagg | gagggaagag | 420 |
| cgagggaatg | ctcaggagct | gctcacctcg | tcctgcaacg acggccgagc | ctggctcgtg | 480 |
| cgtataggcg | tatatggtat | gcacggacaa | attgaagcga gagcaggtga | gtgagctgat | 540 |
| cgtgctgctg | ggtggtggag | gagagcacct | ccgggtgccc ttttatacac | cgaggaagag | 600 |
| gggttgtgcc | actggcttgc | ttgctcgcct | tcattggcat tgttgtggcc | aaatacctgg | 660 |
| gcagtggagc | gacgagacaa | cttccctggt | gattgtacgc cgcatgcaaa | tggacggtgg | 720 |
| atgctcagca | tgcatggtcg | gtgcctaatt | accatggtga atcttacgta | gagtcttttt | 780 |
| agggaaaaaa | acttagctct | aaaataccat | atatgtgtat acgtgctaga | ggccggagca | 840 |
| ttttcttttt | cgaaaaaata | tatagtttac | gtgcagcata tcacagattc | acggtgcttg | 900 |
| gcatgcatag | aattgcactt | cgcgtgtgcg | accatctgtg gctgatgatg | ctccctactt | 960 |
| ttcagcatat | gacagattca | cagtgttgtc | gttagttcat ggcgtggcgt | aggcgtacat | 1020 |
| agaatggaac | tgtgcgtgtg | cgaccatcct | gtgtgggatg cttttcttac | ccgtgcgaca | 1080 |
| cggtaagtcg | tcgctaccta | acaatgcgca | gcaatgtata ggaccgttta | ggcctgtttg | 1140 |
| atttcttcct | ctagaaagag | ggtgtggttt | tataggcatg accagagata | gcgtgatgtg | 1200 |
| atgctacctg | gcaggtcaag | tagcaaagta | tgaacctaaa aaaatagagg | tgaccaaatt | 1260 |
| tggaactaac | tttttcaacg | ccttggaagc | gtaaatcgtg tcggtaagat | tttgtatggt | 1320 |
| cttgacaaag | tagaaggcaa | ttcctgaggt | atttgtgcgg gaacgctaga | ttttctagat | 1380 |
| tcatgataag | atacaattac | acaataaagg | accaagtcat caaaaccgtt | ttatttcttg | 1440 |
| cgtcatgtgt | ttgtaattcg | accatcttaa | ccatgccaac gttccattga | agcacaacaa | 1500 |
| gcagacacat | tatatatgtc | ccgtggttgc | ctgcttttat gctgtgagca | ggctactgtt | 1560 |
| tacttagtgt | acttagtcat | ggcattaaaa | caccatcgca gacataatct | aagagcaacc | 1620 |
| acaatgttgc | agaaaagtag | tccataggca | ttagaatagt ctatagatag | ctgaaaacat | 1680 |
| tatagacttt | ggtatgtatc | agtatgtctt | tggttacatg acacacatca | ggtagttaat | 1740 |
| gcacttatag | aatgtcccta | ggtacacgtg | aattttttag agtactacca | ctgggtggcc | 1800 |
| gtgggtgtgc | cagtccttgt | cgccataggc | aagtgtgctt gccagaacc | atgctaacga | 1860 |
| tgcttaggtt | tcaagcattc | tgtggccaag | ttgcttgtta acacggtaat | agagttgttt | 1920 |
| actcattcaa | tatggaatac | atgtcatcac | aaacgcacac cacatgtata | tatctgaagg | 1980 |
| tggcaaacag | gggcggtgca | tatgcgagct | tacacatagc cgatgtacac | gcaaactact | 2040 |
| gcagggatga | actacaatga | ggtcatagct | aatgcctact gattcctcat | atatgaacta | 2100 |
| caaggaggac | actgggaggg | ctggatggca | catgcttata taggcaagag | ttggaggagg | 2160 |
| aatgaggggc | ctctgcatgc | atgggagcag | atgcaagtat ggtagctgta | ttaatggcga | 2220 |

-continued

```
tcaactccaa ccaccgacca ccttgggagc aacgtgcaca caacccaagc cgtctcttag    2280
atgcatggat gcatgtgcaa ctacaaatgt tcctatatgg tcggtgaatt gtttttattt    2340
gatggtacgg aggagaggca ttaaatgtgt ccacctaccc gacttgtttt tatctgatag    2400
tagcatgaag gggagggtga agatgtccag tctctagtgc tttcaaattt actgagtgga    2460
tttctggata gcatagggag ccactcgtgc atgcatggaa atttactacg tatctattga    2520
tagtaaattc atcaatgtaa aaggagaagg cacatgtgat tgacccacac catgggcagt    2580
tgaagatgtc caatctccag tgctttcaaa tttactgagt gaatttctgg atagcatagg    2640
gagccacccg tgcatgcata gaaatttact acatatctat tgatagtaaa ttcattaatg    2700
taaatggaga aggcacatgt gatgtaaatt cctcttgtcg tagtaacttt tttttatgca    2760
aaggacatgt aaaagtatag tgatgtaaat cccctaacg tggtaactt ctgcatgcaa     2820 agtacatcca cagttttata ttgtccttgc atgcatggtc attcaatttt ccatccactt    2880
cattgaattc atccactttc ttcatccatc cactgctgag gaaggctggt tgatgtgctc    2940
agtatactaa ggacacctag acttttata tagcctaggg aacacttgtg catgcatgaa     3000
atttaccgta ttgtctttag caacctgtaa attttgaacc acaggtgacg aaaatttatc    3060
acactggctt tagctaccca tacattttt gaaccacagg tgacgagaat ttaccacact     3120
gactttagcc acccttacat tttgaaccag aggtgatgca actccttgct gaagagtaca    3180
ttttctgcag gtaaagaggt cccacctggg attgctacta cagtgcacat gtccatggta    3240
aatctagatg gcaagagcac ctacaatttt tatatagcct agagaccata cgtgcatgca    3300
cgtaaattta ccgcattggc taaaaggacc acaggcgatt ctaattcctg ctggccaaca    3360 atttttgct agcaataaag aggtccttgc tatggtctca caagttgctt ccttccatgt     3420
aaaaacctgg tagcggtaaa agctcctctg tgtaaaagga gaaggcacaa tgatgtaaat    3480
ccctatagta acttcttgca tgcaaagcac acatatattt ttggacggtg cttgcatgca    3540
tgtccatcca aatttccata tgctccgttt aatgcatcca cttgcttgag gatgacaatt    3600
gcatgcatgg aagtactaca tgtgggtcat ggaggtacta caaagcacat gtataatttt    3660
ggtcggtgct tgcatgcatg cccatccaaa ttttccatctg ctccgtttaa tccatccact    3720
tgcttgagga taacaatggc atgcatgaag gtactacatg tgggtcatgg atgtactaca    3780
aagcacatgt acaattttgg atggtgtttg catgcatgtc catccaaaat ttttatctac    3840 tcccattta tgcatccact tgcttgaggc taaccatggc atgcatggag atactacatg     3900
tgggtcatag aggtactact tcatctgagc cgtggaattt ctatctaagg caccaactaa    3960
atagaacata catggacacc ttaggaggcc gcctagacgg cgcggcctca tatttctaat    4020
atatagtgaa ggggcagtag ctgattgaga atcaatcaat caagcacaat acaattaatt    4080
aattttttat tcaaacccaa ttttttcctt ttccaaccct aattatagtt ctccttttgc    4140
ctctaggaca aattgacgtg ttccaggtat cctgctgaac caagaacaac cctaggtgca    4200
cctgtcccga tggagtccca cccaggtagg cattcatagg gattcgggta tttcctgcaa    4260
aaaagcgatt aagctggctt ctaaaaccgg ctagcccgga ttctgtgggc ttcactacca    4320
gatgattttc atgtgctccg tgcattctag cactttgctg tgtaacccaa acttacatca    4380
acaactataa atatgctact tgcagaatgt tataacgaca caactcctaa tctacgaagc    4440
ctaagtttag ttttgctcgg agacaagcaa ttgtggcccg tcactatagc taagtcagag    4500
ggtagtggga gcagttgcat cgttggattg aaaacaggtg gatcatatta gatactacgc    4560
atcacatgaa cagtaaaagt gtacagtaac tgcattcact gtcatcctgt ccacgcactg    4620
```

```
cagccctcta taaatactgg catccctccc cccgttcata gatcacacaa cacaagcaag    4680
aaataaacgg tagctgccat aactagtaca atg                                 4713

<210> SEQ ID NO 2
<211> LENGTH: 6852
<212> TYPE: DNA
<213> ORGANISM: Artificial Sequence
<220> FEATURE:
<223> OTHER INFORMATION: Expression cassette SHDIR5-1(4.710 kb)-GUS-NOS
<220> FEATURE:
<221> NAME/KEY: promoter
<222> LOCATION: (1)..(4710)
<223> OTHER INFORMATION: SHDIR5-1 Promoter
<220> FEATURE:
<221> NAME/KEY: CDS
<222> LOCATION: (4711)..(6519)
<223> OTHER INFORMATION: GUS
<220> FEATURE:
<221> NAME/KEY: terminator
<222> LOCATION: (6590)..(6842)
<223> OTHER INFORMATION: NOS

<400> SEQUENCE: 2
tgtgggcgac agcttgatac gtgtctacaa accgaaatcc gatcgtagtc atactccatg      60
cttcaactat gtcagggaag tcttcacttt ttccgatata ggcggtgact tcacatcttt     120
cagtttcatg ctcctcgtac tccctgcctt catattctgg gcgatccttg attccaagtc     180
tttgcatggt agcatacaac agcttgggaa agccttcaat gcctagacag taactgctgg     240
tccaaactcc ttctgccatc tgagagagaa tagataagag taaacatttt tgaaaaaggg     300
aaggcattaa gacttttttgt aaaatactct tatatgtaaa acactaccca gaaagcctaa    360
agtcgcgttc tacaaccaag gaggggagca gggcgaaaac catagggagg agggaagag      420 cgagggaatg ctcaggagct gctcacctcg tcctgcaacg acgccgagc ctggctcgtg      480 cgtataggcg tatatggtat gcacggacaa attgaagcga gagcaggtga gtgagctgat     540
cgtgctgctg ggtggtggag gagagcacct ccgggtgccc ttttatacac cgaggaagag    600
gggttgtgcc actggcttgc ttgctcgcct tcattggcat tgttgtggcc aaataccttg    660
gcagtggagc gacgagacaa cttccctggt gattgtacgc cgcatgcaaa tggacggtgg    720
atgctcagca tgcatggtcg gtgcctaatt accatggtga atcttacgta gagtcttttt     780
agggaaaaaa acttagctct aaaataccat atatgtgtat acgtgctaga ggccggagca    840 ttttctttt cgaaaaaata tatagtttac gtgcagcata tcacagattc acggtgcttg     900
gcatgcatag aattgcactt cgcgtgtgcg accatctgtg gctgatgatg ctccctactt     960
ttcagcatat gacagattca cagtgttgtc gttagttcat ggcgtggcgt aggcgtacat   1020
agaatggaac tgtgcgtgtg cgaccatcct gtgtgggatg cttttcttac ccgtgcgaca   1080
cggtaagtcg tcgctaccta acaatgcgca gcaatgtata ggaccgttta ggcctgtttg    1140
atttcttcct ctagaaagag ggtgtggttt tataggcatg accagagata gcgtgatgtg    1200
atgctacctg gcaggtcaag tagcaaagta tgaacctaaa aaatagagg tgaccaaatt     1260 tggaactaac ttttttcaacg ccttggaagc gtaaatcgtg tcggtaagat tttgtatggt   1320
cttgacaaag tagaaggcaa ttcctgaggt atttgtgcgg gaacgctaga ttttctagat   1380
tcatgataag atacaattac acaataaagg accaagtcat caaaaccgtt ttatttcttg    1440
cgtcatgtgt ttgtaattcg accatcttaa ccatgccaac gttccattga agcacaacaa    1500
gcagacacat tatatatgtc ccgtggttgc ctgctttat gctgtgagca ggctactgtt    1560
```

```
tacttagtgt acttagtcat ggcattaaaa caccatcgca gacataatct aagagcaacc      1620
acaatgttgc agaaaagtag tccataggca ttagaatagt ctatagatag ctgaaaacat      1680
tatagacttt ggtatgtatc agtatgtctt tggttacatg acacacatca ggtagttaat      1740
gcacttatag aatgtcccta ggtacacgtg aatttttttag agtactacca ctgggtggcc      1800
gtgggtgtgc cagtccttgt cgccataggc aagtgtgctt gcccagaacc atgctaacga      1860
tgcttaggtt tcaagcattc tgtggccaag ttgcttgtta acacggtaat agagttgttt      1920
actcattcaa tatggaatac atgtcatcac aaacgcacac cacatgtata tatctgaagg      1980
tggcaaacag gggcggtgca tatgcgagct tacacatagc cgatgtacac gcaaactact      2040
gcagggatga actacaatga ggtcatagct aatgcctact gattcctcat atatgaacta      2100
caaggaggac actgggaggg ctggatggca catgcttata taggcaagag ttggaggagg      2160 aatgagggc ctctgcatgc atgggagcag atgcaagtat ggtagctgta ttaatggcga       2220
tcaactccaa ccaccgacca ccttgggagc aacgtgcaca caacccaagc cgtctcttag      2280
atgcatggat gcatgtgcaa ctacaaatgt tcctatatgg tcggtgaatt gttttttattt     2340 gatggtacgg aggagaggca ttaaatgtgt ccacctaccc gacttgtttt tatctgatag      2400
tagcatgaag gggagggtga agatgtccag tctctagtgc tttcaaattt actgagtgga      2460
tttctggata gcatagggag ccactcgtgc atgcatggaa atttactacg tatctattga      2520
tagtaaattc atcaatgtaa aaggagaagg cacatgtgat tgacccacac catgggcagt      2580
tgaagatgtc caatctccag tgctttcaaa tttactgagt gaatttctgg atagcatagg      2640
gagccacccg tgcatgcata gaaatttact acatatctat tgatagtaaa ttcattaatg      2700
taaatggaga aggcacatgt gatgtaaatt cctcttgtcg tagtaacttt tttttatgca      2760
aaggacatgt aaaagtatag tgatgtaaat cccctaacg tggtaacttt ctgcatgcaa       2820
agtacatcca cagttttata ttgtccttgc atgcatggtc attcaatttt ccatccactt      2880
cattgaattc atccactttc ttcatccatc cactgctgag gaaggctggt tgatgtgctc      2940
agtatactaa ggacacctag actttttata tagcctaggg aacacttgtg catgcatgaa      3000
atttaccgta ttgtctttag caacctgtaa attttgaacc acaggtgacg aaaatttatc      3060
acactggctt tagctaccca tacatttttt gaaccacagg tgacgagaat ttaccacact      3120
gactttagcc acccttacat tttgaaccag aggtgatgca actccttgct gaagagtaca      3180
ttttctgcag gtaaagaggt cccacctggg attgctacta cagtgcacat gtccatggta      3240
aatctagatg gcaagagcac ctacaatttt tatatagcct agagaccata cgtgcatgca      3300
cgtaaattta ccgcattggc taaaaggacc acaggcgatt ctaattcctg ctggccaaca      3360
attttttgct agcaataaag aggtccttgc tatggtctca caagttgctt ccttccatgt      3420
aaaaacctgg tagcggtaaa agctcctctg tgtaaaagga gaaggcacaa tgatgtaaat      3480
ccctatagta acttcttgca tgcaaagcac acatatattt ttggacggtg cttgcatgca      3540
tgtccatcca aatttccata tgctccgttt aatgcatcca cttgcttgag gatgacaatt      3600
gcatgcatgg aagtactaca tgtgggtcat ggaggtacta caaagcacat gtataatttt      3660
ggtcggtgct tgcatgcatg cccatccaaa tttccatctg ctccgtttaa tccatccact      3720
tgcttgagga taacaatggc atgcatgaag gtactacatg tgggtcatgg atgtactaca      3780
aagcacatgt acaatttttgg atggtgtttg catgcatgtc catccaaaat ttttatctac      3840
tcccatttta tgcatccact tgcttgaggc taaccatggc atgcatggag atactacatg      3900
tgggtcatag aggtactact tcatctgagc cgtggaattt ctatctaagg caccaactaa      3960
```

```
atagaacata catggacacc ttaggaggcc gcctagacgg cgcggcctca tatttctaat    4020
atatagtgaa ggggcagtag ctgattgaga atcaatcaat caagcacaat acaattaatt    4080 aatttttat tcaaacccaa ttttttcctt ttccaaccct aattatagtt ctccttttgc    4140
ctctaggaca aattgacgtg ttccaggtat cctgctgaac caagaacaac cctaggtgca    4200
cctgtcccga tggagtccca cccaggtagg cattcatagg gattcgggta tttcctgcaa    4260
aaaagcgatt aagctggctt ctaaaaccgg ctagcccgga ttctgtgggc ttcactacca    4320
gatgattttc atgtgctccg tgcattctag cactttgctg tgtaacccaa acttacatca    4380
acaactataa atatgctact tgcagaatgt tataacgaca caactcctaa tctacgaagc    4440
ctaagtttag ttttgctcgg agacaagcaa ttgtggcccg tcactatagc taagtcagag    4500
ggtagtggga gcagttgcat cgttggattg aaaacaggtg gatcatatta gatactacgc    4560
atcacatgaa cagtaaaagt gtacagtaac tgcattcact gtcatcctgt ccacgcactg    4620
cagccctcta taaatactgg catccctccc cccgttcata gatcacacaa cacaagcaag    4680
aaataaacgg tagctgccat aactagtaca atggtccgtc ctgtagaaac cccaacccgt    4740
gaaatcaaaa aactcgacgg cctgtgggca ttcagtctgg atcgcgaaaa ctgtggaatt    4800
gatcagcgtt ggtgggaaag cgcgttacaa gaaagccggg caattgctgt gccaggcagt    4860
tttaacgatc agttcgccga tgcagatatt cgtaattatg cgggcaacgt ctggtatcag    4920
cgcgaagtct ttataccgaa aggttgggca ggccagcgta tcgtgctgcg tttcgatgcg    4980
gtcactcatt acggcaaagt gtgggtcaat aatcaggaag tgatggagca tcagggcggc    5040
tatacgccat ttgaagccga tgtcacgccg tatgttattg ccgggaaaag tgtacgtatc    5100
accgtttgtg tgaacaacga actgaactgg cagactatcc cgccgggaat ggtgattacc    5160
gacgaaaacg gcaagaaaaa gcagtcttac ttccatgatt tctttaacta tgccgggatc    5220
catcgcagcg taatgctcta caccacgccg aacacctggg tggacgatat caccgtggtg    5280
acgcatgtcg cgcaagactg taaccacgcg tctgttgact ggcaggtggt ggccaatggt    5340
gatgtcagcg ttgaactgcg tgatgcggat caacaggtgg ttgcaactgg acaaggcact    5400
agcgggactt tgcaagtggt gaatccgcac ctctggcaac cgggtgaagg ttatctctat    5460
gaactgtgcg tcacagccaa agccagacag agtgtgata tctacccgct tcgcgtcggc    5520
atccggtcag tggcagtgaa gggcgaacag ttcctgatta ccacaaaacc gttctacttt    5580
actggctttg gtcgtcatga agatgcggac ttacgtggca aaggattcga taacgtgctg    5640
atggtgcacc accacgcatt aatggactgg attggggcca actcctaccg tacctcgcat    5700
tacccttacg ctgaagagat gctcgactgg gcagatgaac atggcatcgt ggtgattgat    5760
gaaactgctg ctgtcggctt taacctctct ttaggcattg gtttcgaagc gggcaacaag    5820
ccgaaagaac tgtacagcga agaggcagtc aacgggaaaa ctcagcaagc gcacttacag    5880
gcgattaaag agctgatagc gcgtgacaaa aaccacccaa gcgtggtgat gtggagtatt    5940
gccaacgaac cggatacccg tccgcaagtg cacgggaata tttcgccact ggcggaagca    6000
acgcgtaaac tcgacccgac gcgtccgatc acctgcgtca atgtaatgtt ctgcgacgct    6060
cacaccgata ccatcagcga tctctttgat gtgctgtgcc tgaaccgtta ttacggatgg    6120
tatgtccaaa gcggcgattt ggaaacggca gagaaggtac tggaaaaaga acttctggcc    6180
tggcaggaga aactgcatca gccgattatc atcaccgaat acggcgtgga tacgttagcc    6240
gggctgcact caatgtacac cgacatgtgg agtgaagagt atcagtgtgc atggctggat    6300
```

```
atgtatcacc gcgtctttga tcgcgtcagc gccgtcgtcg gtgaacaggt atggaatttc    6360
gccgattttg cgacctcgca aggcatattg cgcgttggcg gtaacaagaa agggatcttc    6420
actcgcgacc gcaaaccgaa gtcggcggct tttctgctgc aaaaacgctg gactggcatg    6480
aacttcggtg aaaaaccgca gcagggaggc aaacaatgaa tcaacaactc tcctggcgca    6540
ccatcgtcgg ctacagcctc gggaattgct accgagctcg aatttccccg atcgttcaaa    6600
catttggcaa taaagtttct taagattgaa tcctgttgcc ggtcttgcga tgattatcat    6660
ataatttctg ttgaattacg ttaagcatgt aataattaac atgtaatgca tgacgttatt    6720
tatgagatgg gtttttatga ttagagtccc gcaattatac atttaatacg cgatagaaaa    6780
caaaatatag cgcgcaaact aggataaatt atcgcgcgcg gtgtcatcta tgttactaga    6840
tcgggaattg cc                                                        6852
```

```
<210> SEQ ID NO 3
<211> LENGTH: 5720
<212> TYPE: DNA
<213> ORGANISM: Artificial Sequence
<220> FEATURE:
<223> OTHER INFORMATION: Expression cassette SHDIR5-1(3.578 kb)-GUS-NOS
<220> FEATURE:
<221> NAME/KEY: promoter
<222> LOCATION: (1)..(3578)
<223> OTHER INFORMATION: SHDIR5-1 Promoter
<220> FEATURE:
<221> NAME/KEY: CDS
<222> LOCATION: (3579)..(5387)
<223> OTHER INFORMATION: GUS
<220> FEATURE:
<221> NAME/KEY: terminator
<222> LOCATION: (5458)..(5710)
<223> OTHER INFORMATION: NOS

<400> SEQUENCE: 3
cctgtttgat tcttcctct agaaagaggg tgtggtttta taggcatgac cagagatagc      60
gtgatgtgat gctacctggc aggtcaagta gcaaagtatg aacctaaaaa aatagaggtg    120
accaaatttg gaactaactt tttcaacgcc ttggaagcgt aaatcgtgtc ggtaagattt    180
tgtatggtct tgacaaagta gaaggcaatt cctgaggtat ttgtgcggga acgctagatt    240
ttctagattc atgataagat acaattacac aataaaggac caagtcatca aaaccgtttt    300
atttcttgcg tcatgtgttt gtaattcgac catcttaacc atgccaacgt tccattgaag    360
cacaacaagc agacacatta tatatgtccc gtggttgcct gcttttatgc tgtgagcagg    420
ctactgttta cttagtgtac ttagtcatgg cattaaaaca ccatcgcaga cataatctaa    480
gagcaaccac aatgttgcag aaaagtagtc cataggcatt agaatagtct atagatagct    540
gaaaacatta tagactttgg tatgtatcag tatgtctttg gttacatgac acacatcagg    600
tagttaatgc acttatagaa tgtccctagg tacacgtgaa tttttttagag tactaccact    660 gggtggccgt gggtgtgcca gtccttgtcg ccataggcaa gtgtgcttgc ccagaaccat    720
gctaacgatg cttaggtttc aagcattctg tggccaagtt gcttgttaac acggtaatag    780
agttgtttac tcattcaata tggaatacat gtcatcacaa acgcacacca catgtatata    840
tctgaaggtg gcaaacaggg gcggtgcata tgcgagctta cacatagccg atgtacacgc    900
aaactactgc agggatgaac tacaatgagg tcatagctaa tgcctactga ttcctcatat    960
atgaactaca aggaggacac tgggagggct ggatggcaca tgcttatata ggcaagagtt   1020
ggaggaggaa tgaggggcct ctgcatgcat gggagcagat gcaagtatgg tagctgtatt   1080
aatggcgatc aactccaacc accgaccacc ttgggagcaa cgtgcacaca acccaagccg   1140
```

| | |
|---|---|
| tctcttagat gcatggatgc atgtgcaact acaaatgttc ctatatggtc ggtgaattgt | 1200 |
| ttttatttga tggtacggag gagaggcatt aaatgtgtcc acctacccga cttgttttta | 1260 |
| tctgatagta gcatgaaggg gagggtgaag atgtccagtc tctagtgctt tcaaatttac | 1320 |
| tgagtggatt tctggatagc atagggagcc actcgtgcat gcatggaaat ttactacgta | 1380 |
| tctattgata gtaaattcat caatgtaaaa ggagaaggca catgtgattg acccacacca | 1440 |
| tgggcagttg aagatgtcca atctccagtg ctttcaaatt tactgagtga atttctggat | 1500 |
| agcataggga gccacccgtg catgcataga aatttactac atatctattg atagtaaatt | 1560 |
| cattaatgta aatggagaag gcacatgtga tgtaaattcc tcttgtcgta gtaacttttt | 1620 |
| tttatgcaaa ggacatgtaa aagtatagtg atgtaaatcc ccctaacgtg gtaactttct | 1680 |
| gcatgcaaag tacatccaca gttttatatt gtccttgcat gcatggtcat tcaattttcc | 1740 |
| atccacttca ttgaattcat ccactttctt catccatcca ctgctgagga aggctggttg | 1800 |
| atgtgctcag tatactaagg acacctagac tttttatata gcctagggaa cacttgtgca | 1860 |
| tgcatgaaat ttaccgtatt gtctttagca acctgtaaat tttgaaccac aggtgacgaa | 1920 |
| aatttatcac actggcttta gctacccata cattttttga accacaggtg acgagaattt | 1980 |
| accacactga ctttagccac ccttacattt tgaaccagag gtgatgcaac tccttgctga | 2040 |
| agagtacatt ttctgcaggt aaagaggtcc cacctgggat tgctactaca gtgcacatgt | 2100 |
| ccatggtaaa tctagatggc aagagcacct acaattttta tatagcctag agaccatacg | 2160 |
| tgcatgcacg taaatttacc gcattggcta aaaggaccac aggcgattct aattcctgct | 2220 |
| ggccaacaat ttttgctag caataaagag gtccttgcta tggtctcaca agttgcttcc | 2280 |
| ttccatgtaa aaacctggta gcggtaaaag ctcctctgtg taaaaggaga aggcacaatg | 2340 |
| atgtaaatcc ctatagtaac ttcttgcatg caaagcacac atatatttt ggacggtgct | 2400 |
| tgcatgcatg tccatccaaa tttccatatg ctccgtttaa tgcatccact tgcttgagga | 2460 |
| tgacaattgc atgcatggaa gtactacatg tgggtcatgg aggtactaca aagcacatgt | 2520 |
| ataattttgg tcggtgcttg catgcatgcc catccaaatt tccatctgct ccgtttaatc | 2580 |
| catccacttg cttgaggata acaatggcat gcatgaaggt actacatgtg ggtcatggat | 2640 |
| gtactacaaa gcacatgtac aattttggat ggtgtttgca tgcatgtcca tccaaaattt | 2700 |
| ttatctactc ccatttatg catccacttg cttgaggcta accatggcat gcatggagat | 2760 |
| actacatgtg ggtcatagag gtactacttc atctgagccg tggaatttct atctaaggca | 2820 |
| ccaactaaat agaacataca tggacaccct aggaggccgc ctagacggcg cggcctcata | 2880 |
| tttctaatat atagtgaagg ggcagtagct gattgagaat caatcaatca agcacaatac | 2940 |
| aattaattaa tttttattc aaacccaatt ttttcctttt ccaaccctaa ttatagttct | 3000 |
| cctttgcct ctaggacaaa ttgacgtgtt ccaggtatcc tgctgaacca agaacaaccc | 3060 |
| taggtgcacc tgtcccgatg gagtcccacc caggtaggca ttcataggga ttcgggtatt | 3120 |
| tcctgcaaaa aagcgattaa gctggcttct aaaaccggct agcccggatt ctgtgggctt | 3180 |
| cactaccaga tgattttcat gtgctccgtg cattctagca ctttgctgtg taacccaaac | 3240 |
| ttacatcaac aactataaat atgctacttg cagaatgtta taacgacaca actcctaatc | 3300 |
| tacgaagcct aagtttagtt ttgctcggag acaagcaatt gtggcccgtc actatagcta | 3360 |
| agtcagaggg tagtgggagc agttgcatcg ttggattgaa aacaggtgga tcatattaga | 3420 |
| tactacgcat cacatgaaca gtaaaagtgt acagtaactg cattcactgt catcctgtcc | 3480 |

```
acgcactgca gccctctata aatactggca tccctccccc cgttcatga tcacacaaca      3540
caagcaagaa ataaacggta gctgccataa ctagtacaat ggtccgtcct gtagaaaccc      3600
caacccgtga aatcaaaaaa ctcgacggcc tgtgggcatt cagtctggat cgcgaaaact      3660
gtggaattga tcagcgttgg tgggaaagcg cgttacaaga aagccgggca attgctgtgc      3720
caggcagttt taacgatcag ttcgccgatg cagatattcg taattatgcg ggcaacgtct      3780
ggtatcagcg cgaagtcttt ataccgaaag gttgggcagg ccagcgtatc gtgctgcgtt      3840
tcgatgcggt cactcattac ggcaaagtgt gggtcaataa tcaggaagtg atggagcatc      3900
agggcggcta tacgccattt gaagccgatg tcacgccgta tgttattgcc gggaaaagtg      3960
tacgtatcac cgtttgtgtg aacaacgaac tgaactggca gactatcccg ccgggaatgg      4020
tgattaccga cgaaaacggc aagaaaaagc agtcttactt ccatgatttc tttaactatg      4080
ccgggatcca tcgcagcgta atgctctaca ccacgccgaa cacctgggtg gacgatatca      4140
ccgtggtgac gcatgtcgcg caagactgta accacgcgtc tgttgactgg caggtggtgg      4200
ccaatggtga tgtcagcgtt gaactgcgtg atgcggatca acaggtggtt gcaactggac      4260
aaggcactag cgggactttg caagtggtga atccgcacct ctggcaaccg ggtgaaggtt      4320
atctctatga actgtgcgtc acagccaaaa gccagacaga gtgtgatatc tacccgcttc      4380
gcgtcggcat ccggtcagtg gcagtgaagg cgaacagtt cctgattaac cacaaaccgt      4440
tctactttac tggctttggt cgtcatgaag atgcggactt acgtggcaaa ggattcgata      4500
acgtgctgat ggtgcacgac cacgcattaa tggactggat tggggccaac tcctaccgta      4560
cctcgcatta cccttacgct gaagagatgc tcgactgggc agatgaacat ggcatcgtgg      4620
tgattgatga aactgctgct gtcggcttta acctctcttt aggcattggt ttcgaagcgg      4680
gcaacaagcc gaaagaactg tacagcgaag aggcagtcaa cggggaaact cagcaagcgc      4740
acttacaggc gattaaagag ctgatagcgc gtgacaaaaa ccacccaagc gtggtgatgt      4800
ggagtattgc caacgaaccg gatacccgtc cgcaagtgca cggggaatatt tcgccactgg      4860
cggaagcaac gcgtaaactc gacccgacgc gtccgatcac ctgcgtcaat gtaatgttct      4920
gcgacgctca caccgatacc atcagcgatc tctttgatgt gctgtgcctg aaccgttatt      4980
acggatggta tgtccaaagc ggcgatttgg aaacggcaga aaggtactg gaaaaagaac      5040
ttctggcctg gcaggagaaa ctgcatcagc cgattatcat caccgaatac ggcgtggata      5100
cgttagccgg gctgcactca atgtacaccg acatgtggag tgaagagtat cagtgtgcat      5160
ggctggatat gtatcaccgc gtctttgatc gcgtcagcgc cgtcgtcggt gaacaggtat      5220
ggaatttcgc cgattttgcg acctcgcaag gcatattgcg cgttggcggt aacaagaaag      5280
ggatcttcac tcgcgaccgc aaaccgaagt cggcggcttt tctgctgcaa aaacgctgga      5340
ctggcatgaa cttcggtgaa aaaccgcagc agggaggcaa acaatgaatc aacaactctc      5400
ctggcgcacc atcgtcggct acagcctcgg gaattgctac cgagctcgaa tttccccgat      5460
cgttcaaaca tttggcaata agtttctta agattgaatc ctgttgccgg tcttgcgatg      5520
attatcatat aatttctgtt gaattacgtt aagcatgtaa taattaacat gtaatgcatg      5580
acgttattta tgagatgggt ttttatgatt agagtcccgc aattatacat ttaatacgcg      5640
atagaaaaca aaatatagcg cgcaaactag gataaattat cgcgcgcggt gtcatctatg      5700
ttactagatc gggaattgcc                                                  5720
```

<210> SEQ ID NO 4
<211> LENGTH: 516

```
<212> TYPE: DNA
<213> ORGANISM: Saccharum spp. hybrid
<220> FEATURE:
<221> NAME/KEY: CDS
<222> LOCATION: (1)..(516)
<223> OTHER INFORMATION: dirigent 5-1 (SHDIR5-1) partial coding sequence

<400> SEQUENCE: 4 atg gcc agt cta aga agc gtc cta gct gtg agc cta gcc gtg gca ctt      48
Met Ala Ser Lys Arg Ser Val Leu Ala Val Ser Leu Ala Val Ala Leu
1               5                   10                  15 ttc gca gtt gct cct gca tcg ttc gca ctg gat gag aaa gag ttg cac      96
Phe Ala Val Ala Pro Ala Ser Phe Ala Leu Asp Glu Lys Glu Leu His
            20                  25                  30 ctg agt ttg tac tta aac cag aca tac agc gga aat ggc ctt aac gag     144
Leu Ser Leu Tyr Leu Asn Gln Thr Tyr Ser Gly Asn Gly Leu Asn Glu
        35                  40                  45 gcg gtg gtg gtc gaa cca ggc cta cct ggg gag ttc ggc aac atc gcc     192
Ala Val Val Val Glu Pro Gly Leu Pro Gly Glu Phe Gly Asn Ile Ala
50                  55                  60 gtc cag gac tgg cct gtg acc aat ggg gaa ggt agc gac gca acc gtc     240
Val Gln Asp Trp Pro Val Thr Asn Gly Glu Gly Ser Asp Ala Thr Val
65                  70                  75                  80 gtt gga cgt gca cag ggc atc cag ttc aaa cca agc gag agg aac gac     288
Val Gly Arg Ala Gln Gly Ile Gln Phe Lys Pro Ser Glu Arg Asn Asp
                85                  90                  95 caa gcc tgg tat acc acc ttg acc ata gtg ttc gag cgc acg agc ctc     336
Gln Ala Trp Tyr Thr Thr Leu Thr Ile Val Phe Glu Arg Thr Ser Leu
            100                 105                 110 aag gga tcc acg ctt cag atg atg ggt tac atc cca caa gat ggt cag     384
Lys Gly Ser Thr Leu Gln Met Met Gly Tyr Ile Pro Gln Asp Gly Gln
        115                 120                 125 tgg agc att ttt gga gga act gga caa ctt acc atg gca cgc ggt gtt     432
Trp Ser Ile Phe Gly Gly Thr Gly Gln Leu Thr Met Ala Arg Gly Val
130                 135                 140 gtg aac cat aag gtt gtg cgc caa acc aat ggc ggg agg atg tat aag     480
Val Asn His Lys Val Val Arg Gln Thr Asn Gly Gly Arg Met Tyr Lys
145                 150                 155                 160 atc aac ata cat gcc ttc tat acc ccc ctg ggc gct                     516
Ile Asn Ile His Ala Phe Tyr Thr Pro Leu Gly Ala
                165                 170

<210> SEQ ID NO 5
<211> LENGTH: 39
<212> TYPE: DNA
<213> ORGANISM: Saccharum spp. hybrid
<220> FEATURE:
<221> NAME/KEY: 5' UTR
<222> LOCATION: (1)..(39)
<223> OTHER INFORMATION: FN95-1702 dirigent (DIR) 5' untranslated region

<400> SEQUENCE: 5
acaagcaaga aataaacggt agctgccata actagtaca                          39

<210> SEQ ID NO 6
<211> LENGTH: 35
<212> TYPE: DNA
<213> ORGANISM: Saccharum spp. hybrid
<220> FEATURE:
<221> NAME/KEY: 5' UTR
<222> LOCATION: (1)..(35)
<223> OTHER INFORMATION: Q117 dirigent 5' untranslated region

<400> SEQUENCE: 6
```

```
gcaagaaata aacggtagct gccataacta gtaca                             35

<210> SEQ ID NO 7
<211> LENGTH: 33
<212> TYPE: DNA
<213> ORGANISM: Saccharum spp. hybrid
<220> FEATURE:
<221> NAME/KEY: 5' UTR
<222> LOCATION: (1)..(33)
<223> OTHER INFORMATION: c67 dirigent 5' untranslated region

<400> SEQUENCE: 7
tgaaataaac ggtagctgcc ataactagta caa                              33

<210> SEQ ID NO 8
<211> LENGTH: 6995
<212> TYPE: DNA
<213> ORGANISM: Artificial Sequence
<220> FEATURE:
<223> OTHER INFORMATION: Expression cassette SHDIR5-1(4.706 kb)-GUS
      intron-35S
<220> FEATURE:
<221> NAME/KEY: promoter
<222> LOCATION: (6)..(4711)
<223> OTHER INFORMATION: SHDIR5-1 Promoter
<220> FEATURE:
<221> NAME/KEY: CDS
<222> LOCATION: (4719)..(4727)
<223> OTHER INFORMATION: GUS synthetic exon 1
<220> FEATURE:
<221> NAME/KEY: intron
<222> LOCATION: (4728)..(4917)
<223> OTHER INFORMATION: Castorbean catalase intron
<220> FEATURE:
<221> NAME/KEY: CDS
<222> LOCATION: (4918)..(6765)
<223> OTHER INFORMATION: GUS exon 2 and hexa histidine tag
<220> FEATURE:
<221> NAME/KEY: terminator
<222> LOCATION: (6778)..(6995)
<223> OTHER INFORMATION: 35S

<400> SEQUENCE: 8
agctttgtgg gcgacagctt gatacgtgtc tacaaaccga aatccgatcg tagtcatact    60
ccatgcttca actatgtcag ggaagtcttc acttttccg atataggcgg tgacttcaca    120
tctttcagtt tcatgctcct cgtactccct gccttcatat tctgggcgat ccttgattcc    180
aagtctttgc atggtagcat acaacagctt gggaaagcct tcaatgccta dacagtaact    240
gctggtccaa actccttctg ccatctgaga gagaatagat aagagtaaac attttgaaa    300 aagggaaggc attaagactt tttgtaaaat actcttatat gtaaacact acccagaaag    360 cctaaagtcg cgttctacaa ccaaggaggg gagcagggcg aaaaccatag ggagggaggg    420
aagagcgagg gaatgctcag gagctgctca cctcgtcctg caacgacggc cgagcctggc    480
tcgtgcgtat aggcgtatat ggtatgcacg gacaaattga agcgagagca ggtgagtgag    540
ctgatcgtgc tgctgggtgg tggaggagag cacctccggg tgcccttttta tacaccgagg    600 aagaggggtt gtgccactgg cttgcttgct cgccttcatt ggcattgttg tggccaaata    660
cctgggcagt ggagcgacga gacaacttcc ctggtgattg tacgccgcat gcaaatggac    720
ggtggatgct cagcatgcat ggtcggtgcc taattaccat ggtgaatctt acgtagagtc    780
tttttaggga aaaaaactta gctctaaaat accatatatg tgtatacgtg ctagaggccg    840
gagcattttc ttttttcgaaa aaatatatag tttacgtgca gcatatcaca gattcacggt    900
gcttggcatg catagaattg cacttcgcgt gtgcgaccat ctgtggctga tgatgctccc    960
```

```
tacttttcag catatgacag attcacagtg ttgtcgttag ttcatggcgt ggcgtaggcg    1020
tacatagaat ggaactgtgc gtgtgcgacc atcctgtgtg ggatgctttt cttacccgtg    1080
cgacacggta agtcgtcgct acctaacaat gcgcagcaat gtataggacc gtttaggcct    1140
gtttgatttc ttcctctaga aagagggtgt ggttttatag gcatgaccag agatagcgtg    1200
atgtgatgct acctggcagg tcaagtagca aagtatgaac ctaaaaaaat agaggtgacc    1260
aaatttggaa ctaacttttt caacgccttg gaagcgtaaa tcgtgtcggt aagattttgt    1320
atggtcttga caaagtagaa ggcaattcct gaggtatttg tgcgggaacg ctagattttc    1380
tagattcatg ataagataca attacacaat aaaggaccaa gtcatcaaaa ccgttttatt    1440
tcttgcgtca tgtgtttgta attcgaccat cttaaccatg ccaacgttcc attgaagcac    1500
aacaagcaga cacattatat atgtcccgtg gttgcctgct tttatgctgt gagcaggcta    1560
ctgtttactt agtgtactta gtcatggcat taaaacacca tcgcagacat aatctaagag    1620
caaccacaat gttgcagaaa agtagtccat aggcattaga atagtctata gatagctgaa    1680
aacattatag actttggtat gtatcagtat gtctttggtt acatgacaca catcaggtag    1740
ttaatgcact tatagaatgt ccctaggtac acgtgaattt tttagagtac taccactggg    1800
tggccgtggg tgtgccagtc cttgtcgcca taggcaagtg tgcttgccca gaaccatgct    1860
aacgatgctt aggtttcaag cattctgtgg ccaagttgct tgttaacacg gtaatagagt    1920
tgtttactca ttcaatatgg aatacatgtc atcacaaacg cacaccacat gtatatatct    1980
gaaggtggca acaggggcg tgcatatgc gagcttacac atagccgatg tacacgcaaa     2040
ctactgcagg gatgaactac aatgaggtca tagctaatgc ctactgattc ctcatatatg    2100
aactacaagg aggacactgg gagggctgga tggcacatgc ttatataggc aagagttgga    2160
ggaggaatga ggggcctctg catgcatggg agcagatgca agtatggtag ctgtattaat    2220
ggcgatcaac tccaaccacc gaccaccttg ggagcaacgt gcacacaacc caagccgtct    2280
cttagatgca tggatgcatg tgcaactaca aatgttccta tatggtcggt gaattgtttt    2340
tatttgatgg tacggaggag aggcattaaa tgtgtccacc tacccgactt gttttatct     2400 gatagtagca tgaaggggag ggtgaagatg tccagtctct agtgctttca aatttactga    2460
gtggatttct ggatagcata gggagccact cgtgcatgca tggaaattta ctacgtatct    2520
attgatagta aattcatcaa tgtaaaagga gaaggcacat gtgattgacc cacaccatgg    2580
gcagttgaag atgtccaatc tccagtgctt tcaaatttac tgagtgaatt tctggatagc    2640
atagggagcc acccgtgcat gcatagaaat ttactacata tctattgata gtaaattcat    2700
taatgtaaat ggagaaggca catgtgatgt aaattcctct tgtcgtagta actttttttt    2760
atgcaaagga catgtaaaag tatagtgatg taaatccccc taacgtggta actttctgca    2820
tgcaaagtac atccacagtt ttatattgtc cttgcatgca tggtcattca attttccatc    2880
cacttcattg aattcatcca ctttcttcat ccatccactg ctgaggaagg ctggttgatg    2940
tgctcagtat actaaggaca cctagacttt ttatatagcc tagggaacac ttgtgcatgc    3000
atgaaattta ccgtattgtc tttagcaacc tgtaaatttt gaaccacagg tgacgaaaat    3060
ttatcacact ggctttagct acccatacat tttttgaacc acaggtgacg agaatttacc    3120
acactgactt tagccaccct tacattttga accagaggtg atgcaactcc ttgctgaaga    3180
gtacattttc tgcaggtaaa gaggtcccac ctgggattgc tactacagtg cacatgtcca    3240
tggtaaatct agatggcaag agcacctaca atttttatat agcctagaga ccatacgtgc    3300
atgcacgtaa atttaccgca ttggctaaaa ggaccacagg cgattctaat tcctgctggc    3360
```

```
caacaattttt ttgctagcaa taaagaggtc cttgctatgg tctcacaagt tgcttccttc   3420
catgtaaaaa cctggtagcg gtaaaagctc ctctgtgtaa aaggagaagg cacaatgatg   3480
taaatcccta tagtaacttc ttgcatgcaa agcacacata tattttttgga cggtgcttgc   3540 atgcatgtcc atccaaattt ccatatgctc cgtttaatgc atccacttgc ttgaggatga   3600
caattgcatg catggaagta ctacatgtgg gtcatggagg tactacaaag cacatgtata   3660
attttggtcg gtgcttgcat gcatgcccat ccaaatttcc atctgctccg tttaatccat   3720
ccacttgctt gaggataaca atggcatgca tgaaggtact acatgtgggt catggatgta   3780
ctacaaagca catgtacaat tttggatggt gtttgcatgc atgtccatcc aaaattttta   3840
tctactccca ttttatgcat ccacttgctt gaggctaacc atggcatgca tggagatact   3900
acatgtgggt catagaggta ctacttcatc tgagccgtgg aatttctatc taaggcacca   3960
actaaataga acatacatgg acaccttagg aggccgccta gacggcgcgg cctcatattt   4020
ctaatatata gtgaagggc agtagctgat tgagaatcaa tcaatcaagc acaatacaat   4080
taattaattt tttattcaaa cccaattttt tccttttcca accctaatta tagttctcct   4140
tttgcctcta ggacaaattg acgtgttcca ggtatcctgc tgaaccaaga caaccctag   4200 gtgcacctgt cccgatggag tcccacccag gtaggcattc atagggattc gggtatttcc   4260
tgcaaaaaag cgattaagct ggcttctaaa accggctagc ccggattctg tgggcttcac   4320
taccagatga ttttcatgtg ctccgtgcat tctagcactt gctgtgtaa cccaaactta   4380 catcaacaac tataaatatg ctacttgcag aatgttataa cgacacaact cctaatctac   4440
gaagcctaag tttagttttg ctcggagaca agcaattgtg gcccgtcact atagctaagt   4500
cagagggtag tgggagcagt tgcatcgttg gattgaaaac aggtggatca tattagatac   4560
tacgcatcac atgaacagta aaagtgtaca gtaactgcat tcactgtcat cctgtccacg   4620
cactgcagcc ctctataaat actggcatcc ctcccccccgt tcatagatca cacaacacaa   4680
gcaagaaata aacggtagct gccataacta gcatggtaga tctgagggta aatttctagt   4740
ttttctcctt cattttcttg gttaggaccc ttttctcttt ttattttttt gagctttgat   4800
ctttctttaa actgatctat ttttaattg attggttatg gtgtaaatat tacatagctt   4860
taactgataa tctgattact ttatttcgtg tgtctatgat gatgatgata gttacagaac   4920
cgacgactcg tccgtcctgt agaaacccca acccgtgaaa tcaaaaaact cgacggcctg   4980
tgggcattca gtctggatcg cgaaaactgt ggaattgatc agcgttggtg ggaaagcgcg   5040
ttacaagaaa gccgggcaat tgctgtgcca ggcagtttta acgatcagtt cgccgatgca   5100
gatattcgta attatgcggg caacgtctgg tatcagcgcg aagtctttat accgaaaggt   5160
tgggcaggcc agcgtatcgt gctgcgtttc gatgcggtca ctcattacgg caaagtgtgg   5220
gtcaataatc aggaagtgat ggagcatcag gcggctata cgccatttga agccgatgtc   5280
acgccgtatg ttattgccgg gaaaagtgta cgtatcaccg tttgtgtgaa caacgaactg   5340
aactggcaga ctatcccgcc gggaatggtg attaccgacg aaaacggcaa gaaaaagcag   5400
tcttacttcc atgatttctt taactatgcc ggaatccatc gcagcgtaat gctctacacc   5460
acgccgaaca cctgggtgga cgatatcacc gtggtgacga atgtcgcgca agactgtaac   5520
cacgcgtctg ttgactggca ggtggtggcc aatggtgatg tcagcgttga actgcgtgat   5580
gcggatcaac aggtggttgc aactggacaa ggcactagcg gactttgca agtggtgaat   5640 ccgcacctct ggcaaccggg tgaaggttat ctctatgaac tcgaagtcac agccaaaagc   5700
```

```
cagacagagt ctgatatcta cccgcttcgc gtcggcatcc ggtcagtggc agtgaagggc    5760
caacagttcc tgattaacca caaaccgttc tactttactg gctttggtcg tcatgaagat    5820
gcggacttac gtggcaaagg attcgataac gtgctgatgg tgcacgacca cgcattaatg    5880
gactggattg gggccaactc ctaccgtacc tcgcattacc cttacgctga agagatgctc    5940
gactgggcag atgaacatgg catcgtggtg attgatgaaa ctgctgctgt cggctttcag    6000
ctgtctttag gcattggttt cgaagcgggc aacaagccga agaactgta cagcgaagag    6060 gcagtcaacg gggaaactca gcaagcgcac ttacaggcga ttaaagagct gatagcgcgt    6120
gacaaaaacc acccaagcgt ggtgatgtgg agtattgcca acgaaccgga tacccgtccg    6180
caaggtgcac gggaatattt cgcgccactg gcggaagcaa cgcgtaaact cgacccgacg    6240
cgtccgatca cctgcgtcaa tgtaatgttc tgcgacgctc acaccgatac catcagcgat    6300
ctctttgatg tgctgtgcct gaaccgttat tacggatggt atgtccaaag cggcgatttg    6360
gaaacggcag agaaggtact ggaaaaagaa cttctggcct ggcaggagaa actgcatcag    6420
ccgattatca tcaccgaata cggcgtggat acgttagccg gctgcactc aatgtacacc    6480 gacatgtgga gtgaagagta tcagtgtgca tggctggata tgtatcaccg cgtctttgat    6540
cgcgtcagcg ccgtcgtcgg tgaacaggta tggaatttcg ccgattttgc gacctcgcaa    6600
ggcatattgc gcgttggcgg taacaagaaa gggatcttca ctcgcgaccg caaaccgaag    6660
tcggcggctt ttctgctgca aaaacgctgg actggcatga acttcggtga aaaaccgcag    6720
cagggaggca acaagctag ccaccaccac caccaccacg tgtgaattac aggtgaccga    6780
tctgtcgatc gacaagctcg agtttctcca taataatgtg tgagtagttc ccagataagg    6840
gaattagggt tcctataggg tttcgctcat gtgttgagca tataagaaac ccttagtatg    6900
tatttgtatt tgtaaaatac ttctatcaat aaaatttcta attcctaaaa ccaaaatcca    6960
gtactaaaat ccagatcccc cgaattaatt cggcg                               6995
```

<210> SEQ ID NO 9
<211> LENGTH: 5858
<212> TYPE: DNA
<213> ORGANISM: Artificial Sequence
<220> FEATURE:
<223> OTHER INFORMATION: Expression cassette SHDIR5-1(3.574 kb)-GUS
      intron-35S
<220> FEATURE:
<221> NAME/KEY: promoter
<222> LOCATION: (1)..(3574)
<223> OTHER INFORMATION: SHDIR5-1 Promoter
<220> FEATURE:
<221> NAME/KEY: CDS
<222> LOCATION: (3582)..(3590)
<223> OTHER INFORMATION: GUS synthetic exon 1
<220> FEATURE:
<221> NAME/KEY: intron
<222> LOCATION: (3591)..(3780)
<223> OTHER INFORMATION: Castorbean catalase intron
<220> FEATURE:
<221> NAME/KEY: CDS
<222> LOCATION: (3781)..(5628)
<223> OTHER INFORMATION: GUS exon 2 and hexa histidine tag
<220> FEATURE:
<221> NAME/KEY: terminator
<222> LOCATION: (5641)..(5858)
<223> OTHER INFORMATION: 35S

<400> SEQUENCE: 9

```
cctgtttgat ttcttcctct agaaagaggg tgtggtttta taggcatgac cagagatagc      60
gtgatgtgat gctacctggc aggtcaagta gcaaagtatg aacctaaaaa aatagaggtg     120
```

```
accaaatttg gaactaactt tttcaacgcc ttggaagcgt aaatcgtgtc ggtaagattt      180
tgtatggtct tgacaaagta gaaggcaatt cctgaggtat ttgtgcggga acgctagatt      240
ttctagattc atgataagat acaattacac aataaaggac caagtcatca aaaccgtttt      300
atttcttgcg tcatgtgttt gtaattcgac catcttaacc atgccaacgt tccattgaag      360
cacaacaagc agacacatta tatatgtccc gtggttgcct gcttttatgc tgtgagcagg      420
ctactgttta cttagtgtac ttagtcatgg cattaaaaca ccatcgcaga cataatctaa      480
gagcaaccac aatgttgcag aaaagtagtc cataggcatt agaatagtct atagatagct      540
gaaaacatta tagactttgg tatgtatcag tatgtctttg gttacatgac acacatcagg      600
tagttaatgc acttatagaa tgtccctagg tacacgtgaa ttttttagag tactaccact      660
gggtggccgt gggtgtgcca gtccttgtcg cataggcaa gtgtgcttgc ccagaaccat       720
gctaacgatg cttaggtttc aagcattctg tggccaagtt gcttgttaac acggtaatag     780
agttgtttac tcattcaata tggaatacat gtcatcacaa acgcacacca catgtatata     840
tctgaaggtg gcaaacaggg gcggtgcata tgcgagctta cacatagccg atgtacacgc     900
aaactactgc agggatgaac tacaatgagg tcatagctaa tgcctactga ttcctcatat     960
atgaactaca aggaggacac tgggagggct ggatggcaca tgcttatata ggcaagagtt    1020
ggaggaggaa tgaggggcct ctgcatgcat gggagcagat gcaagtatgg tagctgtatt    1080 aatgcgatc aactccaacc accgaccacc ttggagcaa cgtgcacaca cccaagccg       1140 tctcttagat gcatggatgc atgtgcaact acaaatgttc ctatatggtc ggtgaattgt    1200
ttttatttga tggtacggag gagaggcatt aaatgtgtcc acctacccga cttgttttta    1260
tctgatagta gcatgaaggg gagggtgaag atgtccagtc tctagtgctt caaatttac     1320 tgagtggatt tctggatagc atagggagcc actcgtgcat gcatggaaat ttactacgta    1380
tctattgata gtaaattcat caatgtaaaa ggagaaggca catgtgattg acccacacca    1440
tgggcagttg aagatgtcca atctccagtg cttttcaaatt tactgagtga atttctggat   1500 agcatagga gccacccgtg catgcataga aatttactac atatctattg atagtaaatt    1560
cattaatgta aatggagaag gcacatgtga tgtaaattcc tcttgtcgta gtaacttttt    1620
tttatgcaaa ggacatgtaa aagtatagtg atgtaaatcc ccctaacgtg gtaactttct    1680
gcatgcaaag tacatccaca gttttatatt gtccttgcat gcatggtcat tcaatttttcc   1740 atccacttca ttgaattcat ccactttctt catccatcca ctgctgagga aggctggttg    1800
atgtgctcag tatactaagg acacctagac ttttttatata gcctagggaa cacttgtgca    1860
tgcatgaaat ttaccgtatt gtctttagca acctgtaaat tttgaaccac aggtgacgaa    1920
aatttatcac actggcttta gctacccata catttttttga accacaggtg acgagaattt   1980
accacactga ctttagccac ccttacattt tgaaccagag gtgatgcaac tccttgctga    2040
agagtacatt ttctgcaggt aaagaggtcc cacctgggat tgctactaca gtgcacatgt    2100
ccatggtaaa tctagatggc aagagcacct acaattttta tatagcctag agaccatacg    2160
tgcatgcacg taaatttacc gcattggcta aaaggaccac aggcgattct aattcctgct    2220
ggccaacaat ttttttgctag caataaagag gtccttgcta tggtctcaca agttgcttcc    2280
ttccatgtaa aaacctggta gcggtaaaag ctcctctgtg taaaaggaga aggcacaatg    2340
atgtaaatcc ctatagtaac ttcttgcatg caaagcacac atatatttt ggacggtgct     2400 tgcatgcatg tccatccaaa tttccatatg ctccgtttaa tgcatccact tgcttgagga    2460
tgacaattgc atgcatggaa gtactacatg tgggtcatgg aggtactaca aagcacatgt    2520
```

```
ataattttgg tcggtgcttg catgcatgcc catccaaatt tccatctgct ccgtttaatc    2580
catccacttg cttgaggata acaatggcat gcatgaaggt actacatgtg ggtcatggat    2640
gtactacaaa gcacatgtac aattttggat ggtgtttgca tgcatgtcca tccaaaattt    2700
ttatctactc ccattttatg catccacttg cttgaggcta accatggcat gcatggagat    2760
actacatgtg ggtcatagag gtactacttc atctgagccg tggaatttct atctaaggca    2820
ccaactaaat agaacataca tggacacctt aggaggccgc ctagacggcg cggcctcata    2880
tttctaatat atagtgaagg ggcagtagct gattgagaat caatcaatca agcacaatac    2940
aattaattaa tttttttattc aaacccaatt ttttcctttt ccaaccctaa ttatagttct    3000
ccttttgcct ctaggacaaa ttgacgtgtt ccaggtatcc tgctgaacca agaacaaccc    3060
taggtgcacc tgtcccgatg gagtcccacc caggtaggca ttcataggga ttcgggtatt    3120
tcctgcaaaa aagcgattaa gctggcttct aaaaccggct agcccggatt ctgtgggctt    3180
cactaccaga tgattttcat gtgctccgtg cattctagca ctttgctgtg taacccaaac    3240
ttacatcaac aactataaat atgctacttg cagaatgtta taacgacaca actcctaatc    3300
tacgaagcct aagtttagtt ttgctcggag acaagcaatt gtggcccgtc actatagcta    3360
agtcagaggg tagtgggagc agttgcatcg ttggattgaa acaggtgga tcatattaga    3420 tactacgcat cacatgaaca gtaaaagtgt acagtaactg cattcactgt catcctgtcc    3480
acgcactgca gccctctata aatactggca tccctccccc cgttcataga tcacacaaca    3540
caagcaagaa ataaacggta gctgccataa ctagcatggt agatctgagg gtaaatttct    3600 agttttctc cttcattttc ttggttagga ccctttttctc ttttttatttt tttgagcttt    3660 gatctttctt taaactgatc tatttttttaa ttgattggtt atggtgtaaa tattacatag    3720
ctttaactga taatctgatt actttatttc gtgtgtctat gatgatgatg atagttacag    3780
aaccgacgac tcgtccgtcc tgtagaaacc ccaacccgtg aaatcaaaaa actcgacggc    3840
ctgtgggcat tcagtctgga tcgcgaaaac tgtggaattg atcagcgttg gtgggaaagc    3900
gcgttacaag aaagccgggc aattgctgtg ccaggcagtt ttaacgatca gttcgccgat    3960
gcagatattc gtaattatgc gggcaacgtc tggtatcagc gcgaagtctt tataccgaaa    4020
ggttgggcag ccagcgtat cgtgctgcgt ttcgatgcgg tcactcatta cggcaaagtg    4080
tgggtcaata atcaggaagt gatggagcat cagggcggct atacgccatt tgaagccgat    4140
gtcacgccgt atgttattgc cgggaaaagt gtacgtatca ccgtttgtgt gaacaacgaa    4200
ctgaactggc agactatccc gccgggaatg gtgattaccg acgaaaacgg caagaaaaag    4260
cagtcttact tccatgattt ctttaactat gccggaatcc atcgcagcgt aatgctctac    4320
accacgccga cacctgggt ggacgatatc accgtggtga cgcatgtcgc gcaagactgt    4380
aaccacgcgt ctgttgactg gcaggtggtg gccaatggtg atgtcagcgt tgaactgcgt    4440
gatgcggatc aacaggtggt tgcaactgga caaggcacta gcgggacttt gcaagtggtg    4500
aatccgcacc tctggcaacc gggtgaaggt tatctctatg aactcgaagt cacagccaaa    4560
agccagacag agtctgatat ctacccgctt cgcgtcggca tccggtcagt ggcagtgaag    4620
ggccaacagt tcctgattaa ccacaaaccg ttctacttta ctggctttgg tcgtcatgaa    4680
gatgcggact acgtggcaa aggattcgat aacgtgctga tggtgcacga ccacgcatta    4740
atggactgga ttggggccaa ctcctaccgt acctcgcatt acccttacgc tgaagagatg    4800
ctcgactggg cagatgaaca tggcatcgtg gtgattgatg aaactgctgc tgtcggcttt    4860
```

```
cagctgtctt taggcattgg tttcgaagcg ggcaacaagc cgaaagaact gtacagcgaa    4920
gaggcagtca acggggaaac tcagcaagcg cacttacagg cgattaaaga gctgatagcg    4980
cgtgacaaaa accacccaag cgtggtgatg tggagtattg ccaacgaacc ggatacccgt    5040
ccgcaaggtg cacgggaata tttcgcgcca ctggcggaag caacgcgtaa actcgacccg    5100
acgcgtccga tcacctgcgt caatgtaatg ttctgcgacg ctcacaccga taccatcagc    5160
gatctctttg atgtgctgtg cctgaaccgt tattacggat ggtatgtcca aagcggcgat    5220
ttggaaacgg cagagaaggt actggaaaaa gaacttctgg cctggcagga gaaactgcat    5280
cagccgatta tcatcaccga atacggcgtg gatacgttag ccgggctgca ctcaatgtac    5340
accgacatgt ggagtgaaga gtatcagtgt gcatggctgg atatgtatca ccgcgtcttt    5400
gatcgcgtca gcgccgtcgt cggtgaacag gtatggaatt tcgccgattt tgcgacctcg    5460
caaggcatat tgcgcgttgg cggtaacaag aaagggatct tcactcgcga ccgcaaaccg    5520
aagtcggcgg cttttctgct gcaaaaacgc tggactggca tgaacttcgg tgaaaaaccg    5580
cagcagggag gcaaacaagc tagccaccac caccaccacc acgtgtgaat tacaggtgac    5640
cgatctgtcg atcgacaagc tcgagtttct ccataataat gtgtgagtag ttcccagata    5700
agggaattag ggttcctata gggtttcgct catgtgttga gcatataaga aaccettagt    5760 atgtatttgt atttgtaaaa tacttctatc aataaaattt ctaattccta aaaccaaaat    5820
ccagtactaa aatccagatc ccccgaatta attcggcg                            5858
```